US010301685B2

(12) United States Patent
Brase et al.

(10) Patent No.: US 10,301,685 B2
(45) Date of Patent: May 28, 2019

(54) METHOD FOR PREDICTING THE BENEFIT FROM INCLUSION OF TAXANE IN A CHEMOTHERAPY REGIMEN IN PATIENTS WITH BREAST CANCER

(71) Applicant: Sividon Diagnostics GmbH, Cologne (DE)

(72) Inventors: Jan Brase, Cologne (DE); Ralf Kronenwett, Cologne (DE); Karin Fisch, Cologne (DE); Mathias Gehrmann, Cologne (DE); Marcus Schmidt, Mainz-Kastel (DE)

(73) Assignee: Sividon Diagnostics GmbH (DE)

( * ) Notice: Subject to any disclaimer, the term of this patent is extended or adjusted under 35 U.S.C. 154(b) by 0 days.

(21) Appl. No.: 15/799,699

(22) Filed: Oct. 31, 2017

(65) Prior Publication Data

US 2018/0135133 A1 May 17, 2018

Related U.S. Application Data

(63) Continuation of application No. 14/765,294, filed as application No. PCT/EP2014/051937 on Jan. 31, 2014, now abandoned.

(30) Foreign Application Priority Data

Feb. 1, 2013 (EP) .................................... 13153755
Mar. 1, 2013 (EP) .................................... 13157350

(51) Int. Cl.
*C12Q 1/6886* (2018.01)
*C12Q 1/6809* (2018.01)

(52) U.S. Cl.
CPC ..... *C12Q 1/6886* (2013.01); *C12Q 2600/106* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 2006/0024692 | A1 | 2/2006 | Nakamura et al. |
| 2006/0166231 | A1 | 7/2006 | Baker et al. |
| 2006/0234287 | A1 | 10/2006 | Erlander et al. |
| 2007/0099209 | A1 | 5/2007 | Clarke et al. |
| 2007/0134688 | A1 | 6/2007 | Symmans et al. |
| 2008/0125581 | A1 | 5/2008 | Deming et al. |
| 2010/0105564 | A1 | 4/2010 | Park et al. |
| 2011/0145176 | A1 | 6/2011 | Perou et al. |
| 2011/0306513 | A1 | 12/2011 | Song et al. |
| 2012/0065084 | A1 | 3/2012 | Sotiriou et al. |
| 2012/0142624 | A1 | 6/2012 | Yang et al. |
| 2014/0349878 | A1 | 11/2014 | Wang et al. |

FOREIGN PATENT DOCUMENTS

| | | |
|---|---|---|
| EP | 1134738 | 9/2001 |
| EP | 2036988 | 3/2009 |
| EP | 2163649 | 3/2010 |
| EP | 2553118 | 2/2013 |
| WO | 2003001985 | 1/2003 |
| WO | 2006084272 | 8/2006 |
| WO | 2006119593 | 11/2006 |
| WO | 2006133923 | 3/2007 |
| WO | 2008006517 | 1/2008 |
| WO | 2008070571 | 6/2008 |
| WO | 2008079269 | 7/2008 |
| WO | 2008154249 | 12/2008 |
| WO | 2009095319 | 8/2009 |
| WO | 2009114836 | 9/2009 |
| WO | 2009132928 | 11/2009 |
| WO | 2006138275 | 12/2009 |
| WO | 2009158143 | 12/2009 |
| WO | 2010003771 | 1/2010 |
| WO | 2010003773 | 1/2010 |
| WO | 2010076322 | 7/2010 |
| WO | 2011120984 | 10/2011 |
| WO | 2011121028 | 10/2011 |
| WO | 2012153187 | 11/2012 |
| WO | 2013014296 | 1/2013 |
| WO | 2015121300 | 8/2015 |

OTHER PUBLICATIONS

International Preliminary Report on Patentability and Written Opinion from Application No. PCT/EP2009/057418, dated Dec. 18, 2010.
International Preliminary Report on Patentability and Written Opinion from Application No. PCT/EP2009/057426, dated Dec. 18, 2010.
International Preliminary Report on Patentability and Written Opinion from Application No. PCT/EP2011/054855, dated Oct. 2, 2012.
International Preliminary Report on Patentability and Written Opinion from Application No. PCT/EP2012/064865, dated Jan. 28, 2014.
International Preliminary Report on Patentability and Written Opinion from Application No. PCT/EP2014/051937, dated Aug. 4, 2015.
International Preliminary Report on Patentability and Written Opinion from Application No. PCT/EP2015/052081, dated Aug. 18, 2016.

(Continued)

*Primary Examiner* — Channing S Mahatan
(74) *Attorney, Agent, or Firm* — Myriad Genetics, Inc. IP Department

(57) ABSTRACT

Described herein are methods for predicting a benefit from inclusion of taxane in a chemotherapy regimen in a patient suffering from or at risk of developing recurrent neoplastic disease, in particular breast cancer. Said method includes the steps of determining the expression levels of the marker genes S100P and PCSK6 and mathematically combining the expression level values to yield a combined score and comparing said combined score to a reference-value, wherein a high combined score is indicative of a benefit from including a taxane in a chemotherapy regimen of said patient and a low combined score is indicative of not having a benefit from including a taxane in a chemotherapy regimen.

10 Claims, 6 Drawing Sheets

Specification includes a Sequence Listing.

(56) References Cited

OTHER PUBLICATIONS

International Preliminary Report on Patentability and Written Opinion from Application No. PCT/US2010/024603, dated Sep. 28, 2010.
International Search Report and Written Opinion from Application No. PCT/EP2017/055601, dated Apr. 18, 2017.
International Search Report from Application No. PCT/EP2009/057418, dated Nov. 5, 2009.
International Search Report from Application No. PCT/EP2009/057426, dated Nov. 2, 2009.
International Search Report from Application No. PCT/EP2011/054855, dated Sep. 21, 2011.
International Search Report from Application No. PCT/EP2012/064865, dated Dec. 18, 2012.
International Search Report from Application No. PCT/EP2014/051937, dated Apr. 1, 2014.
International Search Report from Application No. PCT/US2010/024603, dated Sep. 28, 2010.
Jemal et al., CA Cancer J Clin., vol. 61, No. 2, 2011, pp. 69-90.
Korean Communication from Application No. 10-2012-7025899, dated Aug. 22, 2017.
Liedtke et al., Journal of Clinical Oncology, 2009, vol. 27, No. 19, pp. 3185-3191.
Lin et al., J Neurochem, Jan. 2008, vol. 104, No. 2, pp. 400-408.
Liu et al., PLOS One, vol. 7, No. 5, 2012, pp. e36383.
Loussouarn et al, BR J Cancer, vol. 101, No. 1, 2009, pp. 166-173.
Lu et al., Clinical Cancer Research, vol. 10, 2004, pp. 3291-3300.
Martin et al., PLOS One, vol. 3, No. 8, 2008, pp. e2994-1-e2994-9.
May et al., Science, vol. 241, 1988, pp. 1441-1449.
Misset et al., Journal of Clinical Oncology, 1996, vol. 14, No. 4, pp. 1136-1145.
Nowak et al, Nature, May 2002, vol. 417, No. 6887, pp. 424-428.
O'Neill et al., Molecular Cancer, 2013, vol. 12, No. 69, pp. 1-9.
Paik et al., New England Journal of Medicine, vol. 351, No. 27, 2004, pp. 2817-2826.
Partial European Search Report from Application No. 11175852, dated Nov. 9, 2011.
Pockaj et al., Annals of Surgical Oncology, vol. 11, No. 3, 2004, pp. 328-339.
Rathnagiriswaran et al., Mar. 2010, Int. J. Oncol. vol. 36, No. 3, p. 607-616.
Rosemary et al., Journal of Andrology, 2008, vol. 29, No. 4, pp. 389-403.
Ross et al., The Oncologist, vol. 13, No. 5, 2008, pp. 477-493.
Russian Fifth Office Action from Application 2012146343/10(074392).
Russian First Office Action from Application 2012146343/10(074392).
Russian Forth Office Action from Application 2012146343/10(074392).
Russian Office Action Response from Application No. 2012146343, dated Nov. 7, 2016.
Russian Second Office Action from Application 2012146343/10(074392).
Russian Third Office Action from Application 2012146343/10(074392).
Saito-Hisaminato et al., DNA Research, vol. 9, 2002, pp. 35-45.
Shapiro et al., N Engl J Med, vol. 344, 2001, pp. 1997-2008.
Soonmyung et al., Natures Clinical Practice Oncology, vol. 2, No. 5, 2005, pp. 246-254.
Sorlie et al., PNAS, vol. 98, No. 19, 2001, pp. 10869-10874.
Sotiriou et al., Journal of the National Cancer Institute, 2006, vol. 98, No. 4, pp. 262-272.
Tabchy et al., Clinical Cancer Research, 2010, vol. 16, No. 21, pp. 5351-5361.
Takahashi et al., BMC Bioinformatics, 2006, 7, 399, pp. 1-11.
Taylor et al., Breast Cancer Research, vol. 12, No. 3, pp. R39.
Terasaka et al., Environmental Health Perspectives, 2004, vol. 112, No. 7, pp. 773-781.
Tian et al., Tissue Eng Mar.-Apr. 2005, vol. 11, No. 3-4, pp. 513-525.
Vandesompele et al., Genome Biology, vol. 3, 2002, pp. 1-11.
Veer et al., Nature, vol. 415, 2002, pp. 530-536.
Affymetrix Genechip bHuman Genome U133 plus 2.0 Array, GEO.
Akech et al., Biochemical and Biophysical Research Communications, vol. 333, No. 1, 2005, pp. 35-41.
Andre et al., JCO, vol. 26, No. 16, 2008, pp. 2636-2643.
Benner et al., Trends in Genetics, vol. 17, 2001, pp. 414-418.
Canadian Office Action from Application No. 2,793,133 dated Feb. 7, 2017.
Canadian Office Action Response from Application No. 2,793,133 dated Jul. 18, 2017.
Chanrion et al., Clin. Cancer Res., vol. 14, No. 6, 2008, pp. 1744-1752.
Cheung et al., Nature Genetics, vol. 33, 2003, pp. 422-425.
Couzin-Frankel et al., Science, vol. 329, 2010, pp. 614-615.
Dai et al., Cancer Research, vol. 65, No. 10, 2005, pp. 4059-4066.
Decock et al., BMC Cancer, vol. 8, No. 1, 2008, pp. 1-8.
Desmedt et al., Cell Cycle, vol. 5, No. 9, 2006, pp. 2198-2202.
Dondoni et al., Angew Cehm Int Ed Engl, 2008, vol. 47, No. 47, pp. 8995-8997.
Dorssers et al., Breast Cancer Research, vol. 7, No. 1, 2004, pp. R82-R92.
Esteva et al., Clin. Cancer Res, vol. 11, 2005, pp. 3315-3319.
European Communication from Application No. 11710526.2, dated Aug. 22, 2013.
European Communication from Application No. 12740974.6, dated May 11, 2015.
European Communication from Application No. 14705056.1, dated Aug. 24, 2016.
European Communication from Application No. 15702464.7, dated Aug. 30, 2017.
European Communication from Application No. 16184484.0 dated Oct. 18, 2017.
European Communication Response from Application No. 11710526.2, dated May 2, 2013.
European Communication Response from Application No. 11710526.2, dated Feb. 17, 2014.
European Communication Response from Application No. 12740974.6, dated Jul. 2, 2014.
European Communication Response from Application No. 12740974.6, dated Sep. 10, 2015.
European Communication Response from Application No. 12740974.6, dated Mar. 11, 2016.
European Communication Response from Application No. 14188791.9, dated Aug. 19, 2015.
European Communication Response from Application No. 14188791.9, dated Dec. 22, 2014.
European Communication Response from Application No. 14705056.1, dated Nov. 22, 2016.
European Communication Response from Application No. 15702464.7, dated Mar. 2, 2017.
European Communication Response from Application No. 16184484.0, dated Nov. 15, 2016.
European Communication Response from Application No. 16184484.0, dated Sep. 20, 2017.
European Intention to Grant from Application 11710526.2, dated Apr. 23, 2014.
European Intention to Grant from Application 12740974.6 dated Jun. 15, 2016.
European Intention to Grant from Application 14188791.9, dated Oct. 29, 2015.
European Intention to Grant from Application No. 12740974.6, dated Nov. 19, 2015.
European Intention to Grant from Application No. 14705056.1, dated Apr. 18, 2017.
Extended European Search Report and Opinion from Application 14188791.9 dated Feb. 6, 2015.
Extended European Search Report from Application 16180991.8 dated Jan. 26, 2017.
Extended European Search Report from Application 16184484.0 dated Feb. 9, 2017.

(56) References Cited

OTHER PUBLICATIONS

Extended European Search Report from Application No. 16159481.7, dated Sep. 8, 2016.
Ganz et al., JNCI, vol. 94, No. 1, 2002, pp. 39-49.
Gao et al., Chinese Medical Journal, vol. 121, No. 16, 2008, pp. 1563-1568.
Gianni et al., JCO, vol. 27, 2009, pp. 2474-2481.
Glas et al., BMC Genomics, vol. 7, No. 278, 2006, pp. 1-10.
Greenbaum et al., Genome Biology, vol. 4, No. 117, 2003, pp. 1-8.
Habel et al., Breast Cancer Research, vol. 8, 2006, pp. 1-15.
Henderson et al., Journal of Clinical Oncology, vol. 21, No. 6, 2003, pp. 976-983.
Hess et al., J Clin Oncol., vol. 24, No. 26, 2006, pp. 4236-4244.
Hess et al., Journal of Clinical Oncology, vol. 29, No. 34, 2011, pp. 4516-4525.
Hou et al., J Neurosci Meth, Oct. 2005, vol. 148, No. 1, pp. 60-70.
Canadian Office Action from Application No. 2,793,133 dated Feb. 26, 2018, 4 pages.
Vegran et al., British Journal of Cancer, 2009, vol. 101, No. 8, pp. 1357-1364.
Villeneuve et al., Breast Cancer and Treatment, vol. 96, No. 1, 2006, pp. 17-39.
Von Minckwitz et al., Cancer Res, vol. 69 (supp), No. 24, 2009, pp. 635S.
Wang et al., Cancer Letters, vol. 272, No. 2, 2008, pp. 277-284.
Wang et al., Lancet, vol. 365, No. 9460, 2005, pp. 671-679.
Wray et al., vol. 121, No. 21, Apr. 8, 2013, pp. 4359-4365.
Zhijuan et al., Oncology Reports, vol. 20, 2008, pp. 325-332.
Canadian Office Action Response from Application No. 2,793,133 dated Aug. 21, 2018, 2 pages.
European Intention to Grant from Application 16184484.0, dated Jun. 22, 2018, 7 pages.
European Communication from Application No. 15702464.7, dated Jun. 8, 2018, 5 pages.

METHOD FOR PREDICTING THE BENEFIT FROM INCLUSION OF TAXANE IN A CHEMOTHERAPY REGIMEN IN PATIENTS WITH BREAST CANCER

CROSS-REFERENCE TO RELATED APPLICATION

This application a continuation of U.S. patent application Ser. No. 14/765,294, filed Jul. 31, 2015, which is a U.S. National Phase of International Application No. PCT/EP2014/051937, filed Jan. 31, 2014, which claims priority to European Application No. 13153755.7, filed Feb. 1, 2013, and European Application No. 13157350.3, filed Mar. 1, 2013, the entire contents each of which are incorporated by reference herein.

SEQUENCE LISTING

This application contains a Sequence Listing which was submitted in ASCII format and is incorporated by reference in its entirety. Said ASCII copy, created Jan. 9, 2018, is named 7003-01-1C-2018-01-09-ST25.txt and is 241,664 bytes in size. Said ASCII copy is a copy of the sequence listing filed with International Application No. PCT/EP2014/051937, filed Jan. 31, 2014.

TECHNICAL FIELD

The present invention relates to methods, kits and systems for predicting the benefit from inclusion of taxane in a chemotherapy regimen based on the measurements of gene expression levels in tumor samples of breast cancer patients.

BACKGROUND OF THE INVENTION

Breast cancer is the most common tumor type and the leading cause of cancer-related death in women (Jemal et al., CA Cancer J Clin., 2011). Considerable progress has been made in terms of breast cancer diagnosis and treatment in the last years.

After surgical removal of the primary tumor, breast cancer patients are frequently treated with radiotherapy, hormone therapy and cytotoxic chemotherapy to reduce the risk of recurrence. Today, anthracycline and taxane-based treatment strategies are commonly used in clinical routine, since these regimens have been shown to be superior compared to other standard chemotherapies.

Several large clinical trials demonstrated that the addition of taxanes to anthracycline-based treatment strategies results in an improved clinical outcome (Martin et al., NEJM, 2005, Gianni, J C O, 2009). Although, taxanes are among the most active agents, the absolute benefit of taxane-based treatment is modest (3-5%) and has to be balanced according to serious side-effects.

To reduce the number of patients suffering from side effects without a clear benefit of the therapy regimen, there is a great need for novel predictive tests to identify a group of patients that can be safely treated with conventional chemotherapy and a subgroup that has a significant benefit of taxane-based treatment.

Considerable efforts have been made to identify biomarkers that allow a prediction of a specific treatment while minimizing the risk of unnecessary side effects. Ki67—a well-known cell proliferation marker—has been described to predict the benefit from adjuvant taxane-based treatment in the PACS01 trial (Penault-Llorca, J C O, 2008). However, neither the association between Ki67 index and treatment effect nor any other clinicopathological parameter or biomarker predictive for the efficiency of taxanes has been validated so far.

The most challenging treatment decision in this context concerns ER+/HER2-breast cancer patients, for which classical clinical factors like grading, tumor size or lymph node involvement do not provide a clear answer to the question whether to use chemotherapy or not and what type of treatment therapy is appropriate for the individual patient.

DEFINITIONS

Unless defined otherwise, technical and scientific terms used herein have the same meaning as commonly understood by one of ordinary skill in the art to which this invention belongs.

The term “tumor” as used herein, refers to all neoplastic cell growth and proliferation, whether malignant or benign, and all pre-cancerous and cancerous cells and tissues.

The term “cancer” is not limited to any stage, grade, histomorphological feature, aggressivity, or malignancy of an affected tissue or cell aggregation.

The term “prediction”, as used herein, relates to an individual assessment of the malignancy of a tumor, or to the expected survival rate (OAS, overall survival or DFS, disease free survival) of a patient, if the tumor is treated with a given therapy.

A “benefit” from a given therapy is an improvement in health or wellbeing that can be observed in patients under said therapy, but isn’t observed in patients not receiving this therapy. Non-limiting examples commonly used in oncology to gauge a benefit from therapy are survival, disease free survival, metastasis free survival, disappearance of metastasis, tumor regression, and tumor remission.

A “risk” is understood to be a probability of a subject or a patient to develop or arrive at a certain disease outcome. The term “risk” in the context of the present invention is not meant to carry any positive or negative connotation with regard to a patient’s wellbeing but merely refers to a probability or likelihood of an occurrence or development of a given condition.

The term “node positive”, “diagnosed as node positive”, “node involvement” or “lymph node involvement” means a patient having previously been diagnosed with lymph node metastasis. It shall encompass both draining lymph node, near lymph node, and distant lymph node metastasis. This previous diagnosis itself shall not form part of the inventive method. Rather it is a precondition for selecting patients whose samples may be used for one embodiment of the present invention. This previous diagnosis may have been arrived at by any suitable method known in the art, including, but not limited to lymph node removal and pathological analysis, biopsy analysis, in-vitro analysis of biomarkers indicative for metastasis, imaging methods (e.g. computed tomography, X-ray, magnetic resonance imaging, ultrasound), and intraoperative findings.

In the context of the present invention a “biological sample” is a sample which is derived from or has been in contact with a biological organism. Examples for biological samples are: cells, tissue, body fluids, lavage fluid, smear samples, biopsy specimens, blood, urine, saliva, sputum, plasma, serum, cell culture supernatant, and others. A “tumor sample” is a biological sample containing tumor cells, no matter if intact or degraded.

A “gene” is a set of segments of nucleic acid that contains the information necessary to produce a functional RNA product. A "gene product" is a biological molecule produced through transcription or expression of a gene, e.g. an mRNA or the translated protein.

An "mRNA" is the transcribed product of a gene or a part of a gene and shall have the ordinary meaning understood by a person skilled in the art. A "molecule derived from an mRNA" is a molecule which is chemically or enzymatically obtained from an mRNA template, such as cDNA.

The term "expression level" refers to a determined level of gene expression. This may be a determined level of gene expression as an absolute value or compared to a reference gene (e.g. a housekeeping gene) or to a computed average expression value (e.g. in DNA chip analysis) or to another informative gene without the use of a reference sample. The expression level of a gene may be measured directly, e.g. by obtaining a signal wherein the signal strength is correlated to the amount of mRNA transcripts of that gene or it may be obtained indirectly at a DNA or protein level, e.g. by immunohistochemistry, CISH, ELISA or RIA methods. The expression level may also be obtained by way of a competitive reaction to a reference sample. An expression value which is determined by measuring some physical parameter in an assay, e.g. fluorescence emission, may be assigned a numerical value which may be used for further processing of information.

A "reference pattern of expression levels", within the meaning of the invention shall be understood as being any pattern of expression levels that can be used for the comparison to another pattern of expression levels. In a preferred embodiment of the invention, a reference pattern of expression levels is, e.g., an average pattern of expression levels observed in a group of healthy individuals, diseased individuals, or diseased individuals having received a particular type of therapy, serving as a reference group.

As all measurement results also gene expressions values or combined scores, consisting of a mathematical combination of one or more gene expression values, require to be compared to a "reference-value" to get a meaning in a clinical context. As such an expression value or a combined score exceeding such a "reference-value", by way of example may mean an improved or worsened likelihood of survival for a patient. Such "reference-value" can be a numerical cutoff value, it can be derived from a reference measurement of one or more other genes in the same sample, or one or more other genes and/or the same gene in one other sample or in a plurality of other samples. This is how "reference-value" within the meaning of this invention should be understood.

The term "mathematically combining expression levels", within the meaning of the invention shall be understood as deriving a numeric value from a determined expression level of a gene and applying an algorithm to obtain a combined numerical value or combined score.

An "algorithm" is a process that performs some sequence of operations to process an information.

The term "cytotoxic treatment" or "cytotoxic chemotherapy" refers to various treatment modalities affecting cell proliferation and/or survival. The treatment may include administration of alkylating agents, antimetabolites, anthracyclines, plant alkaloids, topoisomerase inhibitors, and other antitumour agents, including monoclonal antibodies and kinase inhibitors. In particular, the cytotoxic treatment may relate to a treatment comprising microtubule-stabilizing drugs such as taxanes or epothilones.

The term "neoadjuvant chemotherapy" relates to a preoperative therapy regimen consisting of a panel of hormonal, chemotherapeutic and/or antibody agents, which is aimed to shrink the primary tumor, thereby rendering local therapy (surgery or radiotherapy) less destructive or more effective, enabling breast conserving surgery and evaluation of responsiveness of tumor sensitivity towards specific agents in vivo.

A "microtubule stabilizing agent-based" treatment or therapy is a treatment or therapy comprising taxol or therapeutically effective derivatives thereof, epothilones or therapeutically effective derivatives thereof or other microtubule stabilizing cytotoxic drugs.

A "taxane-based" treatment or therapy is a treatment or therapy comprising taxol or therapeutically effective derivatives thereof. The principal mechanism of the taxane class of drugs is the disruption of microtubule function.

The term "hybridization-based method", as used herein, refers to methods imparting a process of combining complementary, single-stranded nucleic acids or nucleotide analogues into a single double stranded molecule. Nucleotides or nucleotide analogues will bind to their complement under normal conditions, so two perfectly complementary strands will bind to each other readily. In bioanalytics, very often labeled, single stranded probes are in order to find complementary target sequences. If such sequences exist in the sample, the probes will hybridize to said sequences which can then be detected due to the label. Other hybridization based methods comprise microarray and/or biochip methods. Therein, probes are immobilized on a solid phase, which is then exposed to a sample. If complementary nucleic acids exist in the sample, these will hybridize to the probes and can thus be detected. These approaches are also known as "array based methods". Yet another hybridization based method is PCR, which is described above. When it comes to the determination of expression levels, hybridization based methods may for example be used to determine the amount of mRNA for a given gene.

An oligonucleotide capable of specifically binding sequences a gene or fragments thereof relates to an oligonucleotide which specifically hybridizes to a gene or gene product, such as the gene's mRNA or cDNA or to a fragment thereof. To specifically detect the gene or gene product, it is not necessary to detect the entire gene sequence. A fragment of about 20-150 bases will contain enough sequence specific information to allow specific hybridization.

The term "a PCR based method" as used herein refers to methods comprising a polymerase chain reaction (PCR). This is a method of exponentially amplifying nucleic acids, e.g. DNA by enzymatic replication in vitro. As PCR is an in vitro technique, it can be performed without restrictions on the form of DNA, and it can be extensively modified to perform a wide array of genetic manipulations. When it comes to the determination of expression levels, a PCR based method may for example be used to detect the presence of a given mRNA by (1) reverse transcription of the complete mRNA pool (the so called transcriptome) into cDNA with help of a reverse transcriptase enzyme, and (2) detecting the presence of a given cDNA with help of respective primers. This approach is commonly known as reverse transcriptase PCR (rtPCR). Moreover, PCR-based methods comprise e.g. real time PCR, and, particularly suited for the analysis of expression levels, kinetic or quantitative PCR (qPCR).

The term "Quantitative PCR" (qPCR)" refers to any type of a PCR method which allows the quantification of the template in a sample. Quantitative real-time PCR comprise different techniques of performance or product detection as for example the TaqMan technique or the LightCycler technique. The TaqMan technique, for examples, uses a dual-labelled fluorogenic probe. The TaqMan real-time PCR measures accumulation of a product via the fluorophore during the exponential stages of the PCR, rather than at the end point as in conventional PCR. The exponential increase of the product is used to determine the threshold cycle, CT, i.e. the number of PCR cycles at which a significant exponential increase in fluorescence is detected, and which is directly correlated with the number of copies of DNA template present in the reaction. The set up of the reaction is very similar to a conventional PCR, but is carried out in a real-time thermal cycler that allows measurement of fluorescent molecules in the PCR tubes. Different from regular PCR, in TaqMan real-time PCR a probe is added to the reaction, i.e., a single-stranded oligonucleotide complementary to a segment of 20-60 nucleotides within the DNA template and located between the two primers. A fluorescent reporter or fluorophore (e.g., 6-carboxyfluorescein, acronym: FAM, or tetrachlorofluorescein, acronym: TET) and quencher (e.g., tetramethylrhodamine, acronym: TAMRA, of dihydrocyclopyrroloindole tripeptide "minor groove binder", acronym: MGB) are covalently attached to the 5' and 3' ends of the probe, respectively [2]. The close proximity between fluorophore and quencher attached to the probe inhibits fluorescence from the fluorophore. During PCR, as DNA synthesis commences, the 5' to 3' exonuclease activity of the Taq polymerase degrades that proportion of the probe that has annealed to the template (Hence its name: Taq polymerase+TacMan). Degradation of the probe releases the fluorophore from it and breaks the close proximity to the quencher, thus relieving the quenching effect and allowing fluorescence of the fluorophore. Hence, fluorescence detected in the real-time PCR thermal cycler is directly proportional to the fluorophore released and the amount of DNA template present in the PCR.

By "array" or "matrix" an arrangement of addressable locations or "addresses" on a device is meant. The locations can be arranged in two dimensional arrays, three dimensional arrays, or other matrix formats. The number of locations can range from several to at millions. Most importantly, each location represents a totally independent reaction site. Arrays include but are not limited to nucleic acid arrays, protein arrays and antibody arrays. A "nucleic acid array" refers to an array containing nucleic acid probes, such as oligonucleotides, nucleotide analogues, polynucleotides, polymers of nucleotide analogues, morpholinos or larger portions of genes. The nucleic acid and/or analogue on the array is preferably single stranded. Arrays wherein the probes are oligonucleotides are referred to as "oligo-nucleotide arrays" or "oligonucleotide chips." A "microarray," herein also refers to a "biochip" or "biological chip", an array of regions having a density of discrete regions of at least about 100/cm2, and preferably at least about 1000/cm2.

The term "therapy modality", "therapy mode", "regimen" or "chemo regimen" as well as "therapy regimen" refers to a timely sequential or simultaneous administration of anti-tumor, and/or anti vascular, and/or immune stimulating, and/or blood cell proliferative agents, and/or radiation therapy, and/or hyperthermic, and/or hypothermia for cancer therapy. The administration of these can be performed in an adjuvant and/or neoadjuvant mode. The composition of such "protocol" may vary in the dose of the single agent, time-frame of application and frequency of administration within a defined therapy window. Currently various combinations of various drugs and/or physical methods, and various schedules are under investigation.

The term "measurement at a protein level", as used herein, refers to methods which allow for the quantitative and/or qualitative determination of one or more proteins in a sample. These methods include, among others, protein purification, including ultracentrifugation, precipitation and chromatography, as well as protein analysis and determination, including immunohistochemistry, immunofluorescence, ELISA (enzyme linked immunoassay), RIA (radioimmunoassay) or the use of protein microarrays, two-hybrid screening, blotting methods including western blot, one- and two dimensional gelelectrophoresis, isoelectric focusing as well as methods being based on mass spectrometry like MALDI-TOF and the like.

The term "marker gene" as used herein, refers to a differentially expressed gene whose expression pattern may be utilized as part of a predictive, prognostic or diagnostic process in malignant neoplasia or cancer evaluation, or which, alternatively, may be used in methods for identifying compounds useful for the treatment or prevention of malignant neoplasia and head and neck, colon or breast cancer in particular. A marker gene may also have the characteristics of a target gene.

The term "immunohistochemistry" or IHC refers to the process of localizing proteins in cells of a tissue section exploiting the principle of antibodies binding specifically to antigens in biological tissues. Immunohistochemical staining is widely used in the diagnosis and treatment of cancer. Specific molecular markers are characteristic of particular cancer types. IHC is also widely used in basic research to understand the distribution and localization of biomarkers in different parts of a tissue.

A "score" within the meaning of the invention shall be understood as a numeric value, which is related to the outcome of a patient's disease and/or the response of a tumor to a specific chemotherapy treatment. The numeric value is derived by combining the expression levels of marker genes using prespecified coefficients in a mathematic algorithm. The expression levels can be employed as CT or delta-CT values obtained by kinetic RT-PCR, as absolute or relative fluorescence intensity values obtained through microarrays or by any other method useful to quantify absolute or relative RNA levels. Combining these expression levels can be accomplished for example by multiplying each expression level with a defined and specified coefficient and summing up such products to yield a score. The score may be also derived from expression levels together with other information, e. g. clinical data like tumor size, lymph node status or tumor grading as such variables can also be coded as numbers in an equation. The score may be used on a continuous scale to predict the response of a tumor to a specific chemotherapy and/or the outcome of a patient's disease. Cut-off values may be applied to distinguish clinical relevant subgroups. Cut-off values for such scores can be determined in the same way as cut-off values for conventional diagnostic markers and are well known to those skilled in the art. A useful way of determining such cut-Off value is to construct a receiver-operator curve (ROC curve) on the basis of all conceivable cut-off values, determine the single point on the ROC curve with the closest proximity to the upper left corner (0/1) in the ROC plot. Obviously, most of the time cut-off values will be determined by less formalized procedures by choosing the combination of sensitivity and specificity determined by such cutoff value providing the most beneficial medical information to the problem investigated.

The "response of a tumor to chemotherapy", within the meaning of the invention, relates to any response of the tumor to cytotoxic chemotherapy, preferably to a change in tumor mass and/or volume after initiation of neoadjuvant chemotherapy and/or prolongation of time to distant metastasis or time to death following neoadjuvant or adjuvant chemotherapy. Tumor response may be assessed in a neoadjuvant situation where the size of a tumor after systemic intervention can be compared to the initial size and dimensions as measured by CT, PET, mammogram, ultrasound or palpation, usually recorded as "clinical response" of a patient. Response may also be assessed by caliper measurement or pathological examination of the tumor after biopsy or surgical resection. Response may be recorded in a quantitative fashion like percentage change in tumor volume or in a qualitative fashion like "no change" (NC), "partial remission" (PR), "complete remission" (CR) or other qualitative criteria. Assessment of tumor response may be done early after the onset of neoadjuvant therapy e.g. after a few hours, days, weeks or preferably after a few months. A typical endpoint for response assessment is upon termination of neoadjuvant chemotherapy or upon surgical removal of residual tumor cells and/or the tumor bed. This is typically three month after initiation of neoadjuvanttherapy. Response may also be assessed by comparing time to distant metastasis or death of a patient following neoadjuvant or adjuvant chemotherapy with time to distant metastasis or death of a patient not treated with chemotherapy.

The term "therapy" refers to a timely sequential or simultaneous administration of anti-tumor, and/or anti vascular, and/or anti stroma, and/or immune stimulating or suppressive, and/or blood cell proliferative agents, and/or radiation therapy, and/or hyperthermia, and/or hypothermia for cancer therapy. The administration of these can be performed in an adjuvant and/or neoadjuvant mode. The composition of such "protocol" may vary in the dose of each of the single agents, timeframe of application and frequency of administration within a defined therapy window. Currently various combinations of various drugs and/or physical methods, and various schedules are under investigation. A "taxane/anthracycline-containing chemotherapy" is a therapy modality comprising the administration of taxane and/or anthracycline and therapeutically effective derivates thereof.

WO 2008/006517 A2 discloses methods and kits for the prediction of a likely outcome of chemotherapy in a cancer patient. More specifically, the invention relates to the prediction of tumour response to chemotherapy based on measurements of expression levels of a small set of marker genes. The set of marker genes is useful for the identification of breast cancer subtypes responsive to taxane based chemotherapy, such as e.g. a taxane-anthracyclinecyclophosphamide-based (e.g. Taxotere (docetaxel)-Adriamycin (doxorubicin)-cyclophosphamide, i.e. (TAC)-based) chemotherapy.

WO 2011/121028 A1 relates to a method or predicting an outcome of cancer in a patient suffering from cancer, said method comprising (a) determining in a biological sample from said patient the expression level of at least one marker gene selected from AKR1C3, MAP4, SPP1, CXCL9, PTGER3, and VEGFC; (b) comparing said expression level to a reference pattern of expression, wherein an increased expression of said at least one marker gene is indicative of said patient having a benefit from microtubule stabilizing agent-based cytotoxic chemotherapy.

US 2011/306513 A1 relates to the elucidation of a gene that can act as a novel marker for liver cancer diagnosis and to diagnostic and prognostic measurements of liver cancer using the same. More specifically, it relates to a diagnosis kit that enables diagnostic and prognostic measurement of a liver cancer using a preparation that measures expression levels of at least one gene selected from a group of liver cancer diagnosis markers consisting of S100P, NK4, CCL20, CSPG2, PLAU, MMP12, ESM-1, ABHD7, HCAPG, CXCL-3, Col5A2, MAGEA, GSN, CDC2, CST1, MELK, ATAD2, FAP and MSN and/or a method for diagnostic and prognostic measurement of liver cancer using the same. These have been discovered using normal liver tissues and liver cancer tissues collected from the same liver cancer patient of the present invention and represent the markers whose accuracy and reliability have been greatly improved as markers of liver cancer. The markers of the present invention can be used for the accurate diagnosis and prognosis of liver cancer.

WO 03/001985 A2 discloses non-invasive methods for detecting, monitoring, staging, and diagnosing malignant melanoma in a skin sample of a subject. The methods include analyzing expression in skin sample of one or more melanoma skin markers. The melanoma skin markers include IL-I RI, endothelin-2, ephrin-A5, IGF Binding Protein 7, HLA-A0202 heavy chain, Activin A (beta A subunit), TNF RII, SPC4, and CNTF R alpha. The skin sample can include nucleic acids, and can be a human skin sample from a lesion suspected of being melanoma.

Yuexin Liu, et al., concludes that a gene signature discovered on a large data set provides robustness in accurately predicting chemotherapy response in serous ovarian carcinoma. The combination of the molecular and morphologic signatures yields a new understanding of potential mechanisms involved in drug resistance (Integrated Analysis of Gene Expression and Tumor Nuclear Image Profiles Associated with Chemotherapy Response in Serous Ovarian Carcinoma, DOI: 10.1371/journal.pone.0036383).

OBJECT OF THE INVENTION

It is an objective of the invention to provide a method for identification of patients, particularly breast cancer patients, who have a benefit from receiving taxanes as a part of their chemotherapy.

It is another object of the present invention to avoid unnecessary side-effects of adjuvant and/or neo-adjuvant taxane-based chemotherapy.

It is another object of the present invention to offer a more robust and specific diagnostic assay system for clinical routine fixed tissue samples to select individualized treatment modalities.

SUMMARY OF THE INVENTION

This disclosure focuses on a predictive test that will help the oncologist to identify patients who will have a benefit from inclusion of taxane in a chemotherapy regimen and thus will help to make decisions on therapeutic regimens. The biomarker and algorithms were identified in an in-vitro sensitivity study.

The present invention relates to a method for predicting a benefit from inclusion of taxane in a chemotherapy regimen in a patient suffering from or at risk of developing recurrent neoplastic disease, in particular breast cancer. Said method comprises the steps of:

a) determining in a tumor sample from said patient the expression levels of the marker genes S100P and PCSK6, and b) mathematically combining the expression level values of the genes PCSK6 and S100P to yield a combined score and comparing said combined score to a reference-value, including a cutoff, wherein a high combined score is indicative of a benefit from including a taxane in a chemotherapy regimen of said patient and a low combined score is indicative of not having a benefit from including a taxane in a chemotherapy regimen of said patient or c) mathematically combining the expression level values of PCSK6 and S100P with the expression values of other genes to yield a combined score and comparing said combined score to a reference-value, including a cutoff, wherein a high combined score is indicative of a benefit from including a taxane in a chemotherapy regimen of said patient and a low combined score is indicative of not having a benefit from including a taxane in a chemotherapy regimen of said patient.

According to an aspect of the invention a high expression level of S100P and PCSK6 generally indicates an increased likelihood of benefit from inclusion of taxane in a chemotherapy regimen.

According to an aspect of the invention there is provided a method as described above, wherein said expression level is determined as an mRNA level.

According to an aspect of the invention there is provided a method as described above, wherein said gene expression level is preferably determined by at least one of the following methods:

a PCR based method,
a micorarray based method,
a hybridization based method,
a sequencing and/or
next generation sequencing approach.

A preferred form is kinetic or quantitative RT-PCR using e.g. commercially available systems such as Taqman, Lightcycler or others.

According to an aspect of the invention there is provided a method as described above, wherein said determination of expression levels is in a formalin-fixed paraffin-embedded tumor sample or in a fresh-frozen tumor sample.

According to an aspect of the invention there is provided a method as described above, wherein the expression level of said at least one marker gene is determined as a pattern of expression relative to at least one reference gene or to a computed average expression value.

According to an aspect of the invention there is provided a method as described above, wherein said step of mathematically combining comprises a step of applying an algorithm to values representative of an expression level of a given gene.

According to an aspect of the invention there is provided a method as described above, wherein said algorithm is a mathematical combination of said values representative of an expression level of a given gene.

According to an aspect of the invention there is provided a method as described above, wherein a value for a representative of an expression level of a given gene is multiplied with a coefficient.

According to an aspect of the invention one, two or more thresholds are determined for said gene expression level or combined score and discriminated into (1) "predicted benefit" and "predicted non-benefit", (2) "predicted benefit" and "predicted adverse effect", (3) "predicted benefit", "predicted indifferent effect" and "predicted adverse effect", or more risk groups with different probabilities of benefit by applying the threshold on the combined score.

According to an aspect of the invention there is provided a method as described above, wherein information regarding clinical parameters of the patient is processed in the step of mathematically combining expression level values for the genes to yield a combined score.

The invention further relates to a kit for performing a method as described above, said kit comprising a set of oligonucleotides capable of specifically binding sequences or to sequences of fragments of the genes: S100P and PCSK6.

The invention further relates to a computer program product capable of processing values representative of an expression level of a combination of genes, mathematically combining said values to yield a combined score, wherein said combined score is predicting said benefit from inclusion of taxane in cytotoxic chemotherapy. The combined score can be transformed to a given scale in an additional step. Said transformation may be linear or non-linear, continuous or discontinuous, bounded or unbounded, monotonic or non-monotonic.

Said computer program product may be stored on a data carrier or implemented on a diagnostic system capable of outputting values representative of an expression level of a given gene, such as a real time PCR system.

If the computer program product is stored on a data carrier or running on a computer, operating personal can input the expression values obtained for the expression level of the respective genes. The computer program product can then apply an algorithm to produce a combined score indicative of a benefit from taxane-based cytotoxic chemotherapy for a given patient.

The methods of the present invention have the advantage of providing a reliable prediction of benefit from the inclusion of taxanes in a cytotoxic chemotherapy regimen based on the use of only a small number of genes.

According to an aspect of the invention said cancer is breast cancer. The marker genes described in this invention are not breast cancer specific genes, but generally cancer-relevant genes or genes relevant to the therapeutic mechanism of microtubule stabilizing drugs. It can therefore be expected that the methods of the invention are also predictive in other cancers, in which taxane-based therapy is commonly administered, such as lung cancer, head-and-neck cancer, ovarian cancer and prostate cancer.

DETAILED DESCRIPTION OF THE INVENTION

Additional details, features, characteristics and advantages of the object of the invention are disclosed in the subclaims, and the following description of the respective figures and examples. However, these drawings should by no means be understood as to limit the scope of the invention.

Figure 1:
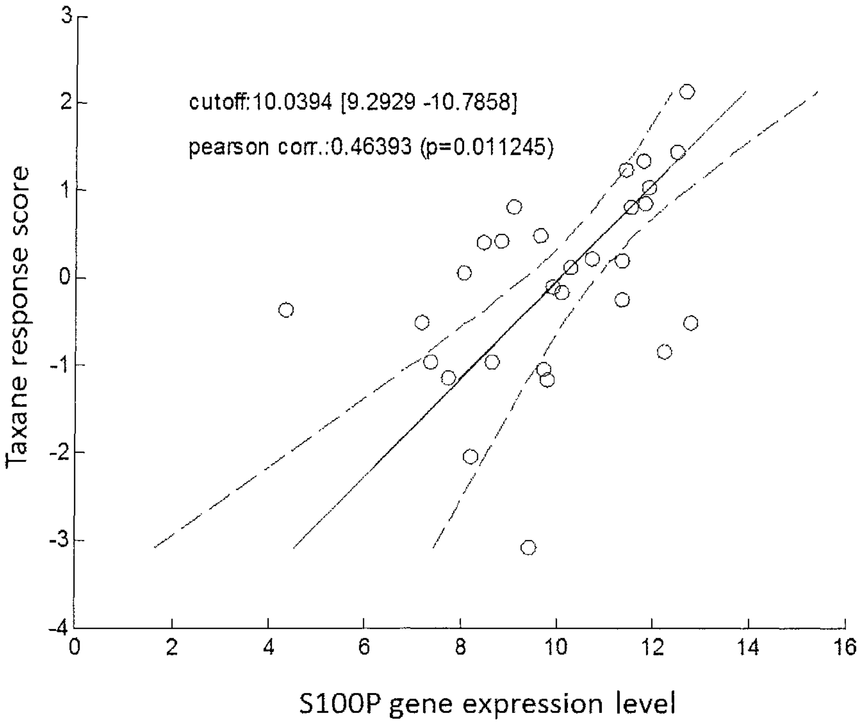
FIG. 1: Correlation between S100P gene expression levels and taxane response scores (derived from the in-vitro chemosensitivity data) in all 29 breast cancer samples. An increased taxane response score is associated with a higher likelihood of a higher benefit from a taxane in comparison to 5-Fluorouracil and/or Epirubicin in breast cancer patients.
Figure 2:
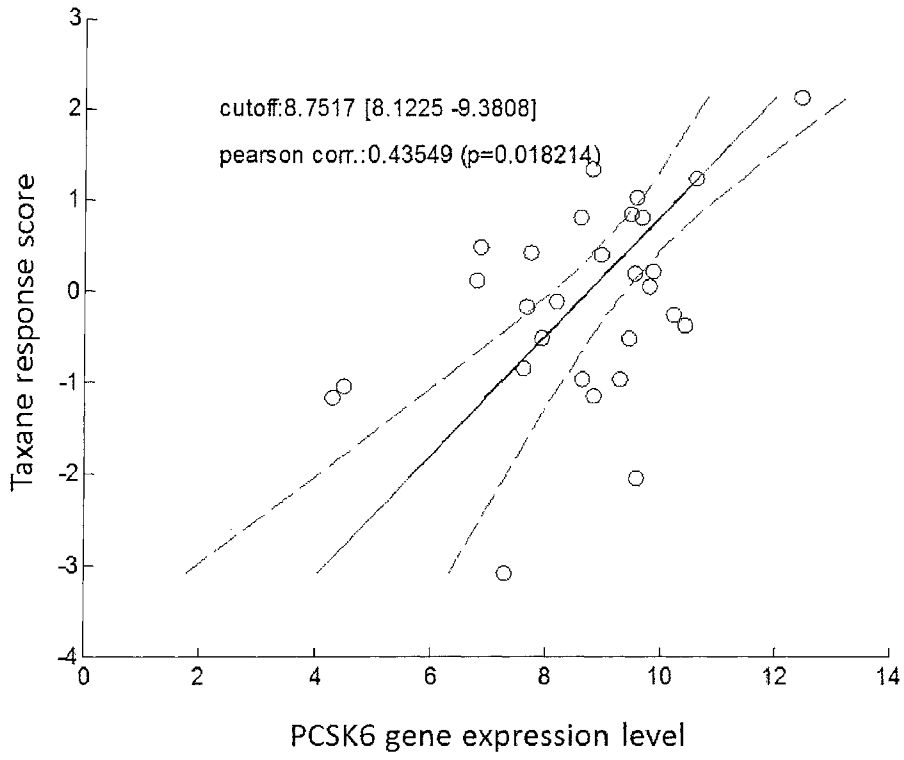
FIG. 2: Correlation between PCSK6 gene expression levels and taxane response scores (derived from the in-vitro chemosensitivity data) in all 29 breast cancer samples. An increased taxane response score is associated with a higher likelihood of a higher benefit from a taxane in comparison to 5-Fluorouracil and/or Epirubicin in breast cancer patients.

The methods of the invention are particularly suited for predicting a benefit from inclusion of taxane in a chemotherapy regimen, preferably in breast cancer patients. Two predictive marker genes (S100P and PCSK6) were identified, whereas a high expression level indicates a benefit from inclusion of taxane in a chemotherapy regimen (FIGS. 1/2).

S100P has been described to be associated with paclitaxel resistance/sensitivity in ovarian cancer cell lines. S100P was overexpressed in stable cell lines derived from ovarian cancer cells and silenced using S100P-targeted siRNA. Both experiments showed that the expression level of S100P contributes to paclitaxel sensitivity (Wang et al., Cancer Lett.; 2008, pp. 277-289; Gao et al., Chin Med 3., 2008, pp. 1563-1568; He et al., Oncol Rep., 2008, pp. 325-332).

Villeneuve and colleagues carried out a microarray screening to compare the gene expression profiles between wild-type and paclitaxel-resistant breast cancer cell lines. Several deregulated genes were identified and S100P was among those genes that showed a decreased expression level in paclitaxel-resistant cell lines. (Villeneuve et al., Breast Cancer Res Treat., 2006, pp. 17-39).

The stated prior art does not necessarily suggest that S100P is a predictive marker for breast cancer patients, since gene expression profiles and resistance mechanisms can be considerably different between cell lines ("in-vitro") and the primary tumor of cancer patients ("in-vivo").

Here, we show for the first time that S100P as well as PCSK6 predict taxane efficacy in breast cancer patients ("in-vivo"). The combination of PCSK6 and S100P gene expression levels improves the predictive performance in comparison to the single markers (PCSK6 or S100P) alone (FIG. 1-4).

Figure 3:
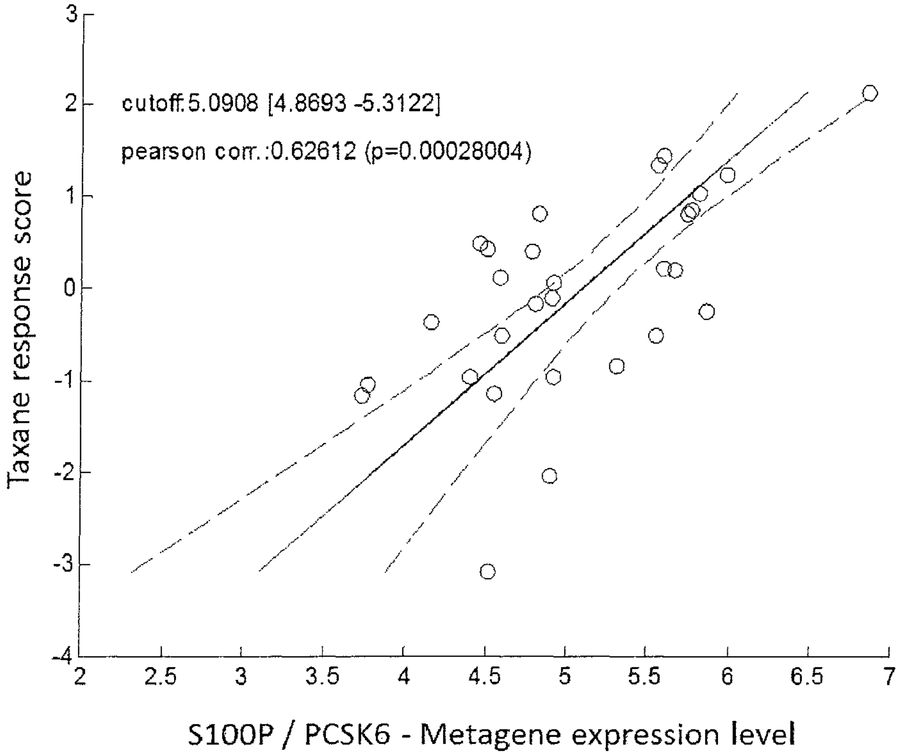
FIG. 3: Correlation between Metagene (mean expression of S100P and PCSK6) RNA levels and taxane response scores (derived from the in-vitro chemosensitivity data) in all 29 breast cancer samples. An increased taxane response score is associated with a higher likelihood of a higher benefit from a taxane in comparison to 5-Fluorouracil and/or Epirubicin in breast cancer patients.
Figure 4:
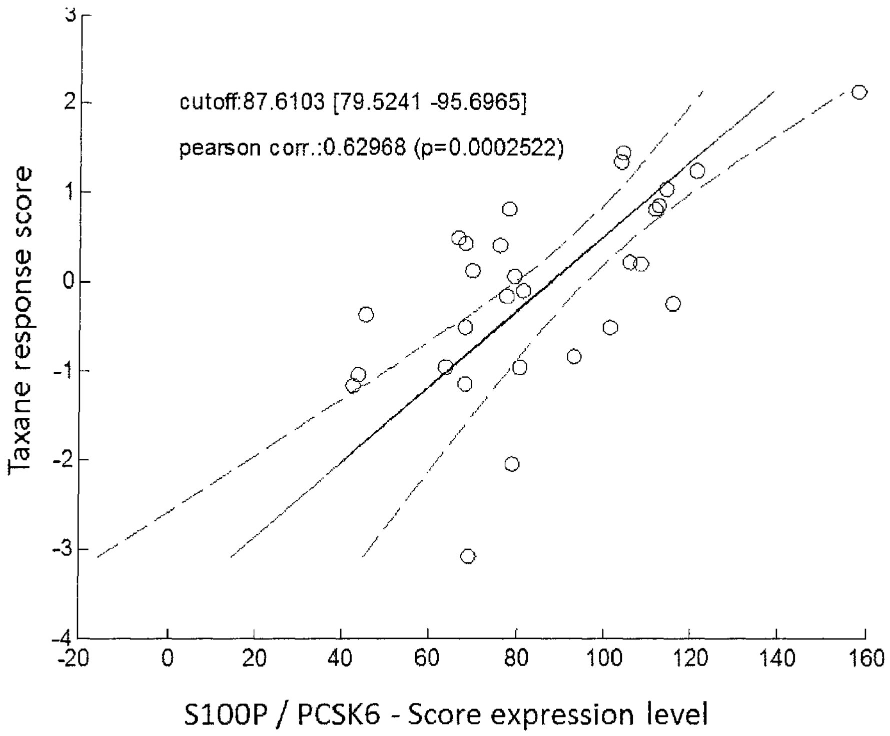
FIG. 4: Correlation between S100P/PCSK6 score (non-linear combination of S100P and PCSK6 expression levels) and taxane response scores (derived from the in-vitro chemosensitivity data) in all 29 breast cancer samples An increased taxane response score is associated with a higher likelihood of a higher benefit from a taxane in comparison to 5-Fluorouracil and/or Epirubicin in breast cancer patients.

Therefore, the invention comprises the expression analysis of both genes of interest, whereas the expression levels are mathematically combined to yield a score, which is predictive for said benefit of a taxane-based cytotoxic chemotherapy (FIGS. 3/4).

The genes and the algorithms were identified in breast cancer patients. RNA was extracted and used for gene expression profiling (Affymetrix HG-U133A microarrays). Microarray cel files were MAS5 normalized with a global scaling procedure and a target intensity of 500. In-vitro chemosensitivity assays were carried out using different cytotoxic agents (e. g. Paclitaxel, 5-Fluorouracil, Epirubicin) to determine the response of a tumor towards a specific agent. The primary tumors were treated with increased concentration of the respective cytotoxic agent. The vitality of the tumor cells was determined using an ATP assay and an area under the dose-response curve (AUC) was determined for every tumor sample and all agents, respectively. An increased AUC indicated a higher sensitivity towards a specific chemotherapeutic agent.

Sensitivity results from the in-vitro chemosensitivity assays were used as the primary endpoint for the assessment of treatment response. The AUC response rates were normalized and the differences between the normalized taxane AUC and the mean AUC of 5-Fluorouracil and Epirubicin were calculated, resulting in a taxane-response score. An increased taxane response score is associated with a higher likelihood of a higher benefit from a taxane in comparison to 5-Fluorouracil and/or Epirubicin in breast cancer patients.

Gene expression levels from the Affymetrix data were correlated to the taxane response score. The expression levels from two genes (S100P/PCSK6) were found to be significantly correlated to the taxane-response score (FIG. 1-4).

Table 1, below, shows Affymetrix probeset ID and TaqMan design ID mapping of the marker genes of the present invention.

| Gene | Design ID | Probeset ID |
|---|---|---|
| S100P | SVD0018 | 204351_at |
| PCSK6 | SVD0016 | 207414_s_at |

Table 2, below, shows full names, Entrez GeneID and chromosomal location of the marker genes of the present invention.

| Official Symbol | Official Full Name | Entrez | Location |
|---|---|---|---|
| S100P | S100 calcium binding protein P | 6286 | 4p16 |
| PCSK6 | proprotein convertase subtilisin/kexin type 6 | 5046 | 15q26.3 |

Figure 5:
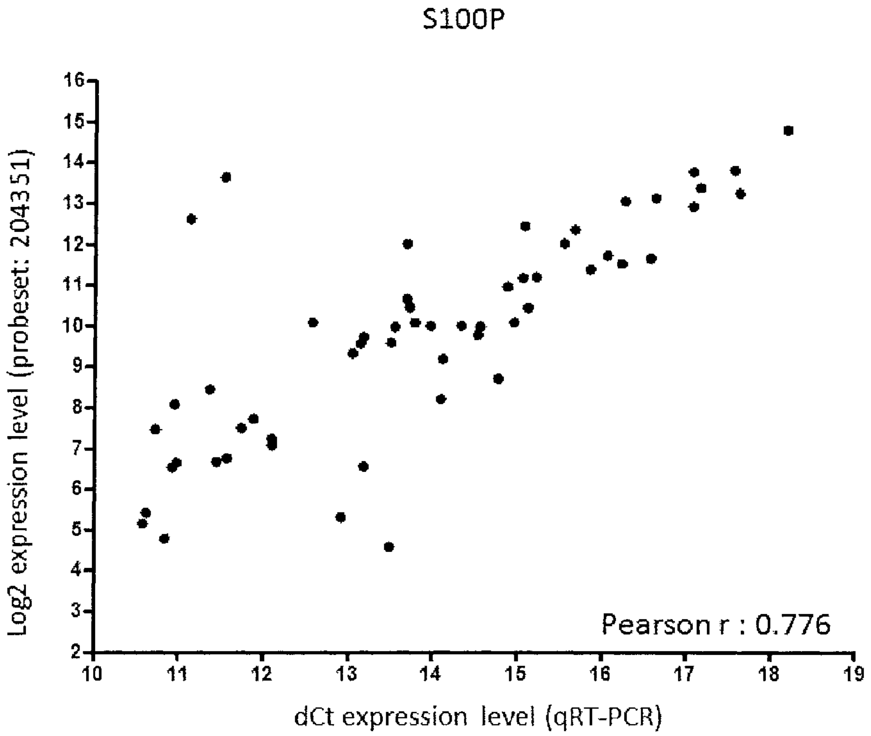
FIG. 5: Platform transfer—S100P: The results from the Affymetrix data (log 2 expression data) in fresh-frozen tumor samples were transferred to a diagnostic platform (qRT-PCR, dCt level) and formalin-fixed paraffin-embedded tissue using 56 paired technical samples.
Figure 6:
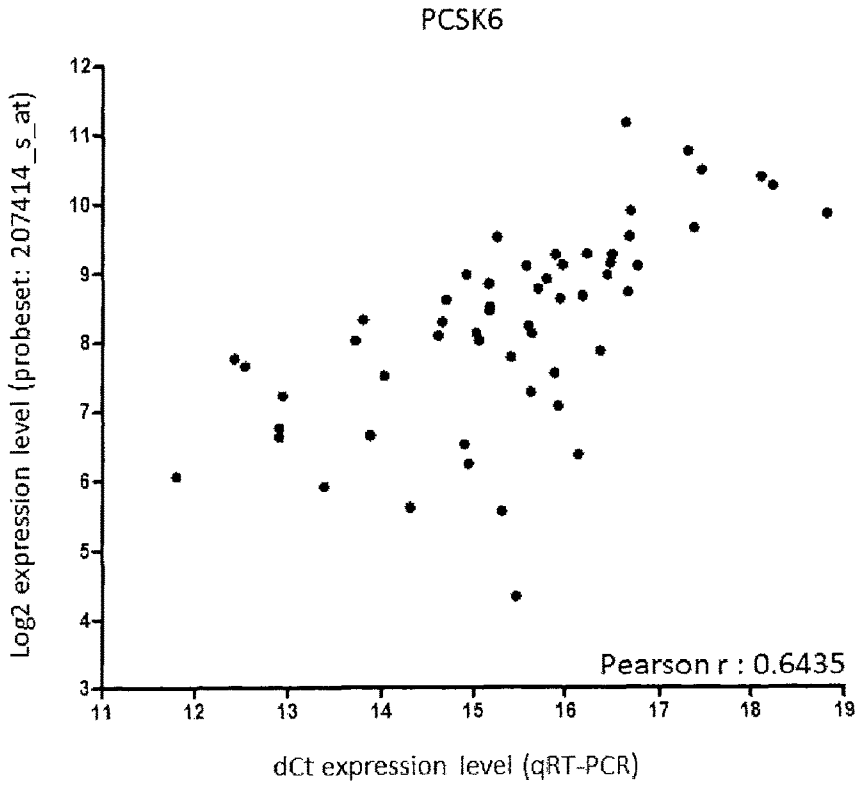
FIG. 6: Platform transfer—PCSK6: The results from the Affymetrix data (log 2 expression data) in fresh-frozen tumor samples were transferred to a diagnostic platform (qRT-PCR, dCt level) and formalin-fixed paraffin-embedded tissue using 56 paired technical samples.

The results from the Affymetrix data in fresh-frozen tumor samples were transferred to a diagnostic platform (qRT-PCR) and formalin-fixed paraffin-embedded tissue using 56 paired technical samples. The platform transfer was done using Affymetrix microarray data (fresh-frozen tumor samples) and qRT-PCR expression data (FFPE samples) from the same technical samples (FIG. 5/6).

TABLE 3 qRT-PCR primer and probe sequences

| Seq Id | Gene symbol | Primer-ID | Probe |
|---|---|---|---|
| 1 | S100P | SVD0018 | CTGCAATCACGTCTGCCTGTCACAAGT |
| 2 | PCSK6 | SVD0016 | CTGCTCCCCTGTTTGACGACAGTGC |

| Seq Id | Gene symbol | Primer-ID | Forward Primer |
|---|---|---|---|
| 1 | S100P | SVD0018 | TTCAGTGAGTTCATCGTGTTCGT |
| 2 | PCSK6 | SVD0016 | TTTCGACCTCGTCTTTCTCCAT |

TABLE 3-continued

| qRT-PCR primer and probe sequences | | | |
|---|---|---|---|
| Seq Id | Gene symbol | Primer-ID | Reverse Primer |
| 1 | S100P | SVD0018 | CATCATTTGAGTCCTGCCTTCTC |
| 2 | PCSK6 | SVD0016 | TCTCTCCAGCTCACAGGTGACA |

Herein disclosed are unique combinations of two marker genes which can be combined into an algorithm for the here presented new predictive test. Technically, the method of the invention can be practiced using two technologies: 1.) Isolation of total RNA from fresh or fixed tumor tissue and 2.) Quantitative RT-PCR of the isolated nucleic acids. Alternatively, it is contemplated to measure expression levels using alternative technologies, including but not limited to microarray, in particular Affymetrix U-133A arrays, sequencing or by measurement at a protein level.

The methods of the invention are based on quantitative determination of RNA species isolated from the tumor in order to obtain expression values and subsequent bioinformatics analysis of said determined expression values. RNA species can be isolated from any type of tumor sample, e.g. biopsy samples, smear samples, resected tumor material, fresh frozen tumor tissue or from paraffin embedded and formalin fixed tumor tissue. First, RNA levels of genes coding for the genes S100P and PSCK6 are determined. Based on these expression values a predictive score is calculated by a mathematical combination, e.g. a linear or non-linear combination (FIGS. 3/4). A high score indicates an increased likelihood of a benefit from inclusion of taxane in a chemotherapy regimen, whereas a low score value indicates a decreased likelihood.

What is claimed is:

1. A method for treating a patient suffering from or at risk of developing breast cancer, the method comprising:

a) obtaining a specimen from the patient wherein the specimen comprises a cancer cell;

b) determining expression level values of the genes proprotein convertase subtilisin/kexin type 6 (PCSK6) and S100 calcium binding protein P (S100P), c) combining the expression level values of PCSK6 and S100P to yield a combined score and comparing said combined score to a reference-value, including a cutoff; and d) administering a chemotherapy regimen with an effective amount of taxane to said patent if said combined score is greater than said reference-value or administering a chemotherapy regimen without an effective amount of taxane to said patient if said combined score is equal to or less than said reference-value.

2. The method of claim 1, wherein said expression level is determined as a non-protein such as a gene expression level.

3. The method or claim 1, wherein said expression level is determined by at least one of the following methods:

a PCR based method, a microarray based method, a hybridization based method, a sequencing and/or next generation sequencing approach.

4. The method of claim 1, wherein said determination of expression levels is in a formalin-fixed paraffin-embedded tumor sample or in a fresh-frozen tumor sample.

5. The method claim 1, wherein the expression levels are determined as a pattern of expression relative to at least one reference gene or to a computed average expression value.

6. The method of claim 1, wherein said step of combining the expression level values comprises a step of applying an algorithm to values representative of an expression level of S100P and PCSK6.

7. The method of claim 6, wherein said algorithm is a linear combination of said values representative of an expression level of S100P and PCSK6.

8. The method of claim 6, wherein a value for a representative of an expression level of S100P and PCSK6 is multiplied with a coefficient.

9. The method of claim 1, wherein one, two or more thresholds are determined for said combined score and discriminated groups indicative of having a benefit or not having a benefit of adding taxane, by applying the threshold on the combined score.

10. The method of claim 1, wherein tumor size, lymph node status, or tumor grading of the patient is included in the step of combining expression level values for the genes to yield a combined score.

* * * * *

SEQUENCE LISTING

<160> NUMBER OF SEQ ID NOS: 8

<210> SEQ ID NO 1
<211> LENGTH: 27
<212> TYPE: DNA
<213> ORGANISM: Homo sapiens

<400> SEQUENCE: 1
ctgcaatcac gtctgcctgt cacaagt 27

<210> SEQ ID NO 2
<211> LENGTH: 23
<212> TYPE: DNA
<213> ORGANISM: Homo sapiens

<400> SEQUENCE: 2
ttcagtgagt tcatcgtgtt cgt 23

<210> SEQ ID NO 3
<211> LENGTH: 23
<212> TYPE: DNA
<213> ORGANISM: Homo sapiens

<400> SEQUENCE: 3
catcatttga gtcctgcctt ctc 23

<210> SEQ ID NO 4
<211> LENGTH: 25
<212> TYPE: DNA
<213> ORGANISM: Homo sapiens

<400> SEQUENCE: 4
ctgctcccct gtttgacgac agtgc 25

<210> SEQ ID NO 5
<211> LENGTH: 22
<212> TYPE: DNA
<213> ORGANISM: Homo sapiens

<400> SEQUENCE: 5
tttcgacctc gtctttctcc at 22

<210> SEQ ID NO 6
<211> LENGTH: 22
<212> TYPE: DNA

<213> ORGANISM: Homo sapiens

<400> SEQUENCE: 6
tctctccagc tcacaggtga ca 22

<210> SEQ ID NO 7
<211> LENGTH: 3332
<212> TYPE: DNA
<213> ORGANISM: Homo sapiens

<400> SEQUENCE: 7
tgaggctgcc ttataaagca ccaagaggct gccagtggga cattttctcg gccctgccag 60
cccccaggag gaaggtgggt ctgaatctag caccatgacg gaactagaga cagccatggg 120
catgatcata gacgtctttt cccgatattc gggcagcgag ggcagcacgc agaccctgac 180
caagggggag ctcaaggtgc tgatggagaa ggagctacca ggcttcctgc aggtgagcca 240
ggccggcagt gctggactca gcgggggctg gggaagaagg ggaaggcgtg gcaggcagag 300
ggctgagagc tgcggtgggg tcggcggtca aggggctcag aggcaagagg gacagatcct 360
gaaatgccct ggaagcccag ccaaggaacg gacccaccct ggcataaagg caggggaggc 420
gggagcatct gagcagggag agggtgtggt cagcttgatc cttgaaacat ggggttgacc 480
ccagtgtatt tgtgacaggc ctggtgggag agtgggactc aaacctgtgc agtgggggca 540
ggggcggaat gcaatccagg gctgccattt gcaagtttgc caagcttgcc aagcccttga 600
gccctcgggg ctgtcctcca aggctgccgg ccataaacgc cccagctctg cctcccactt 660
gcccgctttc cctgctccca ttcccaggcc ccttgttgcc tggtattagt gggtctggca 720
ggaaggacgg gaggaggctc catcctggca cctgtctgcg cagagctgtg gacctccctt 780
gggctccctg ccagggagga gccaccggcc tgagcctcac agaaggcccc tcagggcggc 840
caggaccagc ttccttccgc ccggggcagc ctccggctgg gctgaacaga agccgtaccc 900
tctccatttc cccttccctt tgacccctgt cctctccttc tttctcactc ccccactttc 960
ttccttcctt cccctcccct tcgggcccca ccagactctg cctacctgct aaggggctaa 1020
cccacataga tgctgataat caaaaatgaa agcctgaaat tttcagccct agaatcactt 1080
caaagacatg aaacacttca gaatattgct tctattttct tttcttttct tttttttttt 1140
ttttgagaca agatgtcact ctgtcaccca ggctggagtg cagtggcagg atcacggctc 1200
actgcagcct cgacctccct gggctcaggt gatcctccca cctcagccta ccgagtagct 1260
gggactacag gtgcatgtca ccatacccgg ttaatttttg tatttttttt agagacaagg 1320
tctcaccatg ttgcccaggc tggtctcaaa ctcctgtgct caggcaatgc gtcagcctcg 1380
acatctcaaa gtgctgtgat tacaggcgtg agccccgaca cctggcctag ttctattttc 1440
taaatgtgaa ttctgtaaag atatctttta aaaataaagt tctgtttttg gtagaaaatg 1500
taaaaataga taaatatgga gggaagaaat ccccccctgga atacagacgc ttcctctccc 1560
ttccagcctt ttccccatat gaacattgct gtgagtgaga tttacatgca atgtaatttc 1620
tttttgagct taacattaca acataaattc tcaaactctg atgttcatta aacaccccag 1680
ccccatcctg ggaacttggg cttggggctc ggggtgttct gataatgatc aaagtatgag 1740
aattgaaccc atgaggactt tgatccaaga tactggggtg tggggagggg caggcacagg 1800
tgtcctggga acacactttg agaagcaatg gcaaagctgg gggtccagct aatgtgttac 1860
attagaatca cctcggggag gccctgggtg cccttctcag ccctccctcc ggaggctgct 1920
gaagcccagc aaagccggag tcagagaaca atgtccgcct gagggcaggg ctgggctggg 1980
ctggccttct ggccctatct gctccgtgcc caacccagcg ccccgcacag tcggagcttt 2040
gtaaatacga ggtgactgtc tgcctacaaa ctttgtaaac atcacttgaa atggccgcag 2100
ggtattgtga catggccata ccactatttg tttgctattg aatttgtact tccctgcctt 2160
acttttgcta ttgcaaacca tgctgtcact aaggtcttca tgcacacagt tgtgtcttgg 2220
tcagatgata tgtttctacc aattttaatt gtgtttcttt ccacctggac acacagctct 2280
ctggcccagg gctgggtcat cagcacaccc tgctgctgct gttcagatct gcatcctggt 2340
cccgcttggt cccacagtga gaacgctttg ctatcacatg ggcaggctct gagagccctg 2400
ccggcctggc cttctcaaag aagacctgag agcttgggac ccaagcagag aggaagaaca 2460
gggctcaggg tgcttgctcc atgctcgctc cacacctggg gctcaaccct ggctttcccc 2520
ggctccctgt gtgacttcag ggcaggtccc ttgggccctc tgggccttat catcttcatc 2580
tgtaacaggg cgatgcctct gccgtgtctg gtggtgttga ggagttcctg tttgtgtaag 2640
cagctagttc agtgccagca cgagatggga ggcccatgaa gttagcagtg cacaaaaaat 2700
agagcaaaga ctggatgcat ttcctgagaa caaccatcac tgtaaagcac tttacaaatc 2760
caaagacaac ccccggcaaa aactcaaaat gaaactccct ctcgcagagc acaattccaa 2820
ttcgctctaa aaacattaca agttagttca tgtcatgcca gatagctgaa ggcagctcac 2880
aagttcttaa ggccaggaat gccatgtgtc tgctatgcac agctggccct ggccctgaca 2940
gcaaaggtga cgcagatgtg ggtgccctgc tcctgcccag cagcagtgct tggtggaggc 3000
tgaggccctg cacaggcacc ctcactgctg accttgagcc tctctctcct ctagagtgga 3060
aaagacaagg atgccgtgga taaattgctc aaggacctgg atgccaatgg agatgcccag 3120
gtggacttca gtgagttcat agtgttcgtg gctgcaatca cgtctgcctg tcacaagtac 3180
tttgagaagg caggactcaa atgatgccct ggagatgtca cagattcctg gcagagccat 3240
ggtcccaggc ttcccaaaag tgtttgttgg caattattcc cctaggctga gcctgctcat 3300
gtacctctga ttaataaatg cttatgaaat ga 3332

<210> SEQ ID NO 8
<211> LENGTH: 186055
<212> TYPE: DNA
<213> ORGANISM: Homo sapiens

<400> SEQUENCE: 8
tcgcgggccg aggacgcctc tggggcggca ccgcgtcccg agagccccag aagtcggcgg 60
ggaagttccc ccggtggggg gcgtttcggg cctcccggac ggctctcggc cccggagccc 120
ggtcgcagga gcgcgggccc gggggcggga acgcgccgcg gccgcctcct cctccccggc 180
tcccgcccgc ggcggtgttg gcggcggcgg tggcggcggc ggcggcgctt ccccggcgcg 240
gagcggcttt aaaaggcggc actccacccc ccggcgcact cgcagctcgg gcgccgcgcg 300
agcctgtcgc cgctatgcct ccgcgcgcgc cgcctgcgcc cgggccccgg ccgccgcccc 360
gggccgccgc cgccaccgac accgccgcgg gcgcgggggg cgcggggggc gcgggggcg 420 ccggcgggcc cgggttccgg ccgctcgcgc cgcgtccctg gcgctggctg ctgctgctgg 480
cgctgcctgc cgcctgctcc gcccccgccg cgccccgtct acaccaacca ctgggcggtg 540
caagtgctgg gcggcccggc cgaggcggac cgcgtggcgg cggcgcacgg gtacctcaac 600
ttgggccagg tgagtgcggc cggccccgcg cgcccaaaac tttcccggcg gcctccggcg 660
cgcgcgaggg gggcgcctcc gcagtcctgt ccgcccggcc ccggccccgc gcgcgcgtgg 720

-continued

```
gaaggctccg ggaccgcttg gggacggcgg gcggccgggg cgccctgcgg ggggggggtgt    780
cgcccggggg ggcgcgcgcg ggacactcgg cggggtgggg gggactgggg tcccgcgtgg    840
gcgcccacgc aggtccggcg cgccgaccgc aagtcccccg gcagtgccgc ccaaccccgc    900
gctcggaagt gtggcctcag aagccggggc ggcgcggaca cctgccgggc tccgggggag    960
tctgggctgc ctcaggcgtc gcgcgccgtc cgccgctggg tcctgggcgc ccacccggct   1020
ctcccccgcg ggggagcggc ccctctgccc tcgacgggcg gcgcgagctc cggacccggt   1080
gcgcgcgcca aggcggccgc ggccgctgct tgggtgacat gagcgtggcc cggcgtctcg   1140
gggactcgcg ctccctcggt gtccgcggct cccgggggta gatggccggg agcctgcacc   1200
ctggagcccg gccgccgtcg gagaggcctt gggacagcgc agggccgggg gtcctgggtt   1260
taaaacctct ccaggagcgg agggagggcg ctttgtgtgg gggcttctgc cgcggttctg   1320
atggccgagc ggtgtgacct ttggcaagtc gctcccctga caagctcctt tgcagtcagt   1380
ggcaatgtct acaccgctgg gttgtcggaa agatctaatg ctgcgttgcc acagagcctg   1440
gaccggggcc tgaccctcac cggcccccac ggggccctcc cagccccgca gccctcggct   1500
gtcccctctt ctgtcagtga gcaagcaggc cacgccctgg gcacaaaggc ggcattaccc   1560
tcaaaggacc tcccggcggg tcccttttc ctctctcaac cagctaccgg gctgaggggc   1620
ggtgagttgg ggttgatcca tgtttatggc tcctggagag gccgttattt tgaggtcaca   1680
ccaggggacc tctcagtgca gttaacaaat ctacaaacta cacactcaga gggttaagtg   1740
aagtgacagg gaagcaccga ctcataactc taaaccttag tgccaggcag tgttaaatgt   1800
agtttcatcg ttatccgtgg cagaagccag caaggtgtgg tggcgtccct gattgataga   1860
aatgacatta gttctgcatc ccaagcccca cgttgatgta ctattaggtg tgtggctgga   1920
ggggtggatt ccaccattcg aatgaaggaa tcttcacaag gcaggttcga gtttactgaa   1980
agaatgctag cacatctttg gagacctttt aaatatatgc atatatatat ataaaatgtt   2040
acatatatac acatatacac acatacatat acgcacatgt atatccatat agatatttag   2100
tttttttaac cactcaaggc cctccaaaca tcctgtgatt tcagattttg ccgtcgggta   2160
gcactgactt cgtttgtctc tgtagttctt gactctccct ggctgattgt ccaggctgaa   2220
gaaggtgttc ctcatgtttg cgtagtgccc ctggctcctg ccacacttcg ctgctgtgcc   2280
caggtggccc agcaatttgt cttcagctaa aagtgactct taaactacgc gataaattac   2340
aaagtgcctg ggttttggga ttctaaaatt aaatgagcag aatggagctg aaattgagct   2400
gtgagctcac actgcaagag agaggcagag aggcacaggt aactctcccc ggaaatttct   2460
atctgtggga ataaaaatgc ctaacccttg gccatgccgc ccctttgaga caacctctgt   2520
caggctcact gagttcttag tgcagtctgc tctcctggtt ttgcggatgg gagagaagat   2580
tcgccccgat gcacactccg tacccaggat attctgggga gttaatcggg gtctccccag   2640
ctctgtctag tgcagccagc atgaatgcca cgcagcccgg tcactcaggc atggtgctgg   2700
cagtggcact gcggtgacat tcactaacag agattagctg gttggggata ggagctgtct   2760
cagaggcttg tgtgtgatta ctcacggagg gcctattact ctttattcca aaacgagctt   2820
ttctttcccc cctctaagtg cactgctaat gtggaaaagg cctggagcat ttgagcctct   2880
acccactcaa taagaactct ttgaaaacct tatttgcctt tttttcagcc aggagaattt   2940
gtgactcata aataagatgt agatattatt agctttgact tacagatgag taaatggggg   3000
tgaagtaagg gaaggaagct gtttgtgttc acatggtacg catatgtcac ctctgacagt   3060
tccatccctg ctcatttgct tctgccgtat tctctgttct gaggtctcct ttgtgaaact   3120
```

-continued

```
ctttctccaa gcccttaatg ggcaattagt gttatgttct gtacttgcct gaatcgcagc   3180
cctggttttc tcccagatag tcgctgtgct caaggttctt gcttgtttta ctttcttcca   3240
tacaactaat aactggattc agtttatttc acatggccca gaggtaattt agactggtgg   3300
ttattcacct ttcttgtgtc atggctccct ttcagcacct gataaaggct gtggatcctc   3360
tccattgtaa aatatgcatc accagggaca agacaagaca gcctctcttt gtccctctac   3420
tcatcagtcc aggtaacacc acaggatttc aaagggaata aaaatgtgga agtgtccaat   3480
gtcattatcg gcagatgaca taactacatg gataatccaa aagagcctgg agattaaccc   3540
ctggagctaa taagggagtt gatcagcaac agccacctgc atggcagcac atctgagaag   3600
acgaaagaaa ccattcttca ttcttgcata aaagctgtta gatacgttga aataggtctt   3660
ttaaaaaggt gagactttta tagagaaaca taaaatattt agaagaagga ctgagaaaag   3720
aaagtttagg ctgggcatgg tggctcatcc cagcactttg ggaggctgag gcaggcggat   3780
cacctgaggt caggagttcg agaccagcca gaccaacatg gagaaaccct gtctctacta   3840
aaaatacaaa aattagctgg gcttggtgac acatgccggt aatcccagct acttgggagg   3900
ttgaggcagg aaaatagctt gaacctggga ggcggaggtt gcagtgaacc gagaccgcac   3960
cattgcactc cagcctgggc gacaagagtg aaactccgtc tcaaaaaaaa aaaaaaaaaa   4020
aaaaatttaa ataaatggag agatgcgttg tgttcatgca tgggagggct ggctctcata   4080
gttgccccaa tttaatctgc aaattcaatg taatctagtt taagctgtga caagatttaa   4140
tgtggaatat gaaatcacac aaatgaatta taaaattcat atggaagagt aaggtccagg   4200
aatacctcag acaactctgg gaaagaagag gaggagggga gttgtggtaa cgacagtcca   4260
gcagtagagt caactcaaac ccaagcatgt gtgggaactt gtatgtgtga gctgaagagt   4320
tacaaataga tggggaagga tggctattt actaaatggt gctgggagaa caggctctcc   4380
ccatggaaaa acaattagat cctcacatta cacaacagta cattccagat gggattaaag   4440
actgtatata aaactttaga aagagctgca gtggaatacc tttgtcacac cgggaaagga   4500
gtccctacac aagttatgaa aataaatttc aaaatgaaga gactgataca ttaagataaa   4560
aattctatgt aaacaaaggc atcctaacag agttaaaaag caagaataga ccaggaaagt   4620
atttacaata tataacaaat acattagtac acagattatt ttgaaaacta taaatcacta   4680
agaaaaaaag atacacgcca ggtagaaaaa tggggaagtt tatgaatgga gaagtcaatg   4740
aagagaaatc caaatgacca gtaaacataa gaaatgatgc ccagcttcac tcaagttcgc   4800
tgggggttat tggagcactg caatttaggc aacgatgaga taccatttca cacctattgg   4860
atttcccgac acggaagagt gttagcatca cgtgctggca aggatataga gcaatgggaa   4920
ctttcagatg ctgctggtgg agattggtat cgtttggaga gcaatttggc gatacacggt   4980
gaggctggac ttgctagtcc acagccagac atatcctgga agaactctcc cacgtgtgca   5040
caaagagact tgtataagaa tgtccatgca ggcgtttttt taaatgaagg aaaacccacc   5100
ttccctgaag tagaatagag aactaaatca aaatagtcac accatgcaag actctacagt   5160
ggttagaaat gaataaacca gatctatatc tacacagata catctctcaa atagtgttga   5220
gagagaaaaa aggcaaattg taggtgtcca atgtgatcat attcatgtaa acgttaagaa   5280
acacacaaag caggccgggc gtggtggctc acgcctgtaa tcccagcact ttgggaggca   5340
gaggcgggtg gatcatctga ggtcaggagt tcgagaccag cctggccaac atggtgaaac   5400
cctgtctcta ctaaaaaaat atgaaaatta gctgggcgtg gtggtgcacg cctgtaatgc   5460
```

-continued

```
cagctactca ggaggctgag gcaggagaat ggcttgaacc tgggaggtgg aggttgcagt   5520
gagctgagat gaacaggact gcactccagt ctggccgacg agtagagtga aactctgtct   5580
caaaacaaaa acaaaaacaa gcaaaaacaa agcacaaagc aatactgtat taattatgga   5640
tgcttataga tgtagtaaaa gtataaaagt gtgggctgta aggatctgca tcaaattcta   5700
gttagcaatg acctccaaga agggagggag gggagaggaa cttcaaactt tatctgcagt   5760
gtactgcttt acaacacacg cttatgtgtg tgggtgtgtg tatgtataaa catacgtgga   5820
ttatatacaa aattgtgcct agacattttg tacttttttt ctttgtatca gggtatatta   5880
catgtggtga tgtgtacaag tgtgtatata tacacacgta taatatataa acacacgtat   5940
attgacgcat atacctatat acatagacat atacacagat acacataaaa cattgaagag   6000
agaaaaaaga aaagggagat gcacatggta cacctaccgc atggtgcttc tggaccatct   6060
gaagcccacc gctggaggca ggtgcctgca ggcccatgtt aagaagtccc tactttagat   6120
gtccagactg ggccgatcca cttgtcaagg aaatggtgac agagaaacag aatgtctggc   6180
tgcaggtcgc atgggcgttt ggacagagct ggacacggag cccaggaacc cttcccttct   6240
cccctgcttc tttctccttc cagtcaccct cgctctaacc tgtgtgcatt gtcacctttg   6300
acattgtgac tcagaaaaga caagttgctt gtgtggagag gatggcagca aggtattctc   6360
cacataccaa atcacaacag ctcagcgtct gctgctcttg gaaatgatgt ttatcttaag   6420
ggtggttctt ggatgccatg ctttcccttg ggtttttgct ttgcctgggg tattgagcta   6480
atttgttgct tctgagtctg aacataaaaa ggcaggctgg ctgccagggc cctaaaagat   6540
ctaagagcct taaatgatct tgaacttgcc ttaaatagtt ttacttaaaa tagctactga   6600
gcaggacata cctggcccag aatttcaggt gagcctgcac gattcatttg tcagcagagg   6660
aaaattgtca tgctgcagac aacttgttct tgcaatgaaa aacaagccga agccttaacc   6720
aggtgttaaa atgatgggcc agaacttgtt ccagccacag cgtcaggggt ttggtaggga   6780
caaggggaga cccggaagag cagtcacctg tgacctagtt ctctgggatt ggttttcggt   6840
ctaaggctgt cttggtttta tgctctgagc caagctggac tggctgtgcg cggctggcct   6900
gcgagaggtt ctgggtgtga actgagggac agaggcaaga tgagggttgt gaagctcatt   6960
gtcttaaccc tcctatctga cgtcttcacc cggatggtga tgcctttaag tgggcaggag   7020
tttaattgac cggactgccc tcctgagtca ttggagctgg tgcggggagt ggtgatcaaa   7080
gccgagccag ctgccatctc tggagccaga aaagctccag aaggcagcat ccagggcaga   7140
ctcagaatca ggactgagca ggtgcagggg cagactcaga atcaggagca gactcagaat   7200
caggactgag caggtggctc agctgactgg accattagaa aggcttgagt ttctctgggc   7260
ggaaaccagg gaagcaaatg agaaacacgg agctgtcgat gggctggggg aggctgggac   7320
accgcctgat actcctgccg gctttgagct ttgggtggtg acagggacac tcagggctgt   7380
ccagaccctg ttctccagtg tccgccaact gcatgccggc tgggaacgtc ctgagctttt   7440
ttggatctct gagcctctac acagattgtg gcatctagaa agtagttcct ctgatcttct   7500
gcagctcagc caggctgccg acacctctcc tcctcctttc accctgccct gggagggctt   7560
ccgggttgta cttgccctgg gtggctggcc tcctcctggc tcctgggact gggtcttggc   7620
cttgccaccg accagaagcc ctggtcttgc tcccaccagc tgatgtttct cctgactatt   7680
gctccgaagg ccctcaccag ccctgcaggg aggtgtcacc aggcctggtt aatggtgatg   7740
aggccttaga cccaggtacc ttctgacaaa ccagtgactg acaggccagg gccggacccc   7800
acaccctctg actcaccttc tactgctgtc acctcgtacc tgcttcccag acaaaggtaa   7860
```

```
atcatcagac agaaaagcct ttcggcttct gccagaatga acagacaaga ggcatagcaa   7920
cctccggaga ccccaccagc cgccgtttct ccctctgtcc accgggtgcg tgcacatgcg   7980
tgtgcgtgaa cgcgcacaga ctcaaagggc tgcacaccag catggctctg tctcggggaa   8040
tctgtactgg ctcctgctca tcagcattgg aaccactcac acctctctct attggaggga   8100
aaaagaaaag ccctccagtc cttctaggaa gccactcaaa ctacacattt gagtcactca   8160
catttcagtc actcaagctg cacatttatc agctggacta atcatctttt gctgaaacct   8220
cctcctcgtg tgggtccctg tctacaagaa gagacccctg tctaccttag tggcagagct   8280
ggaggcctag aggtcaccat cgcctcctcc tgctcccgtg ctcccccaag cctgtctcac   8340
tgtctcctga atggctctca ggctccctgc attgcccctg ccaccgccca gcacaggctg   8400
tggcctctgt ggcctctacc tgcctcaggg cctcctcctg ccccacccca ccgcctcgag   8460
ccctggctgt agctgcagct ctgcccatcc cccatcttca tgcttttgct tcctttcagg   8520
ctttgcttct gttgttcttc ctgcccagaa cggctttacc tgtcaccagg ttcgcccctc   8580
agccttccca cccgtcacca ggttcgcccc tcagccttcc cacccgtcac caggttcgcc   8640
cctcagcctt cccacccgtc accagattcg cccctcagcc ttccaagttc tgctgcactg   8700
tcagttccat cagccgactc accccgattt ccccagcccg ccggatgtac ccttcgtctg   8760
ggcccccagg ccccctgcca cctggacgtt gcctgctggc ttgcctgttt ctgacactgg   8820
gctctgggct tcctgggtga gtcagcccaa agttaggcct ctggctgctc tctaaggtta   8880
gttccgattc tgccacctct gtggtggccg gcagacgtgc gttcatttat tcagcgagta   8940
ttgctgtgtg ctctcactgg cctgggcact tagagataag aaaatgtggc cctgccttg    9000
caagagtctt aagagactct tggttatgag tctttgtgag ggaccaaggc caggcacctg   9060
cgctttgttt aagtgtcatt tattgaacca cccccaccat cgctttctca tcccaatcgt   9120
ttgctttttg gagtcactcg ataggccctg ccacgtacgt acttgtacat gaggacaccc   9180
tctttgtgat gctgtagttt gcctcttggc caggtcagct ccacactgat ctgagagccc   9240
tgtgtcccct gaaggcccca ctagtgccct ggaggcccca ctggtgccct ggagctcact   9300
gtggatgctt cacaccctgc gggtcccatc atcccatcaa gctgtggttt ttcctgatgt   9360
ccttgtgcct ctgccctttg agcatctgga ggacccagca gcaggcgcaa ggccccctgt   9420
ctagtcctgc aaggaagggg gatgaatagc catcagctgt caggagcctc acgctccatg   9480
ggatgggatc agcagcctag ggttcccatg gcaaccagcc catcaatgcc ctcagtgtca   9540
agacaggggc accgtggaaa ggaagaaagt ctcattgtct tgccttggct gcttgggcat   9600
aaacaagctg cgctccacag ggccccgcag ccacgcccga cctgtggctc tgcccagccg   9660
cacatggacc catttactga attgggctgg gaagaggctg tcactgttag ttctctaatc   9720
ttcctcgggg gctcttgtat ttctgccacc ggccagcatc catcacttct agagtccttg   9780
ttgggaaaat ccatcttctc agtgagagtg ggcagaaaca gcccaaatgg agcagactac   9840
cgaagctctg agtgatcagc cagaccgccc tggggggaat ccatcagtgg gtaatggcat   9900
cactcacgtt cctgcaagga acctggactt ccagactttc ccgctttggt ttcaaacacc   9960
ctgatgacaa ctctcagaca tatctcctgt gatcatttaa gcagatcacc ttgagatgac  10020
cactgctggg cttgccacag gcggacagtc taagaaggtc ctgtcccccct tcctggactg 10080
tccccctggg aggaccccag cagtggtcac ttacaagagc ttccttcttg ccttcaaaag  10140
gcccaagttc acctccctga tcattgccgg actcttccct gggtggagat ctgggaaggt  10200
```

-continued

```
ggtggagggg aagggagggg ctgcctcgtg ttggataagg gccctcccac cagaggtcag  10260
gcctgctgtt ccctgtctag tagaaggctg catggaggtg ctcctgtgcc ccacaccgtt  10320
ctgctcacct atcttgtacc ccgtcctcca gatgggaaac cagatgtctc tctggattcc  10380
tcccaccagc ctctgcatgc accgaccaca gccctgtccg accagcctct gggtctttct  10440
cccctgccac ccagcccatg gccacagccg aggccgggcc tgctcactca tactctcact  10500
ggtggtgagt gtcctggtga ctgcctcact ggcttccctg cctcccttcc aggccatttc  10560
ccacacggcc atccgtagga ttcttcagag ccccactgct ctgtgctcac ccagaaccct  10620
tcacttttac cacacgcatc ttcatgaagt ccgggccttt gacattcagg acactttcca  10680
tatgcttttt ctttcttctg cacctatctg ttgctgtcgt tttaacctgg gggccccttc  10740
cttgtgtggt ctacccgggc cctgcccttc tttggcatta gccaaagtgc tgcttcctga  10800
cctgcctgca gccctgtcct ctccgagctc cacggagggg ctcggccatg gcgtgcgggg  10860
tgtctctctc cccgctagac cctctggacc acagcgtctc atagtctgcg tctttacgtg  10920
actcattttg cttcctgagg ccctagtgca gttcctggca ctgagaaggt ttagtgaatg  10980
agaaattgtt agaatttttt atatcaggac ctgtgatgtc ctgattccat tcaccaaagg  11040
caaatcatcc ttaagcgtga gtatggagaa aatgctgacc ttgttatctt cacttctgct  11100
gagctctagc aggtttgtga gcagcaaata tttgtgatgt ttctgtatag tcaaatatcg  11160
cttatgcttt ccaccctttg acatctcttg gtaccttgct tttgggttct gtgtttcctg  11220
ggactgagtc ttgctgagtg attccagtgt cacctgcagg gactctgctc tcaaggccaa  11280
ggcagatgtt cagtcatctg tgccacgtgg ctactccgag gcagaaccgg caagtctgga  11340
cacacctagc atcctagcct ggtgttctct gaagctcaga acgagcatct tgctccttgg  11400
tgggcagaag aacaagagga aaggaagcca gaaaaagagg accggggaag ccacagaaga  11460
gggagggagg gaaagtggga aggaggactg aggacaggag gcatgggtgt gtcctgcggc  11520
cttggtggag cctgtcctgt ggaaggttta ttttctgtaa agaagcagtc tggctcgtgc  11580
ctgtactcag cctctctgtc cccacacgtg actgtcctta gaatagcaac tgggtcctcg  11640
gattccagta ccccaccatg actgccgcca gccactccta tgtcagtctt ggctgtctgc  11700
caggcactgc tgatgattgc ccccagaacc gtactattaa tcccattaca cagatgagca  11760
aactgagacc cacagaggct gagtaacctg ctatagtagt aagggtcaga gcaaggcttt  11820
caacctgggc aacttgcatt ccaggccttc ctcatagaca gagtctgtgt ctattaggaa  11880
aggctacaag gagcaggtgg catgtgagcc gccacggagc ttggcttggg gctttctaag  11940
tggctagggc agaggggtgc agtccaggca gatggagggt tggggcagaa gggacctgtg  12000
aagaagtcct cctgtactat gggatcctcc cctccttatc agggctctgg cctggagctc  12060
agttcaaagg cttatctatg caggaatgaa ggcaacattc ttgatgtaga gtctaagagt  12120
ctgaaggtca gggaaccttt cttggatacc ctcctttctg cctaccagaa ccctgtgttt  12180
cctgcctgct gggaggcaag tggaacacag tagaaccaga tcccaagagg agagaagagg  12240
ctggaggggg acccacagtt gcatagaggg tagcatggcc tggttataag actgtttaca  12300
ctacttgatt cctctcagta taatacagaa aggatatgtg gatacagaat atttttgcaa  12360
tacagaaaag aacaagaaaa ccataaaaat cacccatagt cccaccaccc caaaataatc  12420
actgttgaca ctttgggcca tgactttttg ttttgtgatt ctgtgtctga gtgtgtgcgt  12480
gcacactcat atgcaggttg aatatcctgt atctgagatg cttgggaaaa gaaatgtttt  12540
ggagttccaa ttattttaga ttttgaaata tttgtgttat gttcacttgt tgagcatctc  12600
```

-continued

```
taacctgaaa atctgaaatt ggaaatgctt tgagtgtcct gttggatttt ggagtatttt  12660
agattttcag gttagggata ttcaacctgt gtaggtatgc atgcacacac acacagacac  12720
acagacacac acacacacgc acacacatat attcaccaat gtcttataca aataggattg  12780
tctacttttg caacttgtac ctcccacgtc aataagtctt ctatggcgta acttgtaatg  12840
gctgctcagt gtaccttggc gtagctggcc catcatttgt gtcattcttt cctgacgttt  12900
aggtcagtga gttctttatc actgcgtggg gaggtggata gtgctgcagc tgctgtggaa  12960
ggtcaggacc gtgcagggag gtggaagagg ctctgccact gcgctgcttc cccgccccac  13020
atgccctggg tccctggtta tggcgtctca tcccacctac ctgcatctcc cgtccggcat  13080
caccagcctt gcagagggtc cacacttggt aacatctgtt cagttcaact cattaggatt  13140
ttatcgagca tttttattta aaaaattata cattgcatat aaatttataa atttagagta  13200
ttatataaat gctcccccat tgtaaagaat tcacacagtg caggtgtaca aagcaaaatc  13260
caaaatctcc ttcctcccct catccgatcc ctgatttact ccttccctga gatgtcacca  13320
ctgttcacac attagtatat gtgtcctgtt tctgtgcctt aacagacaga tacgtgcgca  13380
tatacacaca aaaagaattt ttgttgtttt tttttttttt aatataaatg gaatcacact  13440
aaacatgttt tttttttgg acctacctag gttttcttca ctaacagtgg gacgtcttgg  13500
gaatcttccc atgctcgtac atagagacct acctcattct ttttaaatag ttttatggca  13560
ttttagagat gcaacatgtt ttgttatacc acacctgtga atgttccttt gatttgcctc  13620
cagttttttt ctgttataag cagtgttgca gtggttatcc ttattcatga ctctgcactt  13680
gtgagaattt ctgtaggatc cataagaaca aaacaaatac tagttataat aataaatggt  13740
gattgctggc ccttactgtg taccaagtaa cttttcatgt gctttccttg tattgactca  13800
tttaatctta gaaactctat ggggtaggtg ttattattac cctcatttta cagatgtgga  13860
aacaaaagca cagagaggtt aagtaacttt ttcccagtta cacaacttgt aggtgccaga  13920
gccaagattt gaacccgaat agtctgactc cagagagggg acctgctgag tcaatgtatg  13980
tgtgcaagtt acattgtgtt agatgttggc catggctctc ccaacagata gtgccagttg  14040
acactgcccc cagaagtgtg tgtgggcccc accgattttg tgtagtgatg accaattgtc  14100
atatttgcca gttcttatag gtgacaaatg agatctggtg gttgttttaa tatgcttctt  14160
ttccctcatt gttattcaag ttaaatgttg cttggccagc acagtggctc acacttgtag  14220
tcccagcact ttgggaggct gaggctggag gatcatttca gcccaggagt tcgagaccag  14280
cctgggcaag atggcaagtt cctgactcta caaaaaaaaa aaaaaaaaaa ttagccaagt  14340
gtggtggtgt acgcctgtgg tcccagctac tggggaggat gaggtgggag aattccttga  14400
gcccaggagg ttgaggagtc agtgagccaa gaccacatca ccgcactcca gcctggacga  14460
cagagcgaga ccctgtctca aaataaatga gtaaataaag ttaagtgtct ctttatttat  14520
taggcatttt aatccttctc tgaattgctt atttatattc tttgcccatt ttttcagtgg  14580
ggctgtttgt cttttaatga ttgctttctc tgtgttgtag atattcatcc cttgttttta  14640
agtacgttgc ttttcattga acactgttca gagtgtttgt tggctttgcc tgttgttgtt  14700
tgaagtaaaa tctgcagcac catttgtttg ccaggctttg ggctcgtcac tcagtgtaat  14760
tcagagatga gtaagacaaa gtccccacct aaaatagaca gcacgtaact cttgcgagag  14820
gagtagtgaa cggaatatag gggcggagtc caaatgtttt aggataagtg aggagaatgg  14880
ggcagcctct caactgggga ttcagggaag cctttgtgac cagtggcgct agggccagac  14940
```

-continued

```
ctggaggggt ccatagaatg ttcacagagg aatgggaagt gggggtgtgt ttgggcagat  15000
ggatcgtgag tgctttaatc tgcatcccat ccgaaaacaa ctcaccttca atgacccact  15060
ggaaaagagt ctcatgaaga ggctacttac agggtgtgca tggggacaag ggaaccaaca  15120
gagggtgttg aggtacccgg ggactgggta ggcagtggtg gggagctgct gcagggatgg  15180
aggcaaaaca gtgttagcag atcctgtggg agctggagct gagtagggtg cagcctcctt  15240
ctggtgcctc cattggcctg ggcagtattg cctggagggc ttagtcttct gcagcactga  15300
gcagggcaga gaatggtgga gagtgggtca gaggtgtcag gggaggtgga gggagaaaaa  15360
tcagctcagt aaggataaaa gcagagatag aagttccaga tgtgtgaagg cctcagcaat  15420
cctcgatgcc attagagggt aggggggttc atttgctgct ggttttactt agcaaacatt  15480
tattggatgc tggctcaaag cctggccccg gacgaggtgc taagttataa agatgggtca  15540
ggcaggctgc gcaccccagt gatcaccgcc gtggcgccag ttttagcttt ccacgtgtcc  15600
tctccgaggg tcacagcaga ggcctgtggt tttatgtctg ttagacccca tgtacctgga  15660
tctgtgcctc cttgtcccag ttggagttta tttaggtgtg tctgtctgag gacagatttt  15720
aacatggaaa aataagtcca tttttggccg ccattgaatt cagtctaaca tacatcttga  15780
tcttctgctg tttttttcca acttaaacaa acaaacagaa atcccaattt gtgttcctct  15840
tgataaagcc caatttctat agaaagaaaa gaaaccttat tgctgtccta tcaaagtaac  15900
catttatgac tgagctcatt aacagtctta tacacggttc tgtttctcat ttgcaggaat  15960
atgatgccgt tagccaagaa caagaagtta gatttgtttc agaggcttag acaactttat  16020
gtatcatgac tttgataatc taagaccctc acaaccattc attcattcat tcattcatta  16080
tttatttatt tatttactta tttatttgag acatgagtct cactctgtca ctcagggtgg  16140
agtgcaatgg tgcgatctca gcttaccgca acctctgcct cccaggttca aggaattctg  16200
cctcagcctc tctattagct aggattacag gcgcacgcca ccacctccag ctaattttta  16260
tatttttaat agagatgggg tttcaccatg ttggccaggc tggtcttgaa ctcctgacct  16320
caggtgatcc acccacctcg gcctacaacc attcatttta gcacaagatg caaaagcctg  16380
tctgtgggaa tagatgcttt ctcttcccca tggagttctg tgaactcatt agtactttct  16440
aggattttttg tttgcttgcc tgctttttca aggaatttgc tattctacct tgttctgata  16500
tttggtcaaa tcagaaaacg ttagaaaacc aaattgattc tttcttacac taaataatct  16560
taaaatccaa atgaaggcta ggcatggtgg cttatgcttg taatcccaac actttgggag  16620
gccgaggtgg gaggatcctc tgagcccaga agttcgaggc tgtagtgagc tatgatcatg  16680
ccactgtact ccagcctgga tgacagagtg agacactgtc tctacaaaaa ataaaaaaat  16740
tagccagtca tggtggcatg tgcctatagt cccagctact caggaggctg aggccagagg  16800
attgcttgag cctgggaggt cagggctatg cagtgagcta tgatcatgcc actgcactcc  16860
agcctgggtg acagagcgag actctgtctc tagaaaagaa aagaaaacaa aacaaaaacc  16920
aatccaaatg aaacctcaga ggtaggtatg gacacattag ctctgggaga ctgtcaatac  16980
aaggctcaca ttgagggacc agaactaaca gacccacact atcacaagcc aggtcttaac  17040
agccttcctt ttccaaccag ggaagggcag ctctcaaacc taaccagagg atctttccac  17100
tttctctttt gattgttact cataaagagc cctggatgta ttttctattt tcttctgtca  17160
aaagttcaat ggctacagag aactatagaa aatcctgtct taacccaatt tattttctta  17220
ttccaagttg gttctacttt ccagcaattg gttcctttcc tggaggtagt tgctttgtgc  17280
ttggtgtgtg ctgatggctg tgccagcctg ggcatctcat catgccaggg agctgctcag  17340
```

```
cctcctccct ggtctctcct gaaaactgac ctcctcagtg gagtctcagt gaccaggcgc  17400
caccattgag agatcctttt gtctctccaa ggttgaggga acctgtttgt gcacttgcca  17460
ctgtcattct ccccacagcg tcagttttgt ttgaatcgtg ctgtcaggtt gcatgaatta  17520
gattgcaagt ctcgagcttg ggccatgttt ctgcatgcac cgtgggtgtg aaactgatgc  17580
ctggcagatt gtcccatcgt tagaaacact ggacagagcc ggaagggagc agccatgctg  17640
cccaacccgt tttcaatgcc atgactttgt cctgaggcct cttcagggag ctgtgttaac  17700
gttgagccca gtttgatttc tgcgtcggcc ccttcatagc agaagacgac ctgctgactg  17760
ctgtggccag gccacctggc cgtggggctt tgaggagaga ctcaagccaa caagtgccgt  17820
cagtcagagc atgtctctgg tctgcctgtg tccccttgct gggttctcag caatctgggg  17880
cgatgcctcc gttcgatttt tttttcctca gaggattatg gagttttctg ggtcatttag  17940
cttttttttta tcacaatttc gtgtttctta ggtccatcca taggagaatg gaaaaacaaa  18000
tgtgatacat tcattcagtg agcactcttt tattcagcaa tagaaaggaa cagacaacca  18060
gcatgcataa caacgtgcat gtgtctcata gacaggccaa gtgaaagaaa ccttacatga  18120
gggtgcctga ctccattcag aggaggttct agaactggca aaaccaaatg tgggggcatg  18180
aaagctggag gttgaccggg aaggcacatg cgagactttc tggagtgatg gctgtcttct  18240
gaatctcagt aggggtttga gttatacaag tgtgtacatt tatccaaact caacaaatgt  18300
gtaatttact tttgcttgtt tcatcatatc taaattttat ctcaaaagaa ataaatctat  18360
aagcaaataa tgatgtgtat gttgaagtct ttagggagat gtatgttgtg tactgatact  18420
gcagtttact ttggaatgca ccaaaaataa gatgtgttga caaatggata gaaggatgga  18480
tggatggaga gaagtttgat caagtgattt tagtgaatat gttaatggta gaatcaaggt  18540
aatgggcata tggatgtctg ccatacaatt cattcaacat tggtgcatgt ttgaaaaatt  18600
tcatagcaag atgttgggag aaaggtattt ttgtggacgt gggagagacc ccatgttgtc  18660
tttgaagaca taatcataaa tttatgttta gagatgagga ttagaagcct ttctagggat  18720
ttagtagggc aaatgatgtc atcaaagaaa tctcctggaa tctgggttca ggggcatttg  18780
cttttgtaga ggatgttctg gggctacact ggcatctgaa aggattactg tggctctctg  18840
agccactaac ttgctaggct ttccccaggc agagtttcag ccccagggag aagcttccca  18900
gtaaatgtaa atgagcagag tccgtggttt aaggaccttc ctgcggagga gagagaagga  18960
ggagagataa gccgcagaca cccctggcac ggcaaggtag gctgggttgc ttgcctgcta  19020
attatcttct cggtcttgct ccgcagtgtt tctctagttt cagaatttga attgctgact  19080
ttgtgtagaa ttttcagcct ctcgagttgt tgaattgaag ggcagcacca cagccattcc  19140
ctacagagtc ctaacggaca ggcgtcctat gtcggaatcc tgatcctgtg taaccccggg  19200
gatgtaccag ggcaaatgca gcaaagacac agcggtcaga ctccttgtgg gagaaccccg  19260
gcctaggaga agctgctggt aaatttaggg cacgttggag aagtgggggt ggggagagaa  19320
gagaagaatg aaagcattat tctaaggagc tacttttatt tatagattct cctaattcta  19380
ttaaaatgaa tgccggaggg atgtaaaact tggaacacat aacacataat agaaatgaaa  19440
ggacattaaa ctaaaatagg gaaaaatggt aaaatgagaa gagaatctta gtaccaagag  19500
gaagatgtga catttttctg aaataaaata atcttacagc acagtgtatg gggaaagtga  19560
attaaataaa gtaaggactt ggttagcaga aaacttggaa ggaaacaaaa tatttcataa  19620
tgaaaaggag aaagtgttaa gctgactcaa ggggaaaaca catacagata ttacactaat  19680
```

-continued

```
tacattataa agacagataa ataagatgtc attgttgtaa aaggaaataa aactaattaa  19740
atgtttaatg tgctttaaga gacattggtg aaataaaata tattaactat ggtaaaatat  19800
gtgaacaggc ataattcgcc tgccttgttc tggcagccag cacagtacct cacctcctgt  19860
gtacaaaaca agggacgttt gatccctgag ttggaatggt tcagctcttt cttcaaaaaa  19920
aatggcagtt agaagcacct ccaacaactg aatgtttgca ataatgccag tcccgaagtg  19980
agcactcagc gcgtgttgtt gccagtcata ttgatatcat cacggcgatt atcattagca  20040
ctggatgaga gagaaacagc acgtccttcc agcgtcaggc cttggagtca gactaggaaa  20100
gcactatttt taaagtagga atttaaagct agtaaaaagt gtcacggaga agatttcaga  20160
tccactgttt cttttacctt ttgtgttggc cgatttgaaa agcttaggat ggaaaaggca  20220
gaagttaagc caaactagga gacaaactgc tgagccatga ttcagcagct gggacatttc  20280
cagcctgcac accgtcctca ccggctccca gcgaggcacc cggctctagc cgctccattc  20340
agcagcgtgt ggacacccct gctcagtcct tcgcctgcct ggcatgttct tcggggctcg  20400
tgcccaccac cactgacgca aaagaggacc ctcttgcctg aaattaatta actaaggatt  20460
ctctcttaaa gatgaaagaa aataaaactt ggggttaaga tgacagacgg agggtctctc  20520
ggcacttcac ccatgtcggc atcttggagc cagcgtagaa gcttatgaag gaatggtttc  20580
tcgcctgcac acagtcacgc agggcatgta gcagctctct acacacgtgc atttgcctgt  20640
aaactacaaa tgctcactgt cttcattccc aagagactga agtgcctgga gaggctggat  20700
tattatcctc tcccccagct tttcttgctc tgggcatcac ttgggatgga ttgtacagaa  20760
aactgaccat cttaattaaa tgagcaggag ttgtaaggct cttctagaat gggagggcaa  20820
aggtgggagt gttttttctc cctgtaatag tcaaatttcc ccagaatgcc taaaaaaaca  20880
cgtgtttctc atagcgctat tttgatctag tagttcttgc aaaaagagct agtgacaaaa  20940
tgagaacttt gagatcagaa gagctgggta cgaatcccag cactttcgac gacaccttga  21000
tcaacagctg gggacctctg acatccttga atgtcaaatc attcacctgt aaaatatgat  21060
tgcaacaatc attgccaaaa tagaattcta tatccagctg ttgtgaggat tgcagcataa  21120
acttaaacct ccgtgagacg agctgtcatc actagtgcag atgtgaggtc tgtctccttg  21180
cctgacgggc acactccatg ctgatcctag agagagctgt gccttcctgt gtggatacct  21240
aacagcagtc catactgtga ccactggccc agcatcaagg acgtggatgg ccactcccag  21300
ttattagtac caactgctgt ctccttcatg gacattttgc ctgggatggt tctttattgg  21360
attttggagg agccatacaa ttctgggtgt ttgtggagtc ctggagtcat ggcccacctt  21420
ctgacacgag agctgaaatt tggaagcatc agatttctgt gattttattt aaccagtaat  21480
ctaaaagctc ctgctggaaa tggagagttt gcatcctgct aaggaataat atgctggatg  21540
tcacccaatt ccagagcatc atcaaacagt agctaggaat gtattcagat gcaaaaagta  21600
gatgatagtg gcttaaacaa agtggggctc actgttttca cacagtgaat atgaagatgg  21660
accatccagg gctggtgctg tgacgatgat gatgatggtg acaatgacaa ggatgacaaa  21720
ctcttactgg gcaagaaact gctctgaggg cttgatctca tttactactt actgctaacc  21780
cacaaactag gtactttccc tgtctccaca tcacagatga ggaaactgag gcacagagca  21840
ttcagatgac ttaacccaat tagaaatggc agagccagag ctgacaccac actttttttct  21900
cctttgttat ttttgaaaca tgtttaacat ttaaaatcta ttatttgaca catataaaat  21960
atttcccaca atatatttgt tggttataca aagtataaca atagaacctg tgaagccacc  22020
acccgtccag tgactaggct attaccagta ttacctacgc gttccttgca ccctaccacc  22080
```

-continued

```
tgccagacac ctccggctcc cgcaggaagc cactgtccgc gtggcttgcg tatctccggc  22140
gtagatgtgc ttagacaacg tgttgcttag ctttggtttt gagcactgtg ggaatgatgt  22200
actgtgtggg gtattctgag acttgctttt ctccccccag tttaacatcg tgtttctaag  22260
gtttagccac agtgtggcta tggccccagc ttagctgtgg ttctcttact ttcactgctg  22320
tgaacactac cgtgtttttt ggccagcaca tctcaatgta tctgtccatt ctcctggcat  22380
gtttgtaatt ctttttaag aattgttgtt ggccagtcgt ggtggctcat gcctgtaatt  22440
ccagcacttt gggaggctga ggcaggtgga tcacctgagg tcaggagatc gagaccagcc  22500
tggccaacat ggtgaaaccc tgtctctact aaaaatacaa aaaattagct gggtgtggtg  22560
gtgggcactc gtagtcccag ctactcggga ggctgaggca ggagaattgc ttgaactggg  22620
aggcagaggt ggcagtgagc cgtgatcgtg ccattgcact ccagcctggg cgacagagcg  22680
agactctgtc ttgaaaaaaa aaaaaaaaga attgttgcta agaacagcct tatacaagac  22740
cgctagtaca caaatgccag agtttctttg gggtgtgtgc ctagaattgg gattactggg  22800
tgtacatata cggcatatga atcctttgtc agttaacagg agtgggaaac cgtgtttccc  22860
agtttatgaa tttttttac ctgtatgggg tgtcttctga ttaaactgga gagttaactt  22920
ttacataatt gtatataaaa atttattctc ttttaataac aattctgtta agttataatt  22980
cacataggat gcacctatct agagcatgca gctcagtggg ttttggtaca ttcagagagt  23040
tgtacaactg tccccgcacc ccatctgata acattttcat caccccagaa agaaatgcta  23100
tccccgtctt agcagtcagt ccccatctac cccactccct taaccctaag cagccactca  23160
tctactctcc gtctctctag atttgcctat tctggacatt tcatataatg gaatcataca  23220
gtaataatag ggtcttttg tatctggctt ctttgactta gcatgttttc aaggttcatc  23280
cattttataa catgtattaa tatgtcatga tttttatcac cagataacat tccactgtaa  23340
tgaattgccc acattgtgtt tgctcattta tcaaccgatg gacatttagg ttgttcccag  23400
gtttttgct gttgtgaata acgctgctgt ggatattcac gtgcaagttg tatgtggacg  23460
tatgttttta cctttctagg gagcttatct agctgtggag tggctgagtc atatggcagc  23520
tctatgttta catttctgag aaactgccag gctgtggacc cacccttcac ggtctcacca  23580
gccatgtctg agggttccag tgtcaccaca tcctcatcag cacttgtgat gatgcgtctt  23640
tttttctgca cccatctcat agatggagtg gtttgcattt cccttacggc taatgacgtt  23700
gaacgtatgt tcctgtgctt tttggtcatt tgtgtctctt ttttagagaa ccgtctgctc  23760
agatttttgt tcatgtttag tgggtttatg tggcttttat tgttgtatat tctagatacg  23820
agtcctttat cagacacgtg acttgcagtc attgtcatcc ttctctgggt tgtcttttca  23880
ctttcttgat ggtgtccttt ggagcacgga cattgttttt ttaatccact ctgacattct  23940
ctgtcttttg attggtgtgt tgagaccatt cacatttaaa gtccttgctg gcgttgttgg  24000
atcagtatct accgtgtttg taacttttct gtttgttaca tttgttctcc gcacccctgc  24060
ccctccccaa ccccactcct ttctgccttc tctggttttc attgagcctt ttagataatt  24120
ccattttgtc tccttgctta atgtgtcgat tatacttctc ttaaaatttt tttagtggtt  24180
tccttaaaga ttacaataca gttcatactt aactgattta agtccacctt gaagtaatac  24240
cgtgcggcat cacgtgtagt tcaggtgcct tagatcatta ccaatgtccc cctcacggcc  24300
ccatctctta ggacaccatt gtcttccttc agttagcgct tcctctgttc ttgtttaaga  24360
aatccttcct accccacagt cagaaagatc tcctctagtg ctagtcagtg tctcagaagg  24420
```

caacaggtgg cccctctgtc ctcttctaat agccctcatc ccgccagctc agagccagag 24480
tggagcctca gccgttcctg ggtgtgtccg cacactctgc tctggagctg gggaatgacc 24540
tcaggagggg ctgagctgca ctggacgtac catcagatgg tcctgtttcc atgagcagaa 24600
caagacgtgc tgtttccacc cagctcagga cctgtgcgtc tcagtagcac atcagggctg 24660
tagaatcagt gcgggtttag ggcctgtgtt tagtagccag tgggaggtca gcgtgtgtcc 24720
ctgtccccag cacacagccg cctggcaaca agtggccatg cgagtctggg gaacgtgtga 24780
ggacaggctg aggacaggct caccacacac gctgattgcc cctcgcaggg ccctttctta 24840
aagggtccca gcctccccgt cattggtctg gacactggat gatgttgcaa atccccacta 24900
tggttctgct cagcagaccc agtaggtccc agcttctgtg tgtcaagcgg catctgatca 24960
ggcttgccct ctttttcatc ttggagcctc tccccaggtc ctgcgagtca agtacactga 25020
gtagcctctg tccccttgct taggtgatca ctctggtatg cccgccgctg gcccctacta 25080
cccaggatcc cgcagttccc gtggagagtg ggaacctggt gctgtgggag catcccttgt 25140
caccggcggg atagagcgga cagcctccat ggacttcttt aggaggacgc tgaccctccc 25200
ccaggcattt tcctaacccc ttggtgagga gaccagctcc aggcctcccc agggagtata 25260
ggccaggtgg cttaacaggg tgtcacgcag tagatccctc cagcctccca tttccctgca 25320
ttcccagcag accagcagca gctacatttg ggaccttgtt agaaatgaaa atccttggac 25380
cccaccacag cctgctcgat cacagactcc gggagagggc ccaacaatct ggctttaata 25440
aaccgtctgg ggctggagaa ccacagctct gcaggatgtc ccggaggtcc agcatactga 25500
cctcatcagc gattggtttt tattaattct agacttggat tagccaatct tgtagactat 25560
acacacccct cgatgttcaa ggttcacatt aaatgaccaa attgtgaggg aaccaccttg 25620
tccacacgtg tgggtacata tgacctactt gcatttcgtc ccgcttggag cccacctccc 25680
aggctcctgc ccccacacag tggacatctc cttctgacgc agttcctgtg ccttggggtc 25740
tgccttgttt tatgggccca ggtggcgcag gatgtgggtg agtctgtgga gaaagggcac 25800
cagcttgcaa ggcagcagcc ccaggagcag cctgggaagg ctttgtgcag aggaggcctg 25860
tttcctccta cgtgttggga gagttgtctc tgcagatggt gggtgagagt tcgctgccaa 25920
aaccactgtc ttccctgccc tgcggacact tcttcctcac cttcctaaaa ctgtaagaga 25980
cctggagccg ttgagcatca atgactcttt gactcaggaa tcttaaaaaa tcacaccctg 26040
gggctaccat gggggccttc tggttctcct tgtgtattac tagttgaatg tttatagctt 26100
tcaatttctt tttccccttc tatatgctct ctaaggacat aggaagaatc tacctgacct 26160
cacagctttg gtaggcactg ttattgccac accctcttct cccagtgggc accccacacc 26220
ccaactcccc ggcacgttgt tcagtgggac tgccagtatc atgtataatc atgaatgctg 26280
tggattatcc ttattcacac acacagactc acaccctcac acccagaaag gcaactatcc 26340
cagtgctccc agaatagatg aacaaccgaa tcccagattc ccttcgtgag gatttatttg 26400
aagaccactt tcagtaacaa ttactttatc agtggaggtc tcagcaggaa agatacggca 26460
catagtagag cactttgagg aaggtcacta gaccggttcc caaggcatgg gcggagttca 26520
gagaaaccac caggaactgg tagcagcaga attgttgcaa cgcttggccc caaaggaaga 26580
ggggagggaa tgttgatggc acctggaagg agaggttgta ttgacaagtc tccttggtag 26640
agcagtgata ttcggggaga aacacggcca gccagaagtt accctgtaga agggggcaga 26700
ggagaaaaca agccaattcg accctcctcc caacctgcct ctctcgtctc tcccattttc 26760
tgtttccaaa accgacccac agtcagaggg caaaggagcc aaccagaagg cccctgtgtg 26820

-continued

```
tgatttttaa gattcctgag tcaaagagtc attgatgctc aacggctcca ggtctcttac  26880
agttttagga aggtgaggaa gaagtgtccg cagggcaggg aagacagtgg ttttggcagc  26940
gaactctcac ccaccatctg cagagacaac tctcccaaca cggaggagga aacggccctc  27000
ctctgcacaa agccttccca ggctgctcct ggggctgctg ccttgcaagc tggtgacctt  27060
tctccacaga cttgggcccc catagccatg tgcctggggc tgaaagcacg gtagaggaaa  27120
ccggaaagtg gatttagagg gacaaacaga agatatccaa cccactctca gacgtcctcc  27180
tacaagtttt agttttactt ctcacactta agtatttaat ctagctcaaa ttggttttgt  27240
gtttgatgtg aagtagggat tttattttat ttttttctca tatgaataac cacctttttcc  27300
cagcatcatc agtggattag ttcctccttt caacactgat attctatcag taaatcaagt  27360
tctgtatttg catacagatt gtctcccttt tctgttccac gagttaaact tgtctgtctc  27420
tgacccagtg cctcacagac ttcagtactg tatcttcata ataaggcttg atatgtggtg  27480
gggcaagtct tattcttttt caggagtttt aggctattct tggccctttg ttgtttcata  27540
ttaactttga atcaacttga caagttccac aaaacaaaag ctgttgggat tttgactgaa  27600
attttattta atatatacat ctatctatct aatgtatctt tatgatatgg gaccttccta  27660
tccatgagca tggtatctct ttatttaggt ctcctttaag tattagtaaa gtttgtaaat  27720
tcttatatac acaacttaca catctctgat aaaggcatag gtaccttaag tgtctaacag  27780
ttgttgctag tatatagacg tgcagttgat tttttagatt ggtctcacat ctagccacct  27840
ttcaataaag tcccttattt cttccaataa tttgtctatt ttttatgtaa accataggaa  27900
accatagatt tgatatggtt atctatgtag atagtcatat catctgtgaa taattgtagt  27960
tttgtctctc cctaatcaat ctttaagcta attatttatt tatcatggct gttgttgact  28020
agaactttca gtataatgat gaataaaagc attgattttg ggcagtctta tcttgttctt  28080
gattttaaag ggagtgcttt cagggtttcc acattaagat tgatatttgc tgtttgtttt  28140
ttgtaaatgc ctttttaaca ggttaagaaa gcttccttct tgttttaatt tgctaagagt  28200
ttttaatcat atgggttttg aattttatct aatgcttttc ctgtatcttc tttattctgc  28260
tactgtaaaa attacagtta ttgactttct aatgctaaaa tacccttgca tttttggaat  28320
aaactcacca tggtcatggc agactatctt tcttcctcgt tgctgaattt ggctttctaa  28380
tattttagtt aggagttttg cttctatatt ctgggtaaag tggacctaga gtttcccttt  28440
cttatactgt tcttgtctgt ttttaggatt aaagtattct ggcctgataa atttttactt  28500
tttctgttct ctggaagagc ttgtttaaga ctgggatgat ctataccttg aaattttggt  28560
acagcttacc tgtgaaactg tctaggcctg ttctgtgtga gagagatggg tgtttaagca  28620
ctgtttcagt ttctttagtg gaaagtttga caagtcctgt atttgttttt tagttagtgg  28680
tttcataaat tacaattttc taggaatttt ttaatgtggt ctgtgttttc agaattatga  28740
gtgtaacggc attggtagtg tttccttatt gtttttaaac ctctgcttga tctgcggtta  28800
catccttttt ccacttatca tgttatttat tcgtttgcgc cttaattttt ttctttatca  28860
gtggtgccat gggtttggct atattgccag atttttaaag aactgcattt ggccttttaa  28920
attctattgt aaatttgttt tctactttta cagagttctg gtcctaattg tattaccttc  28980
ttctcatttt tttttctttt aactttttag tttgatgctt aatcccatga attttcagca  29040
tttctcttac cacgaacacc tcaggttaca cacatctttc ccggggtcat gtccacagtt  29100
cccatgagtt gtcctaaata gtattttcat tatcattcca ttctaagtat tttttttatcc  29160
```

-continued

```
caattatgat gttttctttt accatgagtt atataaacat gtgtttgtga atttccaaat  29220
gtgtgacatg tttagtcttt ctttgccctg ttgacctcca gcttaattgc attacagcca  29280
aagactatgc tttcttggaa atcagttctt agacatttgg ggggtgtgct tgaagtcctg  29340
gtactgggct cagtctttga aaacgttgtg tgtctctaga gagaaatgtt attctctgtt  29400
gttgggcgtg gagttctaag tctgctggat tacacctctt gacagagtgg ctcagaccct  29460
ttccactgcc attggctttt tgtctaggtg accctctgct acccctgtcc cttatggccc  29520
ctggaatcag ggagcttatg taggaggagc aggtgtttgg gctggccctg gagggtgagg  29580
aagatttggc ttgatggagg taggcagggg gcctgggtag aggggacagc ataatactgg  29640
tgaaggaagg ccagggaatg gtgtggcatc tcgaaagagg gccagagggc aggaaaaggc  29700
tggggcaggg accagaggcc ctgggaaaga cccctcttta gaagaggggc aggagagagt  29760
cttctgaggg gagatgagag agagcccaca gagaggagga cacggagggg tggggttggg  29820
taggcccagg ccatcgtggg gggtcttcct gggcaggaga gggacctgtg tgacggttca  29880
taggggcata gtggtggcca tgtggctgtg tggggaggag gccctcagtt cagtgtgggg  29940
cctgggatag tgggtggcaa acatcagatg gaatttcaca gaacctaacg cacatctctc  30000
tccctcgagg tgaatttttc tttacagacc tgtgaatcta agagatgatg taacgcctga  30060
actcatttta taacatcaga agtttgcgac ttaaaaatgt ttcagaaggt gggggcgtgg  30120
gctgtctagg gttctaagga gaacgtggtt gaaacagctg cctaaaggga ctgagggtgt  30180
tggaggaccc ggtggcaggc gcatggatgg aggaccagga accaccaagg tcaccatggg  30240
tgggaggcat cagggtgagg gaggggtgtt ggtgaggggc ccagctggag ctgtgttcat  30300
agttgctggg atggagggga cagggcagga ttcagggtgt cagcagagtc agttacctgg  30360
gaggcgtggc acaatggtga tggaggaggg ggagcccaat gatagtgcag tgaggaatgg  30420
tgggggggac gggaatggtg gcagctggtg gtgtggactt agggtggggg gacgggaacg  30480
gtggcagcgg gtggtgtgga cttagggtgg ggggacggga atggtggcag caggtgatgt  30540
ggacttaggg agaggagacg cggagcaagc cgggagaact gggtgggcct ggatttgtcc  30600
tttcctggta ggattactgt ggccacagaa tttattgtgc aaccaggatg tttctaggaa  30660
gtaaaaggga gagcctggac acttacagct gggcaacagg atggaggaag ccagcacaca  30720
catgattccc tgtgcaggca cgtaggggct ttcagctaag ccaagggtgt gtgaggaagc  30780
accaaaggtg cagaggagtt tctcccttgt tttggcttca aaatagatgt ttgtatataa  30840
tagggattcc caagggctca gtgggcggag ctagcagtga ggctgggaga ggagaggtgg  30900
cctggagagg gtttctcttc tgtccggaag cctttctccc ttggctgaga gaagctacac  30960
acacgccact tctctctgaa cacgtggctc gtgaaccaca gtcctacagc tgtcagtagt  31020
aaaatccagg cccatccagc atgcttgcgg gatgtcgggg tggttaaatg aaatggaagg  31080
cagtttgttt tttccaagtg agatggatgt gaaggaatta ggtagaagct gacagaggta  31140
tacccaaaac tgctaaattt agcctggatt caagaaagag gttagagagg tggcattgtg  31200
agtaattaga cgcgtcgcag agagcgtgaa tgattgacag agtttgtgtc tgtggttgcc  31260
gctggggaga aacagagcag agtgggagtc ttcggaagga gcgaggagcc aatctgctgg  31320
gtatgtggag cctttgggac cgtcagtcgc gcttcgggtg ctggggtctg tttgcgctgg  31380
agaagataca catggtgaaa gggagagtga ggcacagtcc ctggagacag acgatggtct  31440
gtaaatggtg agcaaacaac agtcaggagc cttgctggag tctgtaccaa gggccctcct  31500
aagaagccgg gtcctgtggg ggtccagtga ctgtgtacag cccgggggtc cagtgactgt  31560
```

-continued

```
gtatagcccg ggccacattg cccagctcgg gtctctacgg catttgggtt tatgcctcag  31620
ctcaaagcct tgcggaaacc cctttcaaca tgtgcgctgt ctgctgcaga gactcaaacc  31680
cactggggca aagcgaacac acagcactgg agttgggttt cacgtcccta tcaccacgac  31740
ctgtgcccac caacctagaa atagttgggt gaacttgctg gttgtttgct gagatagtgc  31800
acatggcagt cacataggtc tttactgtgt cttgcctgat agcccagcat gagtagaaca  31860
gccatggaga cctctgagag agcaggacga atgtgtctga ccatgttgtt gcaagccacc  31920
taaaacgtgg ctggacccag ctccacctct ggagggacgt accacgggca accatctgtg  31980
agggtattgc agacaccaga tgtcagcgct ggtagggggt aagcaaacat cagatggaat  32040
gtgagcataa gagatgacat aaggccagaa tgtgttttac aaaatcagaa gttttggact  32100
taaaaaatgt ttcagtctgg aattggacag atagcgcagg ctcattttat ggataagaaa  32160
taagttagtt tcaagaaaat ggattgccag acacgaatgg tattgcacac ccagaggggt  32220
ggccagggct gcctgtgtgt gggctgtccc cggcacagct cctcggctcc cctctgccct  32280
gcaccctgta ctgttcacct tggccctgta tggctccgtc taggtgggat tatcttcccc  32340
acaggggcca ctgataaaga agcactctat atatttttaa gaattgaaat caaagggcaa  32400
atgggatttc tctaactttg caactagctt tattgcaatg cacttccccc cacaaaggga  32460
gctgcatcct tgttcttttc tttaagaaat actatgaaaa aacccagctg accagcctgc  32520
gccctgggag gctggggctg ctctctgtgt gccaggccgt gagccgagca ttccatatgc  32580
atcacgcctc atttatcccc ctagaaacct tgggcaagga aatgctgcta atcccaatgc  32640
atggaaaggg aagctgaaga gaaatttagg aacttgctca gagatccttt tcacttaaac  32700
agaggagttg ggattcagat ctgggtagtc cttggctcca aggcccaaga cctcaactgc  32760
tgagttgaga tttttattta tttatttatt tttatttatt tatttatttt tgagatggaa  32820
tctcactctg ttgctcaggc tggagtgcgg tggcacgatc ttggctcact gcaacctccg  32880
cctcctggtt caagtgattc tcctgcctca gcctcccaag tagctgggat tacaggtgtg  32940
caccaccaca cccagctaat tttttatatt tttggtagag acggggtttc accatgttgg  33000
ccaggctagt ctcgaaatcc cgaccccagg tgatctgctt ggcctcccaa agtgctggga  33060
ttacaggcat gagccactgt gcccagccca agctgagatc ttgatactcc ctctggagtg  33120
tccttggtca tgcaaggcaa ggcctggggt cccttcattg ctacctcctt gcctcccttt  33180
gaccctcacc ttgtgtattc cccctttctc tccccggctc catcttgcct cgaaagacga  33240
gtagagaaga tgttccctcc actgctagga ctccagcttc taagaatgtg ggtccctgtt  33300
tttatccagg ggtgcatctg gcagattgcc gttccttgtt atgccctctg agagcccggt  33360
aggcaaagcg gtttcctatg tgcctccttc atcttgctgt gtcatgctcg ctcctgtcag  33420
cctctcccct ggatccaggc cctgggccca tgtgggccct tctgggtccc tcatgtctaa  33480
aatacctggc tcgagcagct gcccagatat ttgttgaggg aaggaatgag ggaatggaca  33540
gacgcctctg gagacctgca gtggcttgag aaaacaagga caagggttcc agacagaaga  33600
ggaaggaacg gttggagcag cccaggagtc agggtgggcg tcactattga taaacgcaca  33660
gacggtgact gcacagagtc tcgtcactgt gggtgggtct tcaccaagtc cctgttgata  33720
agctgctgtt acgtgaatca gcacgtggag gggaccatcc gtccttccat ccctggagta  33780
ggatgatctg tcttctctta ccctccttcc aagcaattac ttctcatctg taaattagtg  33840
ctgctgaagt tttactttga gtatgcaagt tctgttgaaa tcatttattg gcaaatattc  33900
```

```
cataagccac agatgttagt gcaaatggga tggagagaaa aggcaatgta gtgcctcccc  33960
gatagagtag aaactgtggc cagcaagggt gcagagatgg gctgggacct ggtcccctga  34020
cttcttagca tacagcttgc cggagaaatc ccaaatgcca tttttaaaga gccatatgaa  34080
aattgcacaa agtctatttt tagtttacaa gccaagatat gctttgcaac cgggaaagga  34140
tgtccctcag ttgtattttg gtgaagtcat gacagctgcc tcatcagtag cttcttcatt  34200
tttaattacc agcgtggggt tgagtcacag aagcagaatg acagtgcatg tttctctgtg  34260
cctggtttta attggtgtga ttgagttggg gcattgatgc agctggatga aagctttctg  34320
tatcttcatg cactgggagc tgccgacctc agcagggcaa gctgtcacaa ggccagcagc  34380
ataggagctt ggtcactgtg ccacctggtc agcaggcctt tgaagccatc atttgggata  34440
ggctccagga taaaaggaag ctgagcttgc atggtgtttg gctgacactc tcaccaccca  34500
tgactgtcag tcccggtcag gtgactctgg ccgtccctga gatgattgcc acctccttcc  34560
tgtgtccttg ttccctttaa gggaaaccac acaatagaga ggggccaagg atgggaagcg  34620
ctttccggag ctaagagctg ttaataataa cagctgggca gcactgccgt gcttggctgt  34680
gccttggggt cggctatgcc ttctccctct caggcctcca gatgctgctg gtacactgga  34740
gccatagtcc cagcatcctg agtgacacaa gagaggtggg aaaggtgggg acagaatgca  34800
gaggagagtt ttttgtttgt ttgtttgttt gctgtggtca aatacacata atagaaaata  34860
tatcatctta cctgtttgta agtgtatagt ttggggcatt tagtattttc acgttgttat  34920
gcaaccatca ccactgtcca tctccagaac ttttttattt tctcagactg aaactctgta  34980
cccttttatt tatttattta ttcattcatt cattcattca ttcattcatt catttttga   35040
gatggagtct cactctgttg cccaggctgg actgcagtgg tgtgatcttg gctcactgca  35100
acctccgcct cctgggttca agcgattctc ctgcctcagc ctcccaaata gctgggatta  35160
caggtgcacg ccaccatacc cggctaattt ttgtattttt ggtagaggcg gggtttcacg  35220
ctgttggcca ggctggtctc taactcctga cctcatgtga tctgtccacc tgcctcggcc  35280
tcccaaagtg ctggaattac aggcagaagc cactgtgcct ggcctgaaac tctgtaccct  35340
ttacacacca actccccact cctccctccc ccacagcccc tggcaaccac attctgtctc  35400
tatgaatttg gccattccag gtaccgcata cagggagaat cgttcagtat tcgtccttag  35460
tgcctggctc atttcactga gcacagcgtc ctccaggctc atctgtgttg tagcatgcat  35520
cagagtttcc tccctttttc aggctgagcc atattccatc gtgtgtccct gccaggtttt  35580
gtcgatccac tcaaccagcc acagacacct gggttgctcc cacccccttgg cttttgtgga  35640
aaatgctgct gtgaacacgg gtatgcagat atttgttcag aaccccgttt tcacatcttc  35700
gggtacagga ggtatatatt tttaagtgaa aatttgaaga ttaatttttc tagaattcct  35760
tttgatttcc cttgggataa cttgctctca agtgatggtg ttttaggtat taaaatgtga  35820
atttccaaca tgtctttcat aaagacaaaa tcttattttt aaaaaccttg tagcctcctc  35880
caacatgacc tcccttggcc aagtagccat gagctgcagc ccagcactga cccttctttc  35940
tggggagtcc aggagggggc ctggcaggag ccagacgggc tccccctgac tgccttgggt  36000
gctcagtgta gtttgttctc tgatccatga tgtaagcagc gtgcccaggt gtgctgtgca  36060
cagcctttgg tgctcaaggt cacagacaca gtccactctt cacgagcaga gctgccctat  36120
gctgagagta gacctggact cgtaccggag cctctctccc ctggcaaatt ctctagatga  36180
gactttcttg aggataaggc accccctact tctcgcatac tcagaaagaa aaaagtaaac  36240
agtgggcctc ctcaagttgg gaaagtctca accaaatgtc tcgatcccca ctttccaggc  36300
```

-continued

```
gacaggctgc ctgtagcctg caggcatgtg ttaggcaggc tacacagtgg tggtaacatg  36360
tacaatgagt tgccattatt aaaaactcgg gagagcgcat gtcggatcca aatgctggct  36420
tctctggaag agttcaggag atctcgcagt tctgggttcc tggagcctcc gcaggctcac  36480
ctcctccctg acatggggtc ccaggctggg ccctgtgggc atcgggggta cctcacccaa  36540
ctagagaggc caaacatggc acagggaagt tagcgagcag cagggagatg tggctcaaat  36600
ccattcccac taacacatca gctgcacagg ggcagcctgc ggggagcagg ggcgtgtgct  36660
ctgcctgggg gtgaggtatg ggccctgggc acatggggca gggccaggcc tcaagcagcc  36720
tccctacccc agaggtcacc tgcccttgaa atacacctca ttttctgtct cttttacaaa  36780
ataattcctg gatcccacgg gccctccttt gatgggagga aggaatgggg cagctctgag  36840
aagcagtctg tcgccgcttc tcagcatggg gttagagaaa gagttttgtc ttcagtttag  36900
accatacatt ctttaagctt tatttgggaa aggggctaaa aggtctggtt accttgtttt  36960
attacaatta aaaatttctt ttacaatttt ttgaaacaat cacaaactta cagaaaaatt  37020
gaatgcacag ggcaaagctc aactgaccca gcgcagagaa cctggtgacc ccggccccgc  37080
cagccccagt gctccagtgt gtcctttgca taaacaagga ctgtgtctgc agagccgtgc  37140
agcacagcca tggacaccgg ggaattccac cggtctttat cagttgtaag ggcccctaat  37200
gtagtaacat gttccatctg tgctctgtgg gtaaccaatc tgccatgtcc tgtgtcttca  37260
ctttccctga gtgggcagcc tggttatctg cctggactga catctggagt agcctgttcc  37320
cacccgtagc cccacgggct cgattccacg ttcccccatg tgagcgccct cctcaccttc  37380
tgagttgcag cagtgccttg ttctgggcca ccccggatct tcccacccca cacacaccat  37440
gttcttcccc atatgatgac tttagactgg aatttttcag gaaaaagaag agttttacag  37500
cttatcttaa aattaaaaca aaacaaaaca aaaatgaata ctcaagaggc attggattta  37560
ggaatccggt aaaacaacta attccagaca gccgtaaaga aacctgcaac caggaaatga  37620
tttaaaatgg agatcttcaa agtcaggatt gtagtttttt caggtagctt tttgtagacc  37680
ttgaaaatat aggccgagac cacatgtaga aattaaacgt tctcatccga agccggacca  37740
tttggtttgg cgacttaagg gaagagaaaa atgaagtttg ctaagtaaga attaatgatt  37800
tctcaggaat ttttaggatg ttgaacagct taattgcata gtttgggtgg atatgtgttg  37860
aagaaagtaa ttttaggaga ctgggaaatt gtgcaatcat cttaacttgg gtcaggattg  37920
taattattgc aataacagaa tgttgctatg tgtatatgtg actgaaatgg gaagcagttt  37980
ttaaaaaatg ctttaagaaa taacaacaaa atgtccattc tctctctctc tttctggact  38040
tccttaatta taaataccag gtaatccagt gctggctaaa tataggtcca gtggtcatct  38100
atatttataa cgtttttttc aggcggaagt cactagagca atacagaatt aatttggtgt  38160
gtaggttttt atagagtcta attagttgtg tttttcttaa gcaaaccaac cgggatcaat  38220
aacattatat aactgaactc ggacgaccat gacttttaga catagactct tcccagaaag  38280
ccaaggccct cggcagatgc cggccctgaa gacagacaag cggctccgga agcaggcacg  38340
ctgcagctgc ggagcggacg gggtttggaa catctgtttc cagccaaggg caggctttgg  38400
gagtgataaa gtacagtttt tttttgcaaa gtcagaagcc tcatctgcag tccattcatc  38460
actgaggcct tgaattgaga cattctgtgg ctgcttatca gctgttcccg tgtggaaggg  38520
tttggctggg ctggcctggg gaggtggggt ggggattttg cagacttacc aaagtatgcg  38580
cttagccgac ccaccccccac caacaacgca gcctgctcga gggctacgaa ctgcacctgt  38640
```

```
gtctgcagtc acgtccattg gagagctgag tgggcgggtg gacctttgga actatttgat  38700
gtcatttggg gtagattcgg cgtgcttctc ggtgactttg ctgcaaatta aacatgtaaa  38760
gtagattggg ctttcctcct ccattcctca ggatcttcaa aaaacattta gtcttttctg  38820
gcagagtgaa cccgagctgg cagcgcccac tgagattttg tttgaagcca gctacattca  38880
catttaaaga aacgacatga tgggggaggc cctttctgta aaccccaagc caggcctttc  38940
ccctcgtgag ggttcctacc cctcccttgt gtggccctgc aagccgcttc tgcttgtcca  39000
cacctgcgcc cgagagttct tctcatggct ggtgcgtgcc atgaatgaag ggcactggcc  39060
agtggaaggg agtgcccggc caggccttgc ctgcctcaag tcctcagacc agagaggcca  39120
gtgggggtct tgcccagacc atacagccgg gaggtggtct gcctggctcc atagcctcct  39180
cccgacctca cagctgtcct gggacgggga ctgagagaga gctcaaagac aggacagcag  39240
agcccgggcc agaaggcact gggggcatgc tcaccccacc tctggatgcg gggcctcact  39300
ggacagctgg acacagatgg gatgggggga gacctgtgta tcctcccaat gtcatttgga  39360
gacagaagtc tgttcatttc atcaggcaga tttcaagctc ctctgtgttc cagacacagc  39420
caggccctga gaattgacag acaacatagc tcctgccctt gaaggcttat ggtggaggga  39480
gggaggacaa agggtgtcat agccatgtct gggcatacag ggcctgggag gcctgagagg  39540
gcttcctgga gtcagtgaca gccgaggga tggttaaaag cagagtagga gttgagggga  39600
cttgagcgag cacaggggtg tgaaacggtg tgtgagggca gggcccctta cactggatga  39660
cagagggcag tgtgggcagg gccaggcctg tggctggaga ggggtcctgg ctggtcgtgt  39720
attctccgag acaaggagga gtcagggtgg gagtgtcagt gcggtggtac gggagagact  39780
aagaggccag cgagggtcca agcagagggg tggggctgcc tgcactaggg ctggtgcgat  39840
gaggggagcg ggtttgggag ccattaagag ccccctttgg gaaggtttgg tggtggcttt  39900
taccaagaca aggaacgcct caggaggaga ggtttggggt gcaggatggc gagggtgcag  39960
tgttgttgat gctgctctgg cgtggtggaa gttatgtgct gacctagggg tcctgccagg  40020
agccagtgga taaagatggt gcagatccgg cccagcccct ggaggactca gccattatgg  40080
ggccacgtgc ttgggacccc cttaggcggg agaggctccc cagaggagat gatgctgagc  40140
tgagcctgga aggacccagg attggttggc aggaaatgaa gaaacagcct tctgggcctg  40200
tcttctcggt atctcatgca gttcctggat acagctcagc ttctcccgca gaggatttca  40260
gaacccacct ccccagtggc tgttcagacc tctggaacca gaacgtccat ctggggccaa  40320
gcccccaccc acatggggtt gctcaagcta ctcaggtgaa gctgacatgt acgaaggtgg  40380
cgagccatag atctggagtt ctgagttagg gcaacccagc agtggcccca ggaggctcac  40440
tcggatgtga gaactgtggg aaaaccaagg acctacctgg tatgtttcag agtcatttgt  40500
ttatgaacct tacataaaca cacacacctg gatatgtata tacacgtgta tatgcacaga  40560
tacacacaca cgcctgaata catatgcagt tggctgtctt tatccacggg ttccacatct  40620
acacattcaa ccaacctcag gtcaaaaaca tgaaaaaaaa atgtatggtg gatgtagaaa  40680
ctattttctt gtcatttttc cttaaacaat atggtataac aactatttcc acagcattta  40740
cattgtatta ggtattataa gtagtctaaa gatgatttaa agtattggag gatgtgtgta  40800
ggttgtatgc aaatatgatg ccattttata tcaggacttt gagcatctgt ggattttggc  40860
atctgcaggg tggcctggaa ccagcccccc acggatgcca aggcatgact gtatacatat  40920
atatacatct gtatacaaac acttgcacat ccatatacat atgcacacac acacaccggc  40980
atacgtatat acacgtgtat acaacactca cacattctat acatccacac atatgcacac  41040
```

acactcgtat acagacataa tggaataata tgtacctgaa acataatata ggcctcccat 41100
gatttcctta ttgaaatgaa ggaaagtgca cacatgctga gggtactggt tctctgggaa 41160
agaacctgcc gcaaaggaca aggaccaagg tgcctgaaat tccccatggt aactaacaat 41220
cttaaccatg ccgagaggca gaaggttcaa cggtgaagaa tcctgactgt tcattgacta 41280
aatgaatctt gaacagtttc actgctctgt gcctcagttt ccccatcagt cagatgagga 41340
tggtcataac atctactccc tacagttgtt atgaaaatga agcttattaa ttcatctgaa 41400
ctccaagctt gctgcctgga atggggcatg tgcccagcaa gcgtcagctg ttgtaatgag 41460
ccaggggcac tcggtaatag tgaggatccc tggctggggg acaggtgaag gagggggaat 41520
tgctgttccc cactaactct gtaccctttt gtaccttcca tgttttgtat catgtgcaca 41580
tattacctat attttttaa atgtcagagc atcttgttaa agaggattac actacattaa 41640
actctcttca ctgtgagttc tttgatctca ttccttccag tgttctggtc aagaacattt 41700
agcaaggttt gtaatgatgt tctaatgatg ttatcagttt gatcaagtaa tgcatataat 41760
cgcctatcaa cgttgagtaa agaaacatga gcaccctgta ttcagcaaat tgtttatttt 41820
cttgaatggt gcatgagacg ggctctaatt aattcattgt gaagatacca cgggcaccaa 41880
agagaacaag aacgtattta aatttcatgt tatgacatta caaagacaat gccttgtgga 41940
ctagcagtca gattcattga tgaagagcag atggaggtca ggggaggaca cggggctgag 42000
caggactggg acgcagcctg ggatggtgga ggcagcgcct cccttctata atcgagggaa 42060
ggaggaggag gctgccaggg ccctccgata gcggcagtcc gtggaagcca ccgctcctga 42120
ttctaaaggc gggctgctca ggcaccggct ggagaagcgg tgcgtagtcg atgagctgtg 42180
agcacgggag cagagccagc gcctggtgtg gacaccgtcc gaggccacag ccaagcagca 42240
gccacccagg acgtccaggc tgctgagcag ggaggaacac ctgccatcag ggcaaatgcc 42300
acataaaaaa agaacctcac tttacctgga agattatttg gaattttgtc tttaggccgc 42360
ccccttcctg agtccaccgc tgtccatttg accctgaaga ggtcctaaaa gtgtggcagt 42420
catcttaaac cctactcgtg tatctgtatg tcatttagta tcaaattttg tcacctgctt 42480
gtctgtgagc agaatgggga ggctgctggt ttaggaactg ggagccccac agtgtgacat 42540
agtcttaacc tccctgggcc tcagtatact catctgtgaa atggggacat ctctgtgggt 42600
ccttgtcaca ccctaatctg tgagtcaggg ccagagggca gccaggtgtc cttcatgttc 42660
aaccaggcca gtggccacat ccccacaggt gaccctgcgt gagcctgggg gcctcacagc 42720
ctggcatcct gtccccctc cccatgaagg cacccagaga tgtgaaggaa cagcctccct 42780
cactggggag gggcagaacc tcctcgtacc tggggtggac cctgctgtgg taggtcagat 42840
gagaagccta gaagggctta ggtgggtggg gaggacgaga gacagcaatg gctgtatcat 42900
aaacgcagca tcatccgggc cgacgagact ttcaatgggc ctgtgttcct gggcagctgc 42960
tcctgcctcc tgctgtgtca cctttgattc tctcactggt tttgcccgtg atgaaaacct 43020
cacactcctg acctggtgcc tgatgttgca aagggagggc agagggcagg accacatgag 43080
tcagacagaa ggacggggcc tcttggagca tctgacaagg tttatggaaa aagcacgtct 43140
cagagactca atgagatgct gaaggtctag gcttgcagcc gcacctgtgt ttgagtcact 43200
ccgtgtatgg accgccactt cccagcccta gagaaccctt gcttgacatc agagactttg 43260
gtgaactccc ctgatactct cagcagcaaa tgctgtacat cacaggctgg cagccttttc 43320
tgtttcagag ttcacatatg aactctttga tcctcgtggg ctctagggtc tctgttgcaa 43380

-continued

```
ccactcagct ctgctattgt agtaggaagg cagccatgaa cagtagggaa agggtgggtg  43440
tggctatgtt ccaagaaaat ttatcaaaaa acggtaggtg gatatatacc caaaagaatt  43500
gaaagcaggg acacgagcag atatttgtac acagcagcat tattcccagc agccaagcag  43560
tgggagtaat ccacgtgtcc ataaatagat gaatgaataa acaaaatgtg agatgtgcag  43620
ataacggaag attagtcagc cttaaaaagg aaggaaattc tgacacatgg tccaacactg  43680
atgaaacatg agcacattat gctgaatgac ataagccagt cacagaggac gaatgtgtga  43740
ttccagcttc ttctgcagct ggctttgcaa gggcagcctt ggctggtgtc cccttctccc  43800
ctgcagtggg agcgtccctc cccggccccc cagctctcat gctaggccgg acataagtgt  43860
ccaaacagat ggagttctgg ccgctgctgc ctccagaggt ggttggcctg gtcagcattc  43920
tggggactgt ctgtgccttt cctggatcgt tcgtggagaa cagttgacat cagcccagac  43980
ccaggggcct ttgcaaagga cagtcatggc ggcccccgggg caggggggctg gatggctttg  44040
ggactggcct ttgaggggaa aggtggcttc cccaagcctg gcttagctgg tcaaaggcca  44100
ggtgctgccc tgaatggctt ccaggccccc ctgtcatgag cctgctaagg gtcagcactg  44160
ctgcaattag tctctttgcc agcaagtttt attcaactct tcgttcctcc atgtccctga  44220
ctgggaattg actcgaatgc ccagagttaa aagaccaaaa gttacgtaac gtctcccagg  44280
gatgatggca gcttatgagc aaacatgttg attaaacact gcggcaagtt gagactcggt  44340
gattgcctcc gtagctaaat aacagctcta gtgcgggtga ggaggagcct tttgacacgt  44400
gtggcagtta actttgttga agaagtgagc aaggtgactt atctgtagga agaaaaataa  44460
aagtgcttgt gagcaaaata gggcagaaat aatgaggttt atgatggcag aaaaatgtga  44520
gaatcagaat tgcggaaaac cgtgtatcga gcacttacta cctgcctgct gggtctctgc  44580
tagctctttc acacgtaaat atcgcgttca aatttcggag caacccttca gggtggtggt  44640
tattagtctc ataaggaaac tgagagaggg taagcccagg tcacccagag ggaagggtca  44700
cattagatgc agacctggat ttggccaaaa gctaaagcat cccagaccca gagaagggag  44760
tggaggagcc cgagagagaa tcccagctcc caggaccacc agcatttgct gaatgcccac  44820
taggttctag acactcagct aggctctata taggtgattc ccattgattc ctcatgactg  44880
tcttcgtatt tgatgttctg tggttgtaag caacagaaac acactggagc aagctgaagt  44940
agaaaaggga actctttatt tcgaggacaa agtggtgtct cctaaaccca cgaacaggag  45000
acagcaaggc tgccagggtt gccggaaagg agaactgaag ggaagcaaag gggctgggag  45060
gctctctctt gcactcctgc cttatcttct tgtgtaaaga tatgaaaatg gccacagcat  45120
ccaagtccct ccaggtctcc acctgggcca gtcaactcta ttgaggtcag actatagcag  45180
actaaatggc tatgaatgag gtggaggcag ccaaggagtt gtgagtcggg taggctttag  45240
tcctacttaa cttttaaagg taagtacctt tatccccatt ttacacataa ggaattgaga  45300
ttcccatgag tcaaatgtcc ttgtccaagg tcacatggct aatcttggtg gaggggtagg  45360
aagggtttgg accaaatcga tctgactcaa aacccatgtt tgtaatcatc atatagaact  45420
gctgtagagg accattagtc ttaaatttac cctttaatca agctagaaaa gaaaccagga  45480
tggtttagcc tgagaagatc aacctgaggg tctgtatgat atccagtcca tcttgatttt  45540
aaaatccttt ttggaggatg gtgatcaact agcccttctc tacagccaag aagcaggcct  45600
ccgataacaa tgtccccatg ctcgagcccg gacagacgtg aggacaagct ggtgctacag  45660
cgagggccag cccttcttga aggccagggg ctggggcaca gggctgctgt tggttccatc  45720
cggtcctcaa gctgaaatct gtcctgacaa actgcccctg gcagaaaatt gggacacctc  45780
```

ggaggtttag atgttctcat ctgacccttt cacaatcccc aagcagatgg atccatgtgt 45840
tttctttggc tgtcctgttg cactggagag tgagtgttca ttcttcgata tttcagttta 45900
cccatggggt ggagaggatg gggtttgttt ataaatgaat gttttggtgt agacctgact 45960
tgacaccaac ttagctactt cagggattct tggccctaaa cgaacattca tttctgtcta 46020
aaaaacttgg ccatgatagt ccaaacttta aatgatgtta atttaccgtg agatgtgatg 46080
gagtatgtgg tccatgggaa atatgactta gtgttattta tctaaaaatg agtgtctgaa 46140
tccaccttca cgtttataaa cactgcacac atgccagaga tatgaggagc agggtgatgg 46200
agggtgtgtt tcctctggga gaatgagccc ctcagataag gggagattc ttgtggggtg 46260
gaagattttg gaagctgttc gtgagactat taattgatgg cattctgctt cttgtcttgc 46320
agattggaaa cctggaagat tactaccatt tttatcacag caaaaccttt aaaagatcaa 46380
ccttgagtag cagaggccct cacaccttcc tcagaatgga cccccaggta cagagtgtcc 46440
ggatgctttc ctaagggctg gagggtttgg gtctgtggtc ttaaaaatgg cggagtctgg 46500
attttaatgt gattctggat agacatgagt tttccatatt cactttaaat acagcaagac 46560
aggtgtagct acgaatcaga ccatctgaac taaatcatgt gagtgaggat ctctcagcat 46620
tttaaaatca acaaaacaca atactcacag gagatacata tatgaatctt acccatgaaa 46680
caaaaactct aagcaattca agcaagtatt ttaataatga aattagagat caggcaggtg 46740
gatgtttttg tggttgtcat aacatgtatg ttaatggtta ctatgaattt gaaaactgag 46800
gcagtaacta tgactttttt tcctcaaaga ttcacatgat cttcaggatt aaaacaaatg 46860
cgatttgaaa ggaggctaac attttaaatt ttaacataac ccgtatttat tgggtggtta 46920
attatacttc ctttctgcat agatttgaaa ttaatatttg agaaagatca atcaacagtt 46980
atgtgtcaag attaaaaatt taagatggcc aagtgagcct ccagtgagtt cattcatttg 47040
gcaggtattt ttggaatacc ttccatgtgg ctggctctgt ccatagcagg gcccgtggag 47100
ctggcggcag ggctgacaga aaacgaagca ggaaatagaa aaatatgtga tatgtcacag 47160
ggcgatgagt gctgagaagg aaaatgaagt tcacgtgaga agcagtagca gccccagcaa 47220
ggaacggagg tcattggtaa atcatagttt taggtcacag aaatcatctt ctcttaaaag 47280
ttaacgtata tactagatgt ttgtttgggc cccctggctg gtgcacaata ttatttcagc 47340
tatttccaga aaatacttag agtaaagttt ttatggaaaa atgggttctt ggtgttgccc 47400
caacccacct gcttcaatga caatcagggc tctttttgta ttgactgagc agggatctgt 47460
tggagagacg cgttatctct gggctctgta cctgaattat ccttctctgg ggcatcgcat 47520
ggtgagggtt ttgatttgaa gcatatgagg aagtggtccc catggagctc acccatggac 47580
ctgggctgtg aaaagacaga cttgtcttga atatatttct ggattggttt tataggtggg 47640
tggatggatg gatgaatgga tggatagata gatacggata agtcgaacga gatagatatg 47700
aaacattgtg ctaattccat tattccttca tagcaaggga aggagttaag tgtttactaa 47760
gggatggctg tgcttgggca ctttacatgc accgtctcac cccatcacat gggggtgaga 47820
ttacgtctac ttgtgcttac accatggaac atgaaggaat gtttttcaaa ggggccagta 47880
tatttaatcc tctaggaaaa aagccagatt gtagttgctc cttcccaaag agtggggcac 47940
ttggggaagg gtggatcagt agaaaactga gcagcaggga gcctctgtac agggtgcata 48000
ggctgatccc ggaggaggcg tgagttctgt gcggttgaga gaccgtcatc tgtcatcttg 48060
gaggaaattc taagctagga aagaggtcga cgcagcatcc ctccacactt tcactttaag 48120
caagcacttg atctgccgtg tgaagaaaca tcctcattct tcaactgaag tcttttgagt 48180
tgttgaattg ccaccacgcg gatagttaca atgaaagcaa gctgtttgca tgcaggaagc 48240
ccatctcata agcatgctct gagaagagac ggggaccgtg gatttcttgg tcttctttcc 48300
atgaggcctt ccaagaatta ataaagcaga ttcttaatgg ttagaactaa ggcagagtcg 48360
aaataggaga cttaatctgt gttttgacta catcctctgt tgttggtgac tatattttaa 48420
aacttttaaa ggtactcagg tcgactgctc atcccttcct tccaaaaata ttaatggtgc 48480
acctgctgag tgcaggaccc tgtgcctgag taatgcagag ctgcccagca ggtctctgtg 48540
ttgctgagtt ctcggtgaag atggggatgg gagacctgtg catgagcaag gcaggctgag 48600
gcagcagaga cagactctgt ggggggcttg agggccacca taccctggac ctgcctcctc 48660
tctgcagcac ctgagctgct tgattgaccc attttaggtg tgttaaaagt cctatattca 48720
gtttgggtct gagggcaaag cattcccagg cattagttgt ctcctcgaag tcagcagaag 48780
gaaggataga gacttcctag gcaaaggcta acgtagcagt taaatttttt caaataaaaa 48840
tctccttctc acagagcttc ttaataagct cctggcaagg cttctatcaa tgcatcctgc 48900
cagtaaagaa gaaaggaaga aaggtaaaca gcctgggcat cccaggcctt cctggaacgt 48960
tcctaggatt ggctgattgt ttctcatagt tctaattaaa ttgttagccc cagggaaagc 49020
acacagacat ctgaaccgat tatgaattca gaatcgcaac tgaaatacct ctgtttaaat 49080
ttgtctagct ttaatgcaaa ccaaatcaat tagctgtcag tctgactaat atttactcca 49140
cccagtcatt acaattaaac acttggtgaa attagctgtt ttatggaagt atttagtgtt 49200
atcttttatt gcagtgcatc agaacgtttc cctacgttgg caaagcattt ttatgatacc 49260
ttcacatctg gagagttgtg taattaatat tattaacaaa aggaaaagat gatttaatat 49320
tattcagaga cttcggaatg cgaggctgcc attgtgttca aatgaccaaa ctggaaatga 49380
atgttatggg gcttaggata aagttccatc aaatgcagac ggtatcttat tttaattagt 49440
tccagtccct attgtatagg agtgctttga taagtgatgg aatgtacagt ccaccccatg 49500
tcacataaaa gcagatagaa tgtacatttg ggaaagcaaa acaaaactca agggggtgtc 49560
agcagcagga ctctgttaag cacgtgtgtg cacgcacact tattaggcat cttcttcgca 49620
ctgatcctgt accggaatgg tacagtcatt ttccttgcat tcttaattac ctttacttga 49680
tgtttttctt accgtctttg aaaagggcca ttttgctcag attgctttgt tactcagccc 49740
tgtccttgga ggaacagccc aagtgttcgc agtgtgcagt tatcggtcgc tgggtttttc 49800
caaggcttgt catttaagca aactgaaagc atttgttttt aacttgttct tttgccaaaa 49860
gtctggagaa gggtggatat tacagaagcg tcgaccaatc actgaaaggg ctcacaaatt 49920
tttttaaaat tacttgttct gattatgttc caagctggct tatagttagt cgttgctgcc 49980
tgtgtcttcc agaccttaca ttttagcatg atgacttggg ttcagctctt ttccttccct 50040
acagatctca gccagattgg tgatggaaat ggaaggataa agatgttcag agggagcctt 50100
ggtggctcct tctagggccg taggaggctt gggttcaatg cttcatttca gtgctttaaa 50160
gcttagaagt tgcaaaatga ttgcaaggac cagaggaggc attctgtttt gtaggatggg 50220
actttgcccc cggagtttaa tcaaagctcg ggtttccttc cagcagtgat gcaatgttga 50280
agcagatctt tccattaacc acagatggaa ttttatctaa cagttttgtg tgctagagca 50340
attcaaagtg caaacaaaca gaaagttcct gacaagagca catagacagt aagtgaccac 50400
attggtctca ggggttgatg aactgtgtca tgggctgagg gcagggccag gcagctgccc 50460
agggcccaga ggatttgccc acgtggggac ggtggactgc tcccccatga gggtgatcga 50520

-continued

```
atgacagtga caagttggct gttcacattt tcagcaccac ccagctggtt ctagtggcat  50580
ggctgctagg aattggtaaa aagtttgaat gtgtaaattt accttaaaag acagcatttt  50640
attctttcac gacatgctct gcccttccgc ttagatatct caaagacaat ccaaagtcag  50700
tatgtcccaa acccagctca ctgtctctga ccctagtctg tctcagaggg aagcgctcat  50760
ccgcattcca ctgcagtgcc agcggcctct ccttcccccc tacacttgtt ccacctcccg  50820
tacaacctgg ccctgccatg tcctgtgtct cctgccctag gcccagctcc tgtcatctct  50880
tgcctgcacc actgcactgc cctccttgct ggcctcatgt gggcatcctt gccccggcca  50940
gtcacctccc atgctcctga gggatcctct gaaatacggc caccactggc ctttaagatc  51000
ctcctcgggt gactttcgct ctttttccct ctgcagagct tttgcacaga cggctcccca  51060
ccttcccctg ctgttgctct cttccccacc ttcccctctg ggctccaata tccctgccac  51120
caggaagcct gctcagaggc tgcggacttg gcctgctctt ctagcagtcg tatgtttgta  51180
ttctagatct ggccctagag taggagcaca cagcagtgtt tgttgggaac gatgactagt  51240
tcagtttgtt tgggatctgt cagggacaga cagagtcggc aggggagctg caggtggttc  51300
ctgggggacc tggatcgtca ggcttgggag ggcgttcagt gttccagaac cagaggagag  51360
gcgatgggaa ggcggactga cgctgctgtg cggatgcctc gggagagagg aacttggagt  51420
tcaaagcatg caagcccatc tcttgccaat gcaacaggag gttatcgagg gtcaaggcca  51480
catatcattt gcttttactc ccttacaagt ccagcagcaa cccagagaac agtagacaat  51540
gcttcctgaa gcatatctca agttccagag atgtgactcc tataagcaag ttgtgtgtaa  51600
cataagcaac ttctttctat gtaaatactt tagaagtaaa ttctgaccca ccttggctaa  51660
attatggaaa aatcctaaat atagttttca gttgacaaag ctgtatcctg tattgctgaa  51720
gctaaaataa cagaggtaca gacagtgact gcatgtcaga cacgttgagc agtgttggac  51780
ctcatagttt gttagtctgc gggggcagtt gtaacaaagt cccacaggat gcggggactt  51840
caaccgcaga accgtattgt ctcacactta ggaaggttgg aagactgaga ttacggcgtt  51900
ggcagggttg gtttcttctg aggtctcttg atcctcacgt ggttgtccct ctctgcgagt  51960
ggctctgtcc taatctcctc ttctcatggg acactggcca gattggatta gggtcccccg  52020
catcatgacc tcatattaac gtaactacct ctttaaggcc cttatctccc attacagtca  52080
cgttctgagc taccccgggt taagatttca acataagaat ttaggggttc acaggtcagc  52140
ccctaacaat aggtgaagct gggctccagc tgcctcttct gttgtcagtg agtggaggtg  52200
ggtggcgggc ggtggggaga ggggcacctt ctgtcccctt tcagcaaaat aagaactaac  52260
ttacaaatga gtagctttac tttcccaaag agctttcaca cgcactgtcc catttccgtc  52320
atcggcagag cgaggacttc cctctctcat gactgttaag caggggtctt ctggcacctg  52380
tagtttaact tcaatggaaa gaattcaaga aatggtctct acgctgttgc agttatggct  52440
gcaggggagg cagtggggag ggagctgggc tcgcagctgc ctggatgaca cgggaggtgg  52500
tggtgggggt ggctttctag gctgagttag aatgtccttt attttctggt tcctcctccc  52560
cctcctctac tgcccgggct tactcactgg gttcccgctg tgtgtttgcc atggcagcct  52620
ggggtttccc ggccccaccc ctaggtgagc cagtgctgcg ccggaggtgg gcctgggcat  52680
ctcgccatga tgggctctca cgaaaccatg taatcgtctc tcacttgtca cgatggccct  52740
cttgccctgc tggaagatga cagccacagg accaatccct cactcggaga acttggatct  52800
gctttctgcc tctgtctagc ttggttcagt ggttcttagc catttggggg aatcacaggc  52860
```

-continued

```
ccctttgaaa agctgttgga agttgtgggg cctctcgctc tccagaggaa aaaagacatc  52920
atgctcatgc cggcaccatt ttgcatacag ttctggggtt tctgggactc gagcctgtcc  52980
ttccactcct tgagggactg tgggatccag ggcaagatgg ctccagtgtg ctgcatgaat  53040
cgtcgcctgt cagtgagaga agggccacgt tgcacattat gcagtgacgg gcacttgtcg  53100
gggagtggga tttttctttc tttaaattca ccagtcagct ttctcactga gctctttagc  53160
tggttggatg ttggcccagc gaggtgctca gagcagtcaa ggttgatggg aatcaagatc  53220
taagcgccac agactgttga gtgcacaagc tctgagagag ggaccggtcc cagcccctgc  53280
tttacagtgt ggagggagag gcccaggcag ggtgcccacc tcccacacag agagaataac  53340
aggcttattt tctacggtgc cctgattgtt ctctcctgga ggaggctttg gagcttggtg  53400
gctcctgggt gccgaggtat ggcctccgac tccctccctt gatatgccct ggtggacagt  53460
caggtctggc ttgcagtccc cttgttcttt cacagttaca gaataaagta accttcgctt  53520
tgatgaaacc agggagaaaa gagaaaagaa agagctggcc gagctgtctc ccttgcgttg  53580
gctacaactg tgcagaacct gtgtgaacct ggtgtccgca gccctgccgg tgcgtacttc  53640
aaagaacctc agcagcttga ctcccttgat gctgtgtggg accoctggac cgctggggga  53700
gggtgcctgt gtatgccctt cgtggccttc cctccatctc agagcaaaga ctgaagcccc  53760
tctcctttta ggactctcca gctcccaaga acttctaggg gccttcctga gccacagcag  53820
ggcccctctg aataggcaca ggcttgaagt tagggcagaa ggacatggtg gctttgggtg  53880
gacgtgcaag tgggagggat ttcatgctct ctttggtgac actggctcat gagtgaaagt  53940
ttcaaaacac cctcccctgt cgcttgtcac acctgggaat gatatgtcag caagcttctg  54000
gcccacctgt ggcccacagg gaagaagaca gggccaaggc tgcccatggc tgctcgctga  54060
aaggatgctt ggacaaggat cacaactcgg tggcatggac agcctgcagc atggcaagcc  54120
atttactgga acgcgggcag ggccccctcc tgggtctctg cttgtttatg ttacccttta  54180
ggaacatcct tagattttac ctcgtcttat caacagaggg acagtcaacg gatgcctcat  54240
tttaacttgg cttctcgaga aggaagctgg aggaagcaca cactacaaaa gaaagtgttg  54300
ctgcgcacct gtcttgagaa gacgatgaag ccttcttcat gattagaact ccctgcccca  54360
gagcgtagct tatctataac tgtgctgcat gtttagcagg aaacatacat ttggaaaata  54420
gagaaaagga taaaaaggtc agagtgaagt tctatcttca aagtatgacg ttaaagaaat  54480
cctggcactt tctacagatt tgcagagaaa gacggtttct gtttgggcta gaagtggcat  54540
ttggcaaacc ttgcctttgc cccaaatcac ttatagttga ttttccacaa gaaaagtcaa  54600
cagatgtcat ctagcagtca tttagaccta atcacatttt ctttctttct ttctttcttt  54660
cttttttttt ttgagacaga gtctcactct gtcacccagg ctggagtgca atggtgcaat  54720
ctctgctcac tgcaacctgt gagggttgct tccattcgat gggagggctg gagttttagt  54780
cgcttggttt ggggctggtg acacacctct gacctccaca gagtgtccag gtggctcctg  54840
gtttcacccc gagggggcat tgaaggcaga gctttgcatc ccagctgggg atgggagggg  54900
gaggcacttt ggtcctggcc gggaaccagg tatgttcatg ctgatcttcc cagaacctag  54960
cgccagacac acaggaagac tcagtgcatt tttgttgagt gagccacaga ataagtgacc  55020
ccaggatgcc tgctctctgg agacactggg gaaggtgaac ctggaaaatg gctttctctt  55080
tgtggtgggt aggaggtggg atccgggatc cccttgtgct gtcctggagc tgggtgagaa  55140
gcaagggagt gactggaacc cagaggaagg gacacagtgc cgggagaatc agcctctgcc  55200
accgcgctgt ctgcctgcat cccgtctcca cggagaagcc cccacgcctg gtcagtcatc  55260
```

tgttgtacag tgttcggttc cattggcctg agagcacctc acttgccgtc agagacttac 55320
aatgagcagg tgtgttagca gagagagggc tgcccctgcg accacgacag agagagagcc 55380
ccaaactgtg ctgcgggccg caggctatca cagtccccct cagaactgtg tgccagtgtt 55440
gtggggtttt gcccagagcc cagcaaggac caagggccgg gatgcccagg ctcttccatc 55500
ctgctgagga accctcttat gacttctggc tctacgcttt cccacatctc ccagctgatt 55560
agtggggtgt cacccacttg ggcttggaag ggcagagtgt gcctcctcct ctgactggaa 55620
gtgtggtctg gtgggcacag caattggaag gggctggatg ttgttagaac agagagttca 55680
gggcccctta gcacaaacag ggctcagcct ggcaggaggg cgggacatcc ctgggagctt 55740
tgggctgtgc gggatctaca taccactgta ttttgtaata gcgtgctgaa cagattatga 55800
aatattgttt gcggcatctt agaccaggta aaaagccttc tagttcaggc agtaatatat 55860
ggggacattg caaaatgcca tcagccggtg ttaggaacaa aatatctcat tttatagttt 55920
tattttctgt ggaagtatct gtcagcggcc attataaatt atctaggact tggtgctgag 55980
gattttttaa gtgtgtgacg tgaaactggt tttgagccct ttgcagtgtt tctaaggcgt 56040
ctggtctgct ggtgttttat agacgaatta catcggggtg ggacaggctg ggatgcctct 56100
cttccggcat tttgccctgt acaccaagga tgtcttggag gccatcccca gccctaaatt 56160
tgagctgtgt atgcaggtgc tccgctctcc ttgctcaggg tgatgtgggg aggccaaggc 56220
tcagggagga ggaagagaaa tcttgtccct ttgctcttgg ggactgttac tccctgccca 56280
ctcagcctca ggtagctctg ttctagcttc cagcacgacc ctgggtcgcc agccttgggt 56340
caccttgggg ccccgccccc ttctcttgtt cctcccctgc ctctagctgc ctcctccagg 56400
cagcctgccc tgtttggaac tcacatcatc ctctgattgg tgggatcccc tgaatgtagt 56460
gcagactcct cgagagcacg gccctggcgc ccatccttat cccacccatg tcaggcccca 56520
gagccaggct gaaccccagc tttgagcatt attcaatcag gtggagctgc cgtggtaaga 56580
ccaaagaaaa cattcccact cagggtccaa gaagtcttta ccccaagatc cttttaaaat 56640
gaaaaagttt ttccagcttg aaaagaatgt gtacacggga tgataagagc aggagtgctc 56700
caggcactgg tctgagggct ttatatgtgt tgtttcttat attaaccctg tggcaaccca 56760
tgactgtccc cactgtgtgg gtggacacca ccctgaggcc atggatgtcc actgtcagct 56820
ccaagtcaca cagctggtga gcacggggct gggttttatt gcaggtggcc tggtgccttg 56880
atccttggtc ttaaatatca gtgatacagc cttgtgaact tttttccttg atcgtgaaaa 56940
caaatcatgc tgattgaaag acatttatga catcctgaaa gtaattgtaa aattttaaat 57000
tagcaataat gtcaccaccc aggaactgat gctactacta ttttgctgta ttcctttcta 57060
gatttttctc tgtgcatgtt ttggtaccat attgctggtg gctgccaaat attccaatat 57120
atggcttacc atatttactt atgtccttac tgtaaagcaa attccaatac cagttaacca 57180
aacactttct tcattcactg ctttcccatg tgtgtatttc ctttttcttc aggacaagga 57240
tcaccagata atttatcggc aatttcacaa ggctggcttc cttccttctc tccctctctc 57300
cctcccttcc ttcttgtctt tctgtctctc tctctctctg tctttttttt tttttgacag 57360
ggtcttgctg tgttgcccag actggagtgc agtggcacca atcatggctc actgcagcct 57420
tgacttccca ggctcaagca atcctttcac ctcagtctcc tgaggagctg ggactacagg 57480
catgcgccat catgcccagc tagatttttt tttttttttt tttggagagg tggggtttca 57540
ccatgttgcc caggctggtc tcaaactcct gggctcaggc gatcttcctg cctcggcctc 57600

-continued

```
ccaacgtgct gggatgacag gcgtgagcac tttctttctt ttagtacaac gacttcaaaa  57660
tctatcagag tggtgttatt tcttcctctg tatacacaaa caacttctca tctttcaaat  57720
gtagtcactt tgaagtgaaa atgtccccag gaacttacca tctaaaatat ctgctatgac  57780
acagatattc acgcacaagg aaggctgtag cacctgcaaa gaggctacat aaaatcaaga  57840
aatcatttct aatataaaca gtaattgcat ttcttctggt aggtgaaatg gctccagcaa  57900
caggaagtga aacgaagggt gaagagacag gtgcgaagtg acccgcaggc cctttacttc  57960
aacgacccca tttggtccaa catgtggtac ctggtgagta ggacaggacc tctgtctgcc  58020
ccaggacact tgcactgcca ggtctctgaa atgggttaat ttccctcaac aaagctaaat  58080
tcaaacaaca tctccagaca gacacacttc accttgaggg tgtaaaacca ctaccgcaag  58140
gctgtgcagt accggctttc ctgtggattt tttctgaaac tttgtgcagc acactctggg  58200
atgggggctc tttgagaagg gaagtgattt gatgcaggct gtatgactaa atggcaaagc  58260
ccagcccatg gacagagctc ctgctgggag gcgatgccct gggaaaatat agattgcagg  58320
tgcagaaaaa gcaagggagc cgtctgcatg attctcgatc cgagtgggaa agaggagctc  58380
tgctatgtaa ggcagggata ggtgttccct cctttttac ttgcaagcct aagcgcctcc  58440
ctgtggggtg tgcaccgagt gtcagttctg catctggaat gtccatgtcg gggggacttt  58500
gtgtctttcg tgcttacagc attgtggcga caagaacagt cgctgccggt cggaaatgaa  58560
tgtccaggca gcgtggaaga ggggctacac aggaaaaaac gtggtggtca ccatccttga  58620
tgatggcata gagagaaatc accctgacct ggccccaaat tatgtaagtc aatcctcgga  58680
actgacatgc aaatatattc aactgtgctg gtcattaagt aaatgcaagt ttaaaaacag  58740
taaggtcccg atctccccca gcccccatta agttaggcag taaagaaaac tatgctggaa  58800
agaattagga agatgaatat tctgctactt gctactgtca ggggcaaggg ttttgcagag  58860
ggattcatcc acatgcttgc acagtcacat acacttttag gaatggagcc taaagaacta  58920
agaaatgcat ggagggggat catcagcgta cagatagtag caacacgaac agtgacaggg  58980
tgacagtgtg aaaacacggg ctctaggccc agagtgcctg ggttcctatc ctgggtctgc  59040
aaatgattag ctctgagatc ttgagtaagt tacttaactt ctctgtgcct catctgtaaa  59100
cattttaccg tctgtaaaat ggttcataag agaacgactc tctcacggag ttattgtaag  59160
gactaaatta gttaaatgta aggacacaag cttggcatat cgtaaatatc atagatgcaa  59220
gaaatactct aagggacttg ggcacctacc ggtgattaag taaaccatat tgtatccatc  59280
tgacagatcg ttatgcagcc cttagaaatg aattttgcag actacgtgtc aacaacactg  59340
gaaacctttt atcatatatt ttaaaaggag aatgtaaaat tatgtgaata ctgctgttac  59400
agtcatataa acaaaagcat acctattgaa aatataaaat gaaggaaatc ctgacccacg  59460
tggaaacgtg gataaacctt ggacgttatg cgaagtgaaa taagccagtc acaaaaggac  59520
aaatactgcc tgattccact tacacgagtg actcggagta gccaaactct tagacaaaaa  59580
ggtggagtgg gggttgccag ggcctgggag aggggagtgg ggagttagtg ttgagtgggt  59640
gtggggtttt gcaggttgaa agggttctgg agatgggtag cagcgatggc ctcaagcact  59700
gtgaattaat gccactgagc cgcacactcg agaatggtta aggtcgtgta tttcccgtca  59760
catatatttt accacgataa aaacgtatat gagattatag ctatagtaag agaggagccc  59820
cgcgtgtggt ttctctattt gccaacggaa cataaaatcc atttcaaaca gagctgtcac  59880
atgccatttc tcctcactca ccacgattcc atttcttagg attcctacgc cagctacgac  59940
gtgaacggca atgattatga cccatctcca cgatatgatg ccagcaatga aaataagtac  60000
```

gtcacctcgc ctcatctccc cggcttctct tcccctccct gcagcgtcac tattgaatgt 60060
gtgtgcgagg gagctggaga ggcggtggct gccggcgtat cttccctgcc tgggcgcgag 60120
gcaggcttct ccaggagtca caggccatgc caggcacagc ccttcaggca cggccagctt 60180
ctgtggagtc agcctgttcc tctggggtgt caccgctgcc gggcagctag aaatgggtgt 60240
ttgacagaca tcgttcctgt ttccaacttt cttgaaatat tttaaaagag aaacccttaa 60300
gtctaaccgt ctccatgacc tgctgtgtga agacagcagt ttggtctgtt tgagcacaca 60360
ggtcacgtgc ctgagctttt gtgactctgt gaccttagga atgaggtgga aggggcatga 60420
gtaatgctgg atagacccag gttcagatcg cagctctccc acttactggc tgcgtgcatg 60480
ccgggtgagc tggttgaaac ttcatgtctt agtgtcttag aggctcgtcc aggccagtga 60540
tgtcccctac ctcacagggt cacaggaggg gtcagtgaga tgatgcatga ggaatgcacc 60600
cagcagattc ttccgaaatg gtgggcgttt ttgtgtcact gtcattttgc aagtggaggc 60660
agtggggtcc ggagagccca ggtgactttg cagtgtaaac ggcagccctg gggtcagtcc 60720
tgggaattca tttgctgtct ctttccttct ccatcagcat gccccatacc ctgagctctt 60780
atcattcctc taaaaatatt tagagggaaa taataaaagc tttttcttcc tccccactgt 60840
tgacaagact cttgctgagg ggcgtctccc gattatagtc ttttagtttg tggtcgcttt 60900
gattctgaga ttcacaaacg ggtgcgcagg caatgctgtg caggaagcct cggccactgg 60960
agttccacac agcaggctgc agagctcccg cgagcctgca gcagcccagc ctcatgcacg 61020
tcccaaggtg cccttcctgc tgccagtgag gatgcctggg gcaaaggagg aatgacccac 61080
ataccacgca gtgacccttg aagggcagga ttcaatccca tcccgagcca tccattgagc 61140
tctgtgaccc cgggaacagc cctggccttg aagctgtgtg gcttccaggg aaggacagat 61200
gactctcttc cagagggctg ctgcctgggg cgatttttaa aggcagcttt aaatttgaat 61260
caatgattcc catcctctgt ggactcttct caaagatgtg ctatttcaag ttgctcctat 61320
tttggccccc gctggaggaa ctgacccgac gtggcacatc agagaatggg gtcattactg 61380
aggaaaacgc atttgttttt ctggtcattt cttcatagtc tcccagctgc tgagtgttta 61440
atttagagcg ttcttcctca gctccagctt aaatggcctt agaagcacag gaagggctgc 61500
ctcagggtaa gcatggtgtt gtaggtgcat aggggatgag gcaggtgaca tcagcaccag 61560
actgttcctt ctttcatcct gccaggcagc aggtgtccct gctgccagcc acaggagaca 61620
cgaggccgag gtggcgcagc acccacccta cacagcagtg gccatgtgcc aattacacgt 61680
gctgggagga ggaaggtata ggaccacggg cactggggca ggcaccttcc tcccacatgg 61740
gggtcagggg aggcatgctg gaagaggtga ccatgcgtga gcacttgcca cattcaggat 61800
gccaggaagg gctgtaccca ggctgacttg gtgccttctc ccagagtggg gttggtgatg 61860
agaggggatg caggaaatgg gctttaatga catctctggg cttcggacaa ctgactctct 61920
tgttgcattg aactgagcca ggcactgaat tcactgaaac ttgctgggct gcgtcctcac 61980
ttggtttttt cctttgtttc agacacggca ctcgttgtgc gggagaagtt gctgcttcag 62040
caaacaattc ctactgcatc gtgggcatag cgtacaatgc caaaatagga ggtaaggccg 62100
ggcgtggcag cctgcgagcc gaggggcctg gggcaggggc agctgggagc tccctgtccg 62160
ctggtctcag cagcctcctg ttttttggct ttggccatgt cagcagaccc ctgggccaga 62220
cgcagcagtg ccgtctgtat catggcccag gcagctgacc cacagggatt ggggcctcaa 62280
gacagaggaa ctgcttactg ttttgcctga aaagccattg cagttcccat cagaaaggta 62340

-continued

```
ccctctctcc tctggtcctg ctggcctggc tgctgactcc tagaagtctg cgttgattcc  62400
ccgctgccca tagccctcag tggctccgtc acttcccaga cagagtgaca gcttttaccc  62460
gggaccagag ctttccctgg gttctgactc ccactcaagc ctgctggccc acttctcctg  62520
cccctgctct gaccttagag gacatttttc atagtgcccc ttagacacat ctggtcttcc  62580
cgattgatgc ctgggcttga accattccca tccccgcctc ccccgtcttt ccacttggct  62640
ctgtccacct gtgccttatg gcagcctcat gcctgctctg ttctgtgaag tgctccctgg  62700
atccagctgt cccccgtctc attcaccagg gaatcagctc ttcttggtcc ctttacggag  62760
cagcagccgc ccctgccccg cgtgcgtctg gtcttgccat ttagcttctc acactgctca  62820
gtcaagctgc ccttgctagg atgaggcttt ggagtaaagt attgaatgtc ttcctattcc  62880
ccacgggagc ccggcagtgt gacagctcag tcacccaagt gctctgaagg cccctctagg  62940
tgcatgtcac tgacccggga actgagcaag tgggggcagc agagaggagt gccagagggc  63000
ctccagggac tgcggcctca cccaggaggc ctgtctgctt ctcagtccga aggtgctcct  63060
gctcactcag gtggctgcag tgggaaacca ccttcccggg ggggcactgc catcctgcca  63120
ctgagccttg gtgagggtgc ctgcagccgc tttctgccgt tctgccaccg agccttggtg  63180
agggtggctg cagccacttt ctgccgttct gccaccgagc cttggtgagg gtggctgcag  63240
ccgctttggc tccacttatg agcagtacca ggcagggagg ttgggccacg gttccctgga  63300
tcaccagtcc ttgggggaat ttcttgtgtt tcgaaaagag ggtccttagc ttttacttaa  63360
ttaggactct gcctgccttt tcccgtggaa atcttgaagg tggcttggat tttcatttta  63420
tagcagaatt aacccccaag ggcgcgttct gcagaacaaa tcaggagact ctgtcaactg  63480
gcctggctcc tttgtggata gttcttgcaa actgagatat ataagttctc cctggagcct  63540
ttgatgatgg gtgcagagcc ctgagacgtc tctccaggat ctgtagaatc gggccaacct  63600
gggtgccagt tccattccca ccactcactg tctgtgtgtc cttgaacaac ttacataacc  63660
tctctgagcc aaggtttctt tacctgtggg gtgaaatgac caccaggcag ctgcctcccc  63720
agttttgtta tgaggatgaa gtcagatacc atgtgtgaaa ccatcggctt gggctaagtc  63780
tgcaggggat agctgagctc ctccttccct cttgctgaga ctctcagtgg gagaataaaa  63840
accatttgtg ttgctttgag tgaggggtgg accccacctt tggagttgct tgagccttgc  63900
tcccccaagt ccctagactt tgagcatggc atcctctggg agccgttaga aatgcagaat  63960
ccccacccca ggcctacgga gtcagggttt gcattataac aagatcgcag gggatttgtc  64020
tccacgtcac aatgtgagaa gcgctggttt agaggactcc ctggggtctc acaggtaggt  64080
aacacctgca tcatggattg cggggaggag tcagtggaag taacatgcat aaagatcctc  64140
ccagatgagg tgcacagtaa atacagcatt accgttagat agctctacac tcatcgccaa  64200
actctttccc tacgtttccc gagtcctgca agtgaaggtg ctccctccag atctggaaaa  64260
tgtagggata gaatttggca tgtgtttaaa acaagaataa tagcaatgca ctgtgggttt  64320
ataacgtatg aagcaatata tatatatatg tatataaaca acagcaggaa tggtaacagt  64380
catggtgaat ggaaacgctc tatcttagat ttatacatta tacagaaaat agtatactat  64440
taattccaga tagactggga taagttagga tatgcattat agtctcttga gtgacaacta  64500
acaataaaga catgaaaagg aagagctcta tggtcagctc cagggacatc ccagggaaat  64560
tccctgttgt gtgccagcac acacagagag ggagctgtgt tagagcacct cacccagagg  64620
tgggcttgga gggagaacca ggaggaagcg ggttggctgc ctgtgtggag aggctaaagc  64680
tgtttgcagc agctttggag ccagtggcta tcactggatc cttgggtcaa ggccagcctc  64740
```

```
aaccccacac ctaccttcca gagaggtgtg agctccacct catgtcctcg atctttatgt  64800
ggcctgctca ccccagcccc acgccgcaga cgtaattgtc tcctcagcac tctcacgggt  64860
agtcaagtcc tgccgtgtca agctcagcca caccctcatg ccctgctctc atggggtgcc  64920
tgctctgcca cccctggggc tcctacctgc ccctttaact tcaataggtg gttctgtgcc  64980
atcttccttg ttggttccct ccaaagacat gctgagctcc tagaggccca gaactgtgac  65040
cctcatctct ttcgtctctc tgtcagcggc atatccagta ttatacatgc agcatgtgct  65100
caaccatatt caatgcgtta attaaaaaat atccctgtta tcatgcatat cccaacttat  65160
cccagtctat ctggaattaa tagtgtactt tctatataat gtgtaaatct aagattgttt  65220
ccattcacca tcactgtcat tgtttgtgct gttgttttta tagattctac ttcacatgtt  65280
ataaacccac agtgcatttc ttgttttaaa catgtagttg accgcaaact acttatgaca  65340
agaaatacat ttacctgcct gtgtaccatt ccactgactg gtcttcctta ctttttctag  65400
cttcagattt ccatctttcc atttatcttc agcctgtcgc caggctcttt ggtatttatt  65460
gaggttatct ctcacctctt ttggtatttg ttgaggttca ggtatgctag tgaaaaattc  65520
tctccaattt tatctgaaag tggcttctct tcatttttct taaaagaaat tatgctgaac  65580
acgaccttct aacttttttt ttgtctttca acactttaaa ggtgttattc tgttgtcttc  65640
tggtatccat tgtttccgac gatgagtcga ttgttaattg ccatccttat tgttgttccc  65700
ttttaagaaa cgtgatttgt tcctatggct cctttttttt tttttgaaga gatggggtct  65760
tgctctgtca cccaggttgg agtgcagtgg cataatcata gctcactgca gccttaaact  65820
cctggcctca agtgatcctc ccacccgagc ctcccaagta tctgggactg caggtgaaca  65880
caacctttcc cagctaatta aaaaaaacac acaccttttt ccttgtagga tgagatactg  65940
ctgtgttgcc caggctggac tcaaactcct ggcctcaagc gatcctccca cctcagcctc  66000
ccaaagtgct gggattacag gcatgagcca ccatggccct tccctgtagc tgctttcata  66060
atgttatttt taaaaatatc tgtgctttgc ctgtggctct aacattcttt tatgtagttt  66120
tcttcgtatt aattccatct tgggttttct gtgcttctta gtgggttatt ctttttaaag  66180
aaaatttgga aaaaaaattg tcaatatttc ttcaaatttt tttaagttcc attttctttc  66240
tactctctgt gggcacagtt atagttgtta gattgcttaa tacgcctcac aggttactga  66300
ggcactgttc atttttttaa cccttttttc tctgcttcga atggaatgat ttttattgaa  66360
cttcaagtta actaatcctt ccttttgttg tgttcagtct ggtctttaaa aaaaatttca  66420
gggctgggca tggtggctca cacctgtaat ctcagcagtt tgggtggctg aggtgagtgg  66480
atcacctgag atcaggagtt caagaccaga ctggccaaca tgctaaaacc ccgtctctac  66540
taaaaataca aaaaatcagc caggtgtggt ggcacatgcc tgtaatccca gctactcagg  66600
aggctgaggc aagagaattg gcttagacct gggaggcgga ggttgcagtg agctgagatc  66660
ataccactgc attccagcct gggtgacaga gcaagactcc atctcaaaaa aaaaaaaaaa  66720
aaattcagat atttactttt ctgtcttatg atttccattt gactcttttt ttactgtttc  66780
cgaatccctc atgtgtctcc atctcttcag tcatgatatc tatcttttat tctagactct  66840
ttaacatgtt tgtaagaaat actttaaagt cttttgcact taattccaac atctaggcca  66900
ttttaggagt atgtttataa tgactgattt ttctctttac agtgggtcat gtatttctct  66960
ttctttgcat atgtctagta attttttatt gtatggtaga tattgttaca ttgtagagac  67020
tctggattct gttgtctttg aatatcatta agtttctttc ttggccaggc gcggtggctc  67080
```

-continued

```
acgcctgtaa tcccagcact gtgggaggct gaggcgggtg gatcccgaga tcaggagatt  67140
gagaccatcc tggctaacac agtgaaaccc catctctact aaaaatgcaa aaaattagcc  67200
gggcgcggtg gcgggcgcct gcagtcccag ctacttggga ggctgaggca ggagaatggc  67260
gtgaacccgg gaggcagagc ttgcagtgag ctgagatcgc gccaactgca ctccagcctg  67320
ggcgacagag cgagactccg tctcaaaaaa aaaaaaaaag tttcgttcta gcagttggtt  67380
aaatgtgagc ttgtggagac ctgattattc tttttttaa tgtttgctat ctttctgatt  67440
ttcgcatagc cttagggaaa atccattagc cctagcatat ggtctttact cctagaccat  67500
gaccctttg gtatttcagt ggaaagcctg aaatgtttaa acccagacct ctaacttagc  67560
aagtctgaaa ctccagatgg actgccctgt agtgggcagc agctgaaata cctgctcagc  67620
tcctccagcc tctcagctgc tgttttccta ctggacttct tagtgggttg cccatgtata  67680
cttcagggtt cagccaagtg gttgtgagga gtttatatgt tctcttctgt agatctctcc  67740
tttctgaaat ttctcctctc aatttccagc agctctgaca gtcccaactc tatcccctga  67800
ctcctctgga gaataagatg acattttact gtacttcagt atttgagttc tagcctctct  67860
gcaccaaaag aaatggaaag ttccctcaag aggaaaagtc atgtcaactt ggagcatacc  67920
cagtatggtt tgtcaagaat tgaacccct gcctacctct gcccttttct ggttgttctt  67980
cagtggtctt aaaaagttaa ttttttctaa gtaaatattt tttcagagtt tataattatt  68040
atctttaata agaagagtta gtctgatata agcaactctg tcattgttga acttaaaact  68100
tgtggtttat agttatcaat tagattgtgt attagttatc tattgctgag tggcagtcat  68160
tctaaaaatg cagctgctta aaacaacaaa cacttgtttt ccagcacaga tagtggcttt  68220
gctgaatgtt tctgattcag ggtcactggt gaagttccag tcaagctgtt ggctgtgatt  68280
gtagtctgaa gacttgactg agtctggagg attcacttcc aagatgggtt acttatgggg  68340
ctgttggctg gagtccctga ttcctcactg tgtgtacctt tccagagggt tgcttgagtg  68400
tccccataac atggtagctg gctttcttta taacaagtga ttcaagagaa aaagcaaaac  68460
caaaccagca atgtctttta tgacctcatc tcagaagtca tgtaccatct cttcagccat  68520
actctgtgca ttagaaatgg atcactaagt ttaacaatac actcaagggg aaagaaattt  68580
ggtcgcacct tttgagtaga aaggtgtcaa aaaacctgtg gacatagttt aaccaatttt  68640
ctttgtaaaa ctgcacattc cttataaatg ttgtcacata aaaataatta aatcaactga  68700
aagaaacagg aactgtccaa attatatctt aagaaatagc caggcgtggt ggctcatgcc  68760
tgtaatccca gcactttgag aggcggaggt gagcagatca cctgaggtca ggagttcccg  68820
aacagcctgc caacatggtg aaaccctgtc tctactaaaa atataaaaat cagctggatg  68880
tggtggtagg ggcctgtagt cccagctact tgggaggctg aggcaggaga attgcttgaa  68940
cctgtaaggt ggaggtttca gtgagccaag atcgtgccac tgcactccag cctgggcaac  69000
agagcgagac tccatctcaa aaataataaa aaagaaacaa aactccttca acccccagtt  69060
tccctaggtg tgttgccttc aggtgcatta gcacctaccc tggggagaaa ttttacactg  69120
tcaggaatcc acagaggcat gtgccatctt cattgtttcc agagaggaga gtggggtacc  69180
cctgtgcggt cactggtccc tgatgtcttt cattttagag agactttaat tttatattaa  69240
gttgtcaagc tgtacattga tgatttgtgc cccctttca tatataattt tttaataaaa  69300
atctgtttaa agtttttatg ggctgggcat agtggttcac acttgtaatc ccagcacttt  69360
gggggttgag gcaggaagac cttttgagcc cagaaatttg agaccaacct ggtcaacata  69420
gtgataccct gtctctacaa aaaattttga aaaatttagc cgggcatggt ggcatgtgct  69480
```

-continued

```
tgtagtccca gctacttggg aggctgaggt gagaggacca cataagccta ggaggtcgag  69540
gccgcagtga gccatgattg cgtcattata ctccagctgg gtgacagagt gagaccctgt  69600
ctcaaaaaaa caaagtaaag ttcttatgat gtcacatttg ttcatcttcc ttcatgactc  69660
ttgagtttgg gatcttgccc aagatagtaa acctgttttg tatttcctct aaaaacttag  69720
ttttaggaca ataattggtc ttaaaatttt tatggttttc tctttcctgt ttagcttttt  69780
tttttttttt ttgagacaga atctcactct gtcacccagg ctggagtgca gtagcatgat  69840
ctcagctcac tgcaacctcc acctcctggg ttcaagcaat tctcctgcct cagcctcccg  69900
agtacctggg attacaggtg cccaccacca tgcctggcta atttttttgt atttttatg  69960
taaagacggt gtttcactat gttggccagg ctgatctcgg actcctgacc tcaggtgatc  70020
cacctgcctc agctgcccaa agtactggga ttacaggtgt gagccactac aaccagcctt  70080
tctgttcagc tttttgatcc atatggaatt tatttctgtg agtagtgtga aagagagatc  70140
cccccaaatc aatatttggt gattgccaca cgtggccctc atcacatcct agatccccat  70200
atggacactg ggtctgccct tacgtttcct tagtcagttc cttcataagc cctaacaata  70260
ccacgctttg aattattaca gtcagtttag gagagttttg ggttttgtt tttgtttttt  70320
tggtaactga tagggcaaat tttctcttat ggttcctttt caaaaattac ttggctattc  70380
ttgcacattt tctctttcag atgaacttga gaatctgctt gtcaagttcc attaaaaaaa  70440
aaaaagccct gttgggattt tgattgggat tgcttggaaa ttatagatta attgggggag  70500
aatgacatct ttacaatatt gagtcttccc acccaggagc atggtatgtt tttatttatt  70560
caggtcttct tttacattgt tttttaaagt tttatcactt tctccatatc gattttatac  70620
atttcttatt agatatatat ctagattttt taaaaatttg tatttctaat tggtcattat  70680
tgaaacggat ataggaaagc tattgatttt tgtatgttgg gttttgtttc tggtcacctt  70740
attgatctct gtgggtgctg ttgtttttcc gttggattct cttggctttt ctggagagat  70800
gttaaataat agctatctgt aaatataatg gtggttttat ctctttaata ttaataactc  70860
tctttttctt gccttatttg aatatgtagc agttcctgat gaatattgaa tagtggtggt  70920
ttataggttc tgtttgattt ctgacttata caggaatact tctaatttta tgccatttgt  70980
aaatgtcttc cctgtagtta ccctttatca agttgagaaa attttattat attcctagat  71040
ttctaagaga tttaatcagg aatggatgtt gaatatttaa aagtatctat tgagattatt  71100
atattgtttt tcaactttat tgtttaatct gtgtagtgta ataagttaca ttaatagatt  71160
tcctaaactg ggctaggcac agtggctcac gcctgtaatc ccagcacttt gggaggtcaa  71220
agtgggtgga tcacctgatg tcgggagctc gagaccggcc tggccaaaat gttgaaaccc  71280
tgtttgtact aaaaatacaa aaattagctg ggcatggtgg caggcacctg taatcccagc  71340
tactcgggag gctgaggcag gagaatcgct tgaacctggg agacaaaggc tgcagtgagt  71400
cgagatgaca ccactgcact gcagccctgt aagactttgc ctcaaaaaaa aaaaaaaaaa  71460
aatcctaaat tggaaacttt ttctttcatt tttgaaataa gttccatttg ctcatgagta  71520
ttgttgtttt gatacatctg cattcaactg ctgatgtctt cttatggttt tacaacttca  71580
tttataaaat ggatagaatc acagtttctg tgttttgtga tgtttctctc taacttgttt  71640
atcagagtca ggccagtctc gtagaaagag ttaggaaact ttcttttcct gtgctctgaa  71700
atagttaata tattgtggat agtgcctgat ttctgaagtg ttggtagagc tgattaacta  71760
gtctgattgg atatggtgac tttcaaaagg actagaccta ttcaggtttt ctgtttcttc  71820
```

```
ttgaggagat ttttgtaatt aaatcttcct agaaaatcat caatttttca agattttcaa  71880
atatatgaca taaattcaat atcatatgct cgtaatttaa aagtacatcc tccatgttta  71940
tagttataat tgtttctaat cttatttgtg acatctcctc ttttttcctt gattgatgaa  72000
aaatttctat ttttaataaa ataggttttt tcacctcagt gtcatacaat atacccatgt  72060
aataaatttg cacatataac ccctgaatct aaagtaaaag ttaaaattat aaaaaatagt  72120
gtacgtaaaa ataaaaaaaa acaggctttt gcagagaact aggttttttt taattgagtt  72180
cctttatttt ctgcatcata aatttctgct tttacttatt tattaattcc ttcagctttt  72240
aaatttgttg ttgctgtgtt ctaattcctt gaatggaatg tgtatttagt tctttatttt  72300
caggatttta tgtgttctaa taaataaata aataatcata cattctcctt tcatcacctc  72360
ttactagttt aattatatgg tgcttttctt gctatatatt tctgaataat tgtacgtttc  72420
agcttagatt tttctcttta acccaggagt tatttagaag agatttataa aatttttcaa  72480
ctgcgtagat tttctgatgc tccttttgtt gttaattttt aagtttctta tattgggttc  72540
acagaatgtt ctgtatattt tctgcctttt ggaatttctg gagaatatct ttgtgtccta  72600
atacacgttc agtttttgtg aatatgccaa tgggtgtttg cattagtccg ttttcacact  72660
gctgataaag acatacccaa gactgggaac aaaaagaaat ttaattgaac ttatagttcc  72720
acatggctgg ggaggcgtca gaatcatggt gggaggtgaa aggcacttct taacatggcg  72780
gtggcaagag aaaaatgagg aggaagcaaa agcagaaacc cctgataaac ccatcagatc  72840
tcataagact tattcactat cacgagaata gcacaggata taatataata tagtagcttt  72900
tccaggcaca tggtacaagc tgccagtgga tctactattc tggggtctgg aggatggtgg  72960
ccctcttctc acaggtccac taggcagtac cccagtaggg actctttgtg gggggttctga  73020
ccccacaatt cccttctgca ctgccctagc agaggttctt catgagggcc ccacccctgc  73080
agcaaagttc tgcctgggca tccaggtgtt tccctacagc ttctgaaatc taggtggagg  73140
ttcccaaacc tcagttcttg acttctgtgc acctgcaggc tcaacacaca agtggaagtt  73200
gccaaagctt ggggctccca ccctctgaag ccacagccca agctgtacgt tggctccttt  73260
cagccacgac tgacgtggct aggacacagt gcaccaagtc cttaggctgc atacagtacg  73320
aggaccctgg gcgtggccca tgaaaccact ttttcctcct gggcctctgg gcctctgatg  73380
ggaggggctg ctgtgaaggt ctctgacatg gcctggagac attttcccat ggtcttgggg  73440
attaatgtta gattccttgt tacttatgca gatttctgca gccggcttga atttctcctc  73500
agaaaatggg attttctttt ctactgcatc atcaggctgc agattttctg aacttttatg  73560
ctctgcttcc cttttaaaac agaatggctt taacagcacc caagtcacct tttaaatgct  73620
ttgctactta gaaatttctt ctgccagata ctctaaatca tctttctcaa gttcaaagtt  73680
ccacagatct ctggggcagg ggcaaaattc tgccagtctc tttgctaaaa cataacaaga  73740
gtcacctttg ctccagttcc caatgagttc ctcatctcca tctgagacca cctgaccatg  73800
gaccttactg ttcatatcac tatcagcatt tttgtcaaag ccattcaaca aatctctagg  73860
aggttccaaa ctttcccaca ttttcctgtc ttcttctgag ccctccaaac tgttccagcc  73920
tctgcctgtt acccagttcc aaagttgctt ccacattttg ggtatctttt tcagcaatgc  73980
ccactctatg ggcaccaatt tactgtatta gtccattttc atgctgctga tgaagacatt  74040
cccgagactg ggaagaaaaa gagatttaat tggacttaca gttccacgtg gctgggaagg  74100
cctcagaatc atggtgggag gcgaaagcca cttcttatat ggtggtggca agagaaaaat  74160
gaggaggaag caaaagcaga aacccgtgat aaacctgtca gatctcatga gacttactct  74220
```

```
ctatcacaaa aatagcacag gaaagactgg cacccatgat tcaattacct ccccctgagt  74280
ccctcccaca acatgtggga attctgggag attcaattct agttgagatt tgggtgggga  74340
cacagccaaa ccatatcagt gtttgaagag tatttttatt ctatgctcat tgagtaaaaa  74400
aaatctgtat cagattaggg attgcaactg gtagcccata agctgccttt ggcctgcaga  74460
catgttttgt ttgactcaca caagtgtatt tttgaaaact tgagtaaaca tttacaaatc  74520
acagtatttt atgtaaaaat atggatttgg ggctttctat gaaagcttag aagctctggc  74580
tgtgctgggc cctcattcct taatggcaac agtcggctac gattgctcct aactcaaagg  74640
gcagtctacc cgtccccggg tggccttcac agacctggct gcttcagcca tttaccctgc  74700
ctgcctgata cctttaggca tcagcctcta tcacctgtgt gttctatcaa gttcattcag  74760
aagttctgga gtctttctta ctttttgtct acctgatctg tttctgagaa ggaatgctgg  74820
tttccatgat gattatggat gtgtcagttt ctttccgttt tcgctgtaca cattttatag  74880
ctatttacaa ggtacattac aaggtataat gaatcttcat caatataaaa tcctctctat  74940
ctcatttttg ccctttaatt gtactttggc tgatataaca cctgtacttt gattgataaa  75000
agtagcacac ttgcgaattt attttatcat ccttcttctc atatattctt tatttctaat  75060
gttggtttta taagcagcat gtatctggat ttatatttta acacaattga agagtctctt  75120
taaagaagga ctttgttata ttcatacatg tgctgatttc agatatcttt ggatttattt  75180
ctattgtatt tgtttttatc tattcatcca tccatccatc catccatctg tccgtccatc  75240
tgtctaccaa tctgtcttta cctgcctttt gctggttaga tgtagtttct tctcttttct  75300
ttcattctaa tgggttgaaa tttttacatt ctaaatctgt ttttctgtta ctctttaaac  75360
acagttattg ggacttatgt ttctctacag tgtttagcgc taatcagtac ttaactcttt  75420
cacctgagca acataagaaa cttaccatag ctccactcct ctgccatctt ctgtctgtcg  75480
tcacctcctt gaattgggat aattcaaaaa tttaactcca tattattttt aacaagttta  75540
catcatgcat caacaattgt gtgagcttaa gtataaagtc taattaattt ctttggtcac  75600
cattgtttct tttttcttac atctttgtat gtgatttttt tattttacta gatttctcca  75660
tctattaaat tattcattct cttaaaagat attttgagtg cttgctatag gtatgaatgg  75720
ttatatagat agtaaatttt ctgagtcctt gaagtctaaa aatgtcatta ttttctccct  75780
acaaatttgg ctaggttttg actttaagtt caagataatt ttcactcata atttaaaagg  75840
tattacccca tggtctttgg tattcagtgt tgctgacaag gggcgtctct ttgtctcagg  75900
tgaatttttt tgctctgaag tctactttat ctgatattaa tatagctact tctactttcc  75960
tttgattaat ggttgtacag tatacgtttt tccatccttt tactttcaac ttgcctatat  76020
tgttatattt gaattgagtc tcctgtagat aacatatatt tgggccattt tttaaaattt  76080
atttttcttt tataaaaatt tttattaatt tgaagagtac aatacagtag aaattgcctc  76140
ttttttcttt tattgataaa tgacatttca catatttaag aggtacctgt gaatgttttc  76200
tacatgcatg gaatgcagaa tgatcaagtc aaggcatttg gggtatccgt catcttgggt  76260
gtttatcatg tctatgtgtt ggtaacattt caagtcctct cttctacact gaaatattta  76320
acatattgtt gctaactgta gccccccggt ctgctgtcaa acgtgggcca tgtttttaga  76380
ttcacttgcc aatctctttt agttactata tttagatggt taatatttaa tgtaattatt  76440
gatacattag gggttaagtc tgccatttta acttctctat tattttcctc tgtatttagt  76500
ttctctgttt ttttttcct gccttcctgt gggttacttg aacacttttt aaaatctcac  76560
```

-continued

```
ttggtttata atgtttttga gtatgtcttc ttgtatagct tttttagtgg ctacccttgg  76620
tattacatta tgcacatgta acttctcaca atcaatttta tgggtgttgt cactttacca  76680
gcgtgaggta cagaaacctt accttccttt atatcccatt attctctccc atttatattt  76740
gtaatataca tacatattaa acatacattc atttagaacc acatcagaca gtgttgtaat  76800
ttttgcttca accatcaaat gtaatttaga aaacttgaaa gtaaacttgg tgaatctgta  76860
ggtttatatc tcttgccaaa tttggagagc gtttagccat tatttcttcg agaacttttc  76920
cagcccccac tacttttttt cctcctcctc ctcctcctcc tcctcctcct cctcctcact  76980
cctcctccat tattagagac agggtctcgc tgtgttgctc aggctggagt gcagtggggc  77040
agtcatagct cactgtaacc tcgaactcct gggcacaagc aatcctccgg ccttggcctc  77100
ccaaagggct gggattacag gtgtgagcca ccactcctgg ccctttttcc tctcctcctg  77160
tccactctag tgacatgaag tttaggtctt tgttatagtc tcacaagtcc ctaatgctct  77220
gttcatattt ttaaattttt ttctttatgt tgttcagatt gggtaatttt atatatatat  77280
atatatatat aattttccag ttcactcttt cttctgtcct gtgggttcta ttactgagcc  77340
catcactgag ctttttgatt attgtatttc cagttctaat aattctactt ggttcctctt  77400
tatatcgtgt atttctttgc tgagactttc agtttcttta ttgagacttt ctatttttc  77460
atttgtttta ggcatatttg taattgctca cctaggtgtt tttttcatgg cctctttaaa  77520
atctttatta atatacaact agtatatcct taaaaattaa aaataatttt aaaaggtaaa  77580
cctaaaaaga ggaagaaaat gaataaaatg tctgtcagat ggttccagca tccgtttcct  77640
ccatgttggc atcggtgatt gtctgtcttt atgcatttga gatcttccta ttcgttcttg  77700
gaatgacatg tgatattcct ttgaaacctg tacatttttg cattatgtta tgaggctata  77760
cctgacttca gccttctgtt tcagctggct tctctggccc tgttgctgca gaggacaagg  77820
ggtaccattt cattattgtc aggggtaggt tgtccagggc ccccattcag cctccgctga  77880
tacccaagcg tgggaagtct ccttatcagt gctgagaagg ggcagtggtt cccactccct  77940
gtgtgcctcc catgacccca cagtgcaggt cccctcatta ctgtgagcag cagtgagcct  78000
cctgactctc caccaggcat cctgacacaa ctccagggga tggaggggac acgttgttac  78060
tgctgggtgt ggttggaaga ccaggctcat ggcatggtat ctgctggcac catgcaagtg  78120
ggcccctttt gaggttgctg gaggtaaaag cgctgcttcc tacctgctgt ttcctgacat  78180
gccccagcag tgaggtcggg cacctcattt cgtcctcgca tgggtggagg tctaggctcg  78240
ccactcaggc tgtgctgcca taggtcgggg tggtaccacg gttccttgct gtggtatttg  78300
gcctacttat tgtgtatggt tttttccatt tgttctattg gccctgtctc gtcgggtccc  78360
tctgttcttg ttcatgttgc tttttaattg ggtgcccctc tttcttggga tgggttttcc  78420
tcaaacatgg gctgcttctt ggtcgtccac ccctgcatgt gctcacagat ccccatgtgg  78480
ctgtgggtgg ttgtctggtc tgacggcagg ggtctttctg tgatgtggag tggagggagc  78540
tgttgcttga tagcatttct tctgagaagg gtgcgaggcg gactccccgc tcccagggca  78600
tcgtcctggt gctctggcct taggaccctg tctcactgca ccagcctcaa gatgactctg  78660
ctgctgtccc cactcagcct ggaggctgag acctgccacc ctagctcctt actccgaggc  78720
ctgtttgggg ctcctcctgt ccttgcacgc ccagcctggc accttcctca gctctggaat  78780
tgttccccac tcagaagtcc tcgcgccagg accccgcctc ctgctgctac ctgatgccct  78840
ctgcttcccg tctttcctca gtgcctcaag acagctcgtc tgtgctgatc ttgtttccca  78900
aggctggttc agatttgttc gttctaagtt ttattcctag ggatccaggc cctggggaga  78960
```

-continued

```
ggtaggctgc gtgctcagtc ttcctcctgg gttgggtctc ttgagtcttt tcactgtggt  79020
gcagatggtg acacctcttg ccgattgctg ttggttgcca agcacttgta gtcatctttg  79080
catccagttc ttagtgtgcc tctgtgcgct ggacatgatc atggccgttt cccaccaggg  79140
gagactaaca gagagatgaa ttgccacatc tgggttcaca cagctgccaa gaggcagcgc  79200
agaggcttga gctcaggcct gttgccctga agcctggatt ccacctttgc aatcatagcc  79260
ttctgatgct aggacatcgc ggtgaccaga tgagaacagc tgccaccaag cccagtggcc  79320
agaaacagaa gcagaagggg aagccttcgc agtgtataac tgtatacttc ttgactgaat  79380
tctgattcct tccaagcata ttttggcctc gcctcttcct cctggcctaa aaaggtatga  79440
taatgggaac agcacaggag ggagcgagag agggcagcag gcatttccta gcccctcttc  79500
ttattcatcc tttctttgct ctcttgctct gttcaccttt ttgtcttttt aattttgacc  79560
tggcacatag ttctccttct ctctctctct aatgctcctt ccctcccagc ccttctgctt  79620
cagggtggca ttggtggtgg ggggctccag acttggctgc ctccactgcc atcagctcac  79680
ctccaaggtg agtgcaggct gagcttcatg gcaagccctt cctgctgggg cctgcagaat  79740
tctaaaggcc ctggccaagc acagtggctc acacaaaatc cctgcagttt gggaggccaa  79800
ggcaggagga tcacttgagg ccaggagttt gaaaccagcc tcaacaacat agtgagaccc  79860
tgtgtctaca aacaatttaa aaattagcca ggcatggtgg cttatgcctg taatcccagc  79920
cactcaggag gctgaggcag gaagatctct taagcctaga tgtttgaagc tgcagtgagc  79980
aatgattgtg gcactgcact ccagcctggg caacagagca agactcaaac tcaaaaaaac  80040
aaacaaacaa aaaagtgtga aggcccctcc cagaatgcag gctgaggatg tgatcccatc  80100
cactgcacca ggtcctcctg gcttcgtgcc ccatgcggca tcctttgaga aaagcttgct  80160
ggggagccag gtgtgctggc ttggccggag tggaacctgc tctctcaggg aggcttgcaa  80220
tatgcagggg aggtgagtgg agccctcacc cctttaactt taccaggctt ctaccccttta  80280
gcaagttcct cacgtgtgct gatacttaac cagattcaga cactttccta aggcaggagg  80340
ggtgtcatga gggacactgc attatggtac actttccctg cattttttttt tttttttttga  80400
gacggagtct tactctgtcg cccaggctgg agtgcagtgg cacgatctcg gctcactgca  80460
agctccgcct cccgggttca cgccattctc ctgcctcagc ctcccgagta gctgggacta  80520
caggcgcccg ccaccgcgcc cggctaattt tctgcctttt tagtagagac ggggtttcac  80580
tgtgttagcc aggatggtct cgatctcctg acctcgtgat ccgcccgcct cggccgccca  80640
aagtgctggg attacaggcg tgagccactg cgcctggcct tgtattttta atagagacag  80700
ggtttcacca tgttggccag gatggtctcg atctcctgac ctcgtgatcc gcccgcctcg  80760
gccgcccaaa gtgctgggat tacaggcatg agcccccgcg ctcagcctcc ctgcttttca  80820
gaagcatcgc cagtccacag ggcaggatcc ctgaggctgg tctggagtag gctgcatttg  80880
gggcctgcag caagggcagc tggagaccgc agggagccct cccacctgac aaacagaaaa  80940
gctcccctgc tccggccccc ggatataggt gcatcttttc agaccatgtt tgccctgttt  81000
ctgggaagga aaagtaaacg gcagcgacca gattcctgtt ggtgtttttg ctccatattt  81060
tgattgggga actgaatcat gtttttcctt tcataaacac gaaaatgtta agtacataac  81120
agctaaatta atccatgccc ataaattggt taattatgtt aattctgagt cacagaattc  81180
agtctcgtta gtgtttccat taagcagttt aggcctgtga gcattttaag agaacagttt  81240
aagctgtaga ttaatcttca aaggttccca gcgcattttc aactgcaaga ggattttaaa  81300
```

-continued

```
tgcactgggg ggcttggggg gatttggtga atgttaggag ctgctgctgt cagggagcgg  81360
gtgttcccca cttcctcgtc cctcacctcc cccaacacat ccaaggcccc tgcctgctag  81420
atctgagcat cgccaggcta agcaggagcc ataggaagga ggagatgggc aagaactggc  81480
atagcccctt ctgccctgtg tctccctggt ggccatgccc tcctcaggcc gccctgctgc  81540
agacacccgc agagaatggg tgaggctagc tctcgaatgc tgtgggctgc atagccctgg  81600
gttcctgaga gggctgctga ggggctttct tcctgggtgt acataagaaa gaagcagaga  81660
gacaggaaga gagcacgctg agtcttagaa acaagctcct gggtggcctt tgttcatggc  81720
ggcatgaacg tctccttttc gccgtccgtg tccccttcag aggtccgttc aggatatggg  81780
tttgctttct tggcacgtgc gcctcctcta gggttccttg ccgtacttgc gtgtggtgca  81840
gatgtacggg tgctccatct ggctcagaag cctgctgtcc tgtcctgcat cccaagctgc  81900
cggctctcac tggcttcctg tgtgtgcctg ggccatgcac ttctgttctc cagccctcat  81960
tccctagcgg ggagaccgtg aaagggtcag cctcgatgtc aaacctctag accatggcta  82020
aggcttttcc aggttttgta ttgttctttg aagaatcaac aggacccgat tatcaaagag  82080
agacctgttt aaatatgtac aatcattttc ggtattattt aggtttggca aggccagcag  82140
atgaggagac cactgccatg cattgaaaag gtggtttgtt ccagttccca agaggatgcg  82200
tcccagtacc gtatgtgggg ccacacagag aagcagcggg ttctgtcagg aggcaggaga  82260
gaggggaaga cacgggccag aggccttgtg gtggtttctg tgggaaggag tgggtgaggc  82320
agagaaggca agttcagaat cagctaggct gaataatttc agcagactca ggggaatagg  82380
ggctgtccct agctgcctga cacctggcct tgggtggtta ggttaaggga gtagtgacct  82440
ggtgtgtgag agcccatgat ggaggtggct ggggtgtaga ctctggattg gttggcttgc  82500
atgtgaaaag cacactcctg atgggtagtt tactatcccg agaccctggg tagcgcctga  82560
aggaacagtc tccccagggt cagcaagccc cagatgtcaa agcatcagat actgaaaata  82620
caagaggaag gggagaagat ggatgatacc aaagttatcc cagacgcagt accagggcca  82680
gggcctcaac ttagcttttc attaatcttc tcaactgcct tggcagataa atattgtaga  82740
aaacatgatt tagagaggct gagactatgg cccaaggtca tgcagagccg acattccgct  82800
ccaggactct ctgaccccag ctgtcttccc cctaccatga gctgctctgt atcttgccag  82860
gggccatacc cttgccacac cacactgcca gcctcccacg ctggtcacgg cccttctctt  82920
ggaggtcgct ggctgagaga gctgcgcacc tgtgtccgtg acacagctgt ggagatggga  82980
cgccagacac atggaccaca gactggggaa ccagtctcag ttatcacggg acctgacctg  83040
ggacagacct catctcctgg atccagggct gcatgcagga catgcccata aggagcgtcg  83100
ctggctacag ctgtgtttcc actgtagaag gaggtggagt ggctccatca gggcatcagg  83160
aacagaacag gaagcaggaa gagatttggc ttggtgatcc cccgcgcgtc cccacacact  83220
tcatgtcacg atggcgaacg taggtctgcc ttgacaactc ggcagaccac agctccctgg  83280
agctcctaga acaaggctgt cctgtggggg catagttagc aatttgaaag ccgtgtctat  83340
tgtcttaggt gataatgagg gttgacagaa accttttagg attgtagcat ttctaagtaa  83400
ctgttgaaac cttacttggc ccggaatggc tgctcataga acagaatgtg ctatagtttt  83460
actgaaaaaa acaaaacaaa aacaaaacat aattctctgt ggacttacta aaataaaccc  83520
agggctaatg agcaaaatgt gttggggagg cctatttgtc acactcagga agcgacagtc  83580
taattttatt tgctcctgtt cattgcttct gcattgccat tcattcgctg aaggcaaaat  83640
acattacttc tcaataaaca aaagtgggcc cagcgtgtcc cgctccctgc cttcctccag  83700
```

```
ccgttatccc cccgggcagg agggctgact tgtattgatg tgcatgtgtg cgtgtgtgtg  83760
tgtgggtgtg tgggcttgtg ggtgtgttct tcccattgct cttaatgttg agcttcctag  83820
aaagttttca ggggaaatgc tgtgtctcgt gctgactggg gccggctgca tgttgatagg  83880
ttcaccttgc cttatacaaa cctgctattt ggaaagtcga gatataaatt agaagcaggc  83940
ggccgggtac ggtggttcat acctgtaatc ccagcacttt gggaggccga ggtgggcaga  84000
tcacttgagg tcaggggttt gagaccagcc tggccagcat ggcgaagccc catctctact  84060
aaaaatataa aaattagcca ggcgtggtgg tgtgtgcctg taatcccagc tactccagtg  84120
gctgaggcag gagaatcgct cgaacctggg aggcgaggtt gcagtgagct gagatcacgc  84180
cactgcactc cagcctgggc gacagaggga gactctgtct gaaaaaaaaa attagaagca  84240
ggggaaatgg aggaaagaca ggtcactacg gaaaaaaagt ggctttgttt ttttttttag  84300
cttcactaag tgagttgtaa aatcattcat ttcatcaagt tctcccaggg catttaaaat  84360
attattgggt ttaggagatt ttataggaat gcacgtatta tttaaagcaa ggcaaactgg  84420
tgtgattcct tcctggatgg agcttctgtg ggcagctgca attgtcagtg gggggattgg  84480
ttcccatagc accccgagtt cttccctcaa acacaaaggc accaggttct ccaaagcaac  84540
catcttcctt ccactcaaca ctcctcccgc ctcacaccca cagactcgtc cttagagtgg  84600
actgggcagg cgggttcatt gtgccacgct gtgctctgaa cccagcatgc ccaaaagcag  84660
tccgttagca agctgaccat ggggagttca ttgccatcaa tgccatcaaa acaatttgcc  84720
caaatcaaat ttatacctga cattttatag taaatgggcc tttcttttct cattagagaa  84780
atcattactg tttttcttct ccttggcatt tccagagagc cattcacatt taaagctcat  84840
gttggaacag caggcttcta ctgaaaatat ttaccttttc tttgttggca acttgtcagt  84900
gttggggaaa atagatgctt cattaagatc taagcgcgtg atgcttgctt tcccacacat  84960
cagtcagtct ttttccaaga tgaaaagcat ggtgagaggt gttgggaaat cattctggtc  85020
atatgttttt atgtattttt ggatgtcttc tggcatcccg ttcttcttgt tcaaaaatag  85080
gcatttcaac acctataact tgtagagaga atcctagaac aggatcagct tcaccactta  85140
gagcatcaga attggtcttg acccccgggt ggccagtgag gtctcctgcc ctggagatcc  85200
atggctgaaa gtaagggcaa agagaaccct gctgccattt atccagcagt tccggggcca  85260
gggcctcaac ttagcttttc gttaatcttc ttaactgccc cggtagataa aaattgtaag  85320
aaacatgatt tagagaggtt gagaccatgg cccaaggtca tgtggaagcg agattacacc  85380
ccaggactct ctgaccccac tctcttcccc taccgtgagc tgctctgtat cttgccggcg  85440
gccacgatct tgccagcctc ttgcactggg cctggccctg acccttctct tggaggttcc  85500
tggctgagag agctggacac ttgggcccag tgtccctgac acagccatgg agatgggatg  85560
gcaggcacat ggaccacaga tttgggaaag accccacttc atgtccaccc gacccctcct  85620
ctccacccag aaaggacaaa atacagtgag ctgatgccac agcccatgtg agctgggcct  85680
agaggtggct ctgccctgcc tataaaaggg ggaaaggaac ttacaataga tgccagcaaa  85740
cccagaaacc cagagaaggt tggcccctgt tacgactcct ttgatcttca cagggaggtg  85800
agctcttgct ctattaaaat taagaacctc tgtttgtcta gagctaccat aaacacagtg  85860
agaagaccag gcatacactg ggagaagatt tttataacct gcattaccaa caaaggatta  85920
attctcagta caagcaaaat taaacaatgt atcacttaag catatataca attgtattaa  85980
actagtagta tttaaaaagc aatggcctgc gaggtgggcg gatcacctga agtcaggagt  86040
```

tcaagaccag cctggccaac gtggtgaaac cccgtttcta ctaaaaagca caaaaattag 86100
ccgtgtgtgg tggcgggcgc ctgtaatccc agctacttgg ttggctgagg caggagaatc 86160
acttgaaccc gggaggcgga ggttgcagtg agccgaaatg gcgccactgt cctccaacct 86220
gggcaacaga gcgagacgcc atctcaaaat aaataaataa ataaataaat aaaggcaatg 86280
gcatgaataa tccaaaaatt ctgatcattt tcctctgaga agctgggggt gacagggagg 86340
acacagaagt agaggccccc agtgggtcac gttcttgttc ttgcattggg ctgcagggtt 86400
catgggtatc cgttttttta ttaggcttta taactaacgt gtatgtgaca tacaatcttt 86460
tgtgcttatc aagtcatgtg tttttagaaa acaaaaagaa aaaccaatca gttattgtta 86520
ctacctccat ttttttttct ctctcttttt ttttaattat tattatactt taagttttag 86580
ggtacatgtg cacaatgtgc aggttagtta catatgtgta catgtgccat gctggtgtgc 86640
tgcacccatt aactggtcat ttagcattag gtatatctcc taatgctatc cctccccccct 86700
ccccccaccc cacaacagtc cccagagtgt gatgttcccc ttcctgtgtc catgtgttct 86760
cattgttcaa ttcccaccta tgagtgagaa catgcggtgt ttggtttttt gtccttgcga 86820
tagtttactg agaatgatga tttccagttt catccatgtc cctacaaagg acatgaactc 86880
atcatttttt atggctgcat agtattccat ggcgtatatg tgccacactt tcttaatcca 86940
gtctatcatt gttggacatt tgggttggtt ccaagtcttt gctattgtga atagtgccac 87000
aataaacata tgtgtgcgtg tgtctttata gcagcatgat ttatagtcct ttgggtatat 87060
acccagtaat gggatggctg ggtcaaatgg tatttctagt tctagatccc tgaggaatcg 87120
ccacactgtc ttccacaatg gttgaactag tttacagtcc caccaacagt gtaaaagtgt 87180
tcctatttct ccacatcctc tccagcacct gttgtttcct gactttttaa tgattgccat 87240
tctaactggt gtgagatgat atctcattgt ggttttgttt tggatttctc tgatgaccag 87300
tgatgatgag catttttttca tgtgtctttt ggctgcataa atgtcttctt ttgagaagtg 87360
tctgttcata tcctttgccc actttttgat ggggttgttt gtttctttct tgtaaatttg 87420
tttgagttca ttgtagattc tggatactag ccctttgtca gatgagtagg ttgcgaaaat 87480
tttctcccgt tttgtaggtt gcctgttcac tctgatggta gtttcttttg ctgtgcagaa 87540
gctctttagt ttaattagat cccatttgtc aattttgtct tttggtgcca ttgcttttgg 87600
tgttttagac atgaagtcct tgcccatgcc tatgtcctga atggtaatgc ctaggttttc 87660
ttctagggtt tttctggttt taggtctaac gtttaagtct ttaatccatc ttgaattaac 87720
ttttgtataa ggtctaagga agggatccag tttcagcttt ctacatatgg ctagccagtt 87780
ttcccagcac catttattaa atagggaatc ctttccccat tgcttgtttt tctcaggttt 87840
gtcaaagatc agatagttgt agatatgtgg cattatttct gagggctctg ttctgttcca 87900
ttgatctata tctctgtttt ggtaccagta ccatgctgtt ttggttactg tagccttgtc 87960
gtatagtttg aagtcaggta gcgtgatgcc tccagctttg ttcttttggc ttaggattga 88020
cttggcaatg tgggctcttt tttggttcca tatgaacttt aaagtagttt tttccaattc 88080
tgtgaagaaa gtcattggta gcttgatggg gatggcattg aatctataaa ttaccttggg 88140
cagtatggcc attttcacaa tattgatact acctccattt ttacagatgg gaaaactgag 88200
gctcagtggg gtcaaactag cagcaaacac acacgttgaa tgcttactgt gtgccagacc 88260
ctttacacgg atcatccgat ttcatttgtt tgacatccct ctacatatga taagtgtcat 88320
cattgcagtg tgcagaagac tgaggctcag cgagacggga gaacttcaga gtcactacct 88380
ggtcacagtt gatggtgaag gcaaggtctt cacctgtggc atgccccacg tccctcctgc 88440
tggctccgag gctcactgtg agtgacagct ccactctgtg gacctcccct tgggagcagg 88500
cgtcgaggca tctaagtcca cttgccttgt gccatctcag tgcctggaca ctggtggcta 88560
ccctgggccg tcctgcagcc agctcgctga ggtaggaaag agaggaaggg aaacaggtgg 88620
agtgagaaga gaagatagat aacactgaag ttacatttat tcctactgct catagtaggc 88680
tttcaagcta tgaagagatg gctcttcccg tgacttcagc cccatcctcc atcgctgccc 88740
acgcccacgt ggctgacact gccgaatgtc tctagcactg ttgttgaact tctgatgtct 88800
cctatgcctc aaccttgcta ttgccttggt gtaaatttct ctgacattga ttttgaatac 88860
aattccaggc ttttggagca gaagtttcca gttaagcttg gtgtcccacc taagtgttaa 88920
ggtcaacatg ccgagcccta gagtggtcct ccctctccca ccaccaacta tcctacctgg 88980
cctcccaaga actgcctttg gtgactcttg tattctctgt cttgcttcat gcctgggaaa 89040
tttcagggca tatattaagg ggaaaacctt agggaaacct gaaccttcaa aactgggtag 89100
aatgaatgga tggaatggaa gaatttactg cagcgaaatc atcttcaaat tccttttagg 89160
ttggaagctt cttaccctgg caagtgaaga agtacatttg gttatatgtt tataatccat 89220
gtgctactgg gtgaaagatg ataggacaag aacatttgaa atgtatgtgt tagggatctc 89280
tgcccagcag tttccatcaa aagagcacac ccatgattat cgtacaaatg gatgggacag 89340
caggattcta ctcacgtaaa atgtttgtcc ctgagcacct agggagggtg tcacctccag 89400
ggtctccttc ctgttgctct tctgcatgag tcctgcacca cctcttttaa cctcagggaa 89460
aacttcacta ttttgttttt taaagtcagt catatttaaa gttgctgctt ttgagtatgc 89520
actacgtgtt gatgtagatt ctggaatgta gaacaaacag gcgcagacta gtatgggtaa 89580
ggtggggaac ccctacttca gaaggtgaac cccagaagga agctgcctgg gccaggggtg 89640
tgtgcatgat ggcagggagc tgcagccact aagccttgga agagtcttta atggcacagg 89700
gaaatgccct gtataaagct cagtggggga aaaaaaggat ttagaaagaa agtatatgcc 89760
agaggcaaag aaaaagacta gaagaaaata accagccagg tgcagtggtg tgcacctgtg 89820
atcctagcta ctcgggaggc tgaggtggga tgattgcttg agcccaggtg tttgaggctg 89880
cagtgagcta tgatctgtgt cactgcattc cagcctgggt gacagagtga gaccccatct 89940
gtaaagcaaa aaaagaaaag aaaatagcca aaatattatt ggttatttct ctttttccca 90000
aagtttgggc aagagcatat actattctta caatcagaag aagtcctctt ttccattacg 90060
tcttaaatag ctctaagatt tagaattcgt cttgatgaag gcatggtcat cgcacacaca 90120
gagctgggcc ccgtgggtga ggggctcccg ggggcctctg agtggggagc tgtgggtgtc 90180
aagtggccat gaagagagtt gacccagggt cgggtggcaa gattctctga gccccagaga 90240
agtcgacttt ctgtatctac tagaatccag gaagagtgtg tccatggccg tcattacccc 90300
ctgcttcccc gtttcatgcc aggtttttct cagatgcctt ctctggggga ggcactgttg 90360
ctggggcaac tttctggctg cagagggcac ccagtaataa aggcaaatgc caagtatgag 90420
gcaagaaggg acgcccctgg ctgggatggc aggcattggg agaggcttat gggagcccct 90480
cacccctctc tttttggggt gctctcgagg aagctggact ctccacctct aaagacccct 90540
ccagggaaca tagaacccaa acccaaatgg agatgagctg gccagcgaag tccaagaccc 90600
cagtcccctc cattgcaacc tggggtgcgg gcttctgtct tccaggttga aagctcatca 90660
tttggttcat cataagttat acgtcggagt ggaattataa aggagagaga aacagatgtg 90720
aactctcaac agctgggaga ggtggaaagc ctctggagtt ccattataga aatgtgcctt 90780
ttggccagga gtggtggctc acgcctgtaa gcccagcact ttgggaggct gaggcaggtg 90840
gatcacttga ggtcaggagt tcgagaccag cctggccaac atggccaaac cctgtctcta 90900
ttaaaaataa aagttagcca ggcatggtgg tatgtgcctg tagtcccagc tactcgggag 90960
gctgaggcag gagaatcact tgaacccggg aggtggagct tgcagtgagc cgagattgca 91020
ccactgccct ccagcctggg tgacagagtg agactctgtc tcaaaataat aataataaat 91080
aataataata ataataatag gtcttgtttt ttaaaataaa aaacagaaat atgcattttt 91140
agataccagc aggacatcat agcactgagg gaagctgaac cctctctttg ggacgtagct 91200
tgctttcttt tgttgccctg gcctgagttc tttcacatca gccagcatgg agaagaggag 91260
ccagttttgc agaatgactg ggaacagccc ctgctgggga gggactctgt gatgcggtgt 91320
cctcatccga gcctcctggg cccgggttcc cgtcgctgtg tgcccggagc ctgggcgccg 91380
acaccgagcc tcctctgtgc tttcaggcat ccgcatgctg gacggcgatg tcacagatgt 91440
ggtcgaggca aagtcgctgg gcatcagacc caactacatc gacatttaca gtgccagctg 91500
ggggccggac gacgacggca agacggtgga cgggcccggc cgactggcta agcaggcttt 91560
cgagtatggc attaaaaagg tgtgagtaac cagggctaca ggggagcgct ctgggacaag 91620
ggtgacagta aacattttaa caagtatcag agtgacactg gccacagccc tgaaacaaga 91680
cagggaagac tctgctgtga caggtgccag ggccagtgtg gaggagtcac tcggggagtc 91740
tgagaagtgg ctcttgaccg gcgagagcag aagtgttttt gcctcgttcc agaacagctg 91800
ttccagtgac agccaggtgg ccactgctag cacgaccctc tctgccttgg agtttgccca 91860
tccctggctg aagggggtac acaggtgggt gacgggggtc taaggcagct cacctggcct 91920
gttacttgga ctctgcaggg gcctcggccc acctgccctt agaaacaccc agctgtggaa 91980
ctctgtgcat tcatcgcggg gtatgtgctc acccaggccc cgctgcagca ggaagcagtg 92040
gtcggggtgt cccccaccag cgcacagccc agcccacttt gaacttctcc aggggaacct 92100
cacaaggggc taagcagggc aaagatgctt ctctgccgat gggccaaggg gaggctggca 92160
ggctcctgcg aggccacccg ccagccactc tgtggtcttt ggttccggat ccttgtgtgt 92220
caggaaggct gaggaagggg gaggaggtgg ctgcagatga gccagttctt acaaacaggg 92280
tggcaaggca gatttctggg tgaggacagc ttcttggagc aggcagacag agctgtggtc 92340
agcgtccagg aggccctggg tggccgaaca ggtcccagcc caacgtacaa tgtgtggtca 92400
gtgactgctg tagggagtgg ggaccagggg agttccagca ggaagtccag gcttctctga 92460
ctcctcctgt gggggatggg agaatgggag ggggtggcag gagtcaagcc cattaaattt 92520
atatcgttta aaatattttt acagttctca tcgtattata acccatgcat agtgattgca 92580
gtgtggctca taaacagcta gtaagtcagt cggatagtag gaagagatta tactgcaaac 92640
agcctctctc tgtctctgtc tgcccacccc cgagtcctgc cccacggagg aggaatctgt 92700
tttcaaacca tgttcatgat ttcctttctc taagtaatat catttgatgg ctttcctggg 92760
tgcgttgagt ttggtcacca tctgttaatt tcctcttatc agaatgagcg tttttctctc 92820
aggagacccc tagccctgct gccctgccga aaccctggag tttcctccac ttcttacctt 92880
tcccgggcgt caggcctaca ctgcatcctc tgcctcctgc cagctgcacc tgcctgcacc 92940
tcctccgaag gacttggtgt cactctgcaa gtgtgaggcg gaagcttcct cctctactgc 93000
ccccaccccc caaccactca ggtcttgaat gcctgagaaa ccaatgacca aatacagggt 93060
atctacccac ctgtccctcc gagtttagta ctcacccaga cactaaatgt gagaaggaaa 93120
attaaggaag aggggcggtg tagacacaca cacgcacgca cacagcatgg ggtcttgcgg 93180

```
gcatccttgg gacactggac agcttccttt atctccattc cccaagaaa acaccgaggc  93240
agcttcaatg aggctgctga gcacctaagc caggcccaag gctgggctga gtgagtgctg  93300
gcacactcgg gtatgaccaa gtcagctgct gcccaccaag aactgccgaa tacataaatc  93360
acccttccat tacttagctc ccagctccaa cccactagat cgcttggatc tcagtcttga  93420
tgacaagcga gacatcctaa aaattaagct gaatttaagc ttcggagagg gtgggtaagc  93480
tggagggcgg gtttcctgca tagaacatat tgctttggat ggtgttcctg ctgagcgtct  93540
gtcatttcta cgggatgatt tccaaagatg gagctcctag gatgaggcac cctccgtcca  93600
ggaggggtcc tggttgtttg gcagtgatcg ttcgggctct ctggttcact gagcctatgg  93660
gaggcttggg gaggttggag ctgcagagag ggatctttgc attcggaatt ctgagcagtg  93720
ttggtttcat ccagctgtca ggggagtggg gaagttgcag aggggaccac gtggtttccc  93780
ctcattcttg tcacagtttt gtgaaatact gaggtcattt gatttttttt cgtcatttgg  93840
aagtaaaata tgtcatacag agaaccttaa atcgcaactg tctcgatctg tcactgaaaa  93900
tcctcctaga aatttgatga tctcaaacca aaccacattc ccccatctgc ttttcctcct  93960
tgtggcccta tttgtcgcct acagtcttct gtaaaatctg actttatctt tggtagatga  94020
tgtggcccgg cggtgagaga ctgtagaagc tgtaacttgg cacaaagatc tgtttaacgt  94080
tggtccttag gaagcctggc tcctctcaca cctagttatt cagaagggac cattagacat  94140
tgctgtggct aaagacactg gccgcgtcca ggtggccggt gtttgctggc cctcagtcgc  94200
ggtgcttctg agctcatgaa atgaactctc cctccccagg gaagacatcg aaatacgatt  94260
tgattgggtt gaagttgtga gtttactgaa aagaagtgca agttcatggc tagggttgaa  94320
atgtccccta cagcttctgt cccatggctt ccatgaagcc actggaagat ctgggaagtg  94380
aaaataaagt cgtcagagac agttaaaaca tctctacact cctcagacct ggctgtttcc  94440
tcgcctcatt tccatgtctc cttcccagaa accgttttaa ggaggggaaa ggttgttggt  94500
accttgatgc ctatgaggat gggttggtct catagtaaat gcatgctaca tgctgtaaat  94560
gcaaaccttg agcatttcag gctcttggta ttcaaagtgg ggtccagagc cagcagcact  94620
ggcgtcccct gggagctcat tagggatgca cactctcagg cccaccctgg actttggggc  94680
acaagtctgc attgtaacag gttcccaggt gactccaggg tgtgcacatt caagtttggg  94740
gagcactgtt tttggccatt ctctgctcct ggagcagtaa ggttgcatgc tccaccttgc  94800
aaaaggacaa cattttataa gtcatttcaa gtggggtggg gagttaggag tggcagtgtc  94860
taggactaat tctcacctgg aataaggaca ggctctgatg ggttaaatac cttttgattt  94920
gcattgtagt tgctttaaac cggcttcagc tgaatctctt cctgcaggta atcacgtgca  94980
cacacacacc accttcctga gctctttgtg cctttctctc agaaggttag cttttctggg  95040
agggaccttt ctgttgagct cttggccacc ccgacaggtt caccttgcag atgcagaaag  95100
cagagtggac gcggcagcct taagcagcgg ggctgcgtga gctccaagaa ctttcctgtg  95160
ggctttcttg ggagcctcaa gttggagctg gagtctcctt ggtttacaaa cccccgtggt  95220
gtgagcgtac agagcaggcg ggtccactca ttgtgctcca aaagtgagtg tgacatgttt  95280
ggtcagcagc aggcttcaat ttggctctac ggggattgca gaattggtgt gtaagttatc  95340
tttaaattgg ccgattgttg agcataagta taaatttcct ctgtttgttt gggaaggacg  95400
gtccttagta aggatgtgat ggccagccag tggctccagt ttcccgtgga ggtggatgct  95460
ggcccttctc tcgggccagc tgtgcaccac cagcccatcc agccatctgg actatatccg  95520
```

```
tcagttcagt cttccactcg ctaatcttta gctggtactt gtggctggaa tgattctcag  95580
tgtggtcaga aatcatccat cctgtgggta tgggatagag cggagctgca ggaatctgcc  95640
ctgactggct gctgtctttc aaagacttgc tttcatgtgt acgttcttaa caatgaacac  95700
cggtgcacag ctgggcatgg cggcacactt ctataggcac agctactctg aaggctaagg  95760
caggaggatc acctgagccc gggagttcca gaccagcctg ggtaacgtag caagacccct  95820
gtctcaaaaa aaaaaaaaca aaaaacaaaa aaacggaaag aaaacctaca cacaaatgag  95880
gccctggcct tggctagtga tataaatcag accaccctga tacttaccca ctgcagagac  95940
cacagggagc tctgacagga cacccacaag ctgctaccag cttcctggac gtaacccttt  96000
ccacctattc tgtcttcacg cagagttcat ggtcctatcc ctctttgcaa atttagctct  96060
ctctgcaaga agggtacctc ttcaagtatg ttttccagaa aaatcattct tttccccacc  96120
agaccagctc tttcaaccca gaaaaattaa agttgtaaat tcttccatca tctgtaatct  96180
cagtgtcatt tgcagcactg ctagctctct ttgatcctag gccattgcga tggaaatgac  96240
aggcatggct ctggaataga gcagcttgtg ttgggaccct tgatttttcct gtgaagaaca  96300
gaggagtctt tctggcccct tcccctcgta tgatcctgtg attctgcaat tttaaggctg  96360
ctgctacagg caaaggcaca ccattaaaat ccaaacagag cccccaaaac catgctctca  96420
gcagcatcca gatggtctga atgcaacctt cttatccctt tgaaggaaca tttgggagat  96480
gggactctag gttcgggggg agacccaccc tacgaggttc tgctgcgggg ctaagccttg  96540
ttcctcttgt ccctccaggg ccggcagggc ctgggctcca ttttcgtctg ggcatctggg  96600
aatggcggga gagaggggga ctactgctcg tgcgatggct acaccaacag catctacacc  96660
atctccgtca gcagcgccac cgagaatggc tacaagccct ggtacctgga agagtgtgcc  96720
tccaccctgg ccaccaccta cagcagtggg gccttttatg agcgaaaaat cgtaagttct  96780
cttggcaagt tggagtgctt acagtgagtg cctcagccct ctgggaatga gtttcttctc  96840
cctttctcag aaagatggct tagattgagg ccagattgtt ccggatccca gggtcccagc  96900
ctcacccatc ggcgaacaat ttgagcctgg aggtaaaccc cagtcccttg gcagccttcc  96960
tcggacactg gctttctaat ctttgcacag aaatagcagt taaacccctc tctggcttta  97020
gagatctaaa aatattattt aagaacgagg ttccttctca tgatgtcttg ttttaactct  97080
gaaattctgt ggtcacatgt cttggaatcc aatgaaccca tccagttcca gcgtgtacaa  97140
cagagtaaga gaaagacttg gttttatact gagacattct agaaatccag gagttcttct  97200
aggcattctg ttgctacaga agcacttttt ctggacactt taagtcgagc agtggtttct  97260
gtctgttccg cttacttaag tgaacataag catgatttgt cttttaaaag gtaactgttt  97320
tagtactcag gtagaatttg tgctttttcc ttccctacat actttcctac ttaaaaaaaa  97380
aaaaaaaaag aggaagggag ggtttccagt tcaaattaat gcagaattga agtgcaaagt  97440
cattacgttg acttgtagac attttaaaaa tgagactgtg gagctggcca gacatggtta  97500
aattttaaag ctcactagca tcttttcatt tctgcggctg ctcagccaca tctttcgaag  97560
ttatttgcaa atttattttt acacttttct gtgggagcat acaggcttcc tgttctcggc  97620
tttgctccgc accagtgaaa ggtcagctgc catcgttctg tcgccagcct ggtagcagct  97680
cggcctggtt aactaaggta ttaatttgtt attttccttt tctgctggag tacgcacccc  97740
tgggacgggc agctgagatg ctgaatggtg tcctgtttat gtagaaatcc agctcatttg  97800
agcacggacc tgctagggtc ttattagaca gacagttggc caaaacccaa catagtcttg  97860
ctggccgaat ggatgcaggt tcgaatttgc taagttatgg gacagtttat aacatggact  97920
```

-continued

```
gcgtgcaggc aggatggtgt ctctcaaccc tggaagtagg acttgcagct ttatttgcat  97980
tacgaatcac gtcagcgtgt gatctgtatg ccatgcatgt gtgcgtgcct tggctataaa  98040
atgctttttc tttcttattt taaaattctc ttccctgagc aataatatgt gggtaagaag  98100
ggtatagttt ggagaacggt aaaagagaaa atatactttg tcttggtcac tgcccgggaa  98160
gtctgctctg acaggagggg tgttattttc agctctacta gagtccagct tttgttctga  98220
gtcctcttag acgtcctcca gggagacgag tgctgctcag gatagtcgac atatcacagt  98280
cccagcattc aggcaggcct gtgatggcga tcacaaccct gtccgcctgc attctctgtc  98340
cctctgagtc tgaggaatgt gagcaggtgt gtccacctgg agcgagggat gtcctgtggt  98400
gacacatgac tctttataga ggagtaaaac ctaaagaaag catctctcac cagaacaaga  98460
gggtatgttc gttcactgaa cacgagctgt gtcccaggcg tggcactagg actcaggagg  98520
ggctgtccac cttgattcag ccatccctcc cagggtaggc ccctctgctc gctccccagg  98580
accccccttct ctgaagctgg agaaccagct gtgagcctca catgctcttg ggagcgtggc  98640
ctcctgccca gccaccccta gtttctcctc ctggccacca tttaccaagc ccaagtacat  98700
tcaggtgcct ggctgtgatc tgccgagaac ccctgaaatc tatatcatgg tgtccatttg  98760
catatgaaga tgctggagtc agagagggag catttttgtc ccttttccca tgccctcagc  98820
tgccctcccc atgttgaggt accccagccc cactgaaacg aacaaggagg aaactggtct  98880
ctgttggcct tcccgtcaca tcttcctgtg tgtgacacag accagacccc caccttccct  98940
agacagttgg cccagctcaa acgtgtgcaa ggaaggtgct gagttcggaa gaggatctgg  99000
attgctctca ctgtgaaatt gattctcaaa ggttaggcaa atcggctact ggagtcctgt  99060
ggtgggtggg tgggtgtgac tttcctattc ctgccataac aaattatcac aaacttagca  99120
gcttaaaaca gcacaaattg atatctcatg gtcctgtagg ccagaagtcc aggagcctca  99180
gccgagtctc tgctttgagt ctcacgaggc caagaccaag gtgctggcag ggccgtggtt  99240
ccttccggag gctcccggga gaatctgttt ccttgcccac tcgggctgtt ggcaaaactc  99300
aggtccctgt ggttctggga ctgagtttcc catttccttg tgggctgtca gctggggccc  99360
gttctcagcc tttggaggcc acccacattc attggcttac tcctcagctc cctcttcaat  99420
gccagcagcg gtgggtccag tccttctaat gcttcctctc tcaaacagcc ttgctgcctt  99480
cctcttccaa ggtggagggc cctgtggtgg cagcaggtct actcagataa tccaggataa  99540
tcttcctggt ttaaggtcgg ctggctacca accttaactc tatctgcaaa gctcattgga  99600
ataacaccag gggacaaaga tgatggggcg acaatcccac ctagcacacc tgaacccaca  99660
caggctgaac ccccagcacc cacttcccgt ttgagtccaa cgggagatac acgtcagcct  99720
gagtggtagt gaggtccaga atccatccca cacccagcct gggccagtgc ctccgaggag  99780
ggcaggcaga gcccccagct agcggtacct gccttgttgc cctgtgcagt aggccttggg  99840
cggtcaagaa catgccaggt tgatctgctt cttcaggagg acgtcctggt ggagaaccca  99900
gcttatgacc tactggctaa aggcagaaac tctctctgag ccacctgggt atctctagct  99960
gctctgaagt caggggggtga cttaggggta gctagtgtgg actctgatgg ttttgccgtg 100020
ggtactctcg gctgttggtg acaggccaca aagtccggca gacccaggga tgagggcttg 100080
tggggtgcgt cttggtttca tgttgtttta ccattttttc cacatgcgct tctgcagtag 100140
agagggaacc agctgatcta ttattatcaa agcgtacggt ctgtgctccc agctggcctt 100200
cttgcccctg cctgtcttcc tacaaagtga tttagcaggg agcaccagat gttgtggaaa 100260
```

cctgtggttg ccgagatgca tttgcctaac accttatttg ttcccgagac ccagggtcac 100320
gcttgccagt tagtggcacc tgaagtagcc cagccttctc cacagagtga gttagcctgt 100380
ctgccatcac tgcctcactg tgcttctctc tcccccaggt caccacggat ctgcgtcagc 100440
gctgtaccga tggccacact gggacctcag tctctgcccc catggtggcg ggcatcatcg 100500
ccttggctct agaagcaaag taagttccca cttacctttt tctaaaaaaa aaaaatgttt 100560
agattgtggt aaaatacaca tgacattggc cattttcacc ctattgaagt ggacagctca 100620
gcggcattaa gcacattcag tgagtcgtgc acctgcacca ccatccctct cccagagctt 100680
cgtcttcttc ccaggctgga accctctgcc cgttaaacag cagctgccca ggttagtcag 100740
ctcaggctgc cgtaacagag tcccacggac tgggcagctc aaacaacaga aatttagttt 100800
ctcaaagttc tggagcctgg aattcctgga tcaaggtgtc agcagggttg gtgtcttctt 100860
ggcttgcaga aagctgactt ctccccttct gctgtgtcct ctttttataa ggacactggt 100920
catattggat tagggcccac cctaataatc tcattttatg ttaattacct ttttaaaggc 100980
cttatctcca aatataatca tattctgagg tactggggcc taagacttcg atgaatacat 101040
tttggagggg acatagttca gcctataaca ctccccattg accccccgcc ctagcctctg 101100
gcaaccacca ttctactttc tgtctctatg aatttcattg ctttaggtgc ctcatgtaag 101160
tggaatcaca caggatttgt ccttttgtgc ctggcttatt tcacttcaca taacgtcttt 101220
aaggttcacc cgtttgtaga acgtatcaaa atttccttcc tttttttagg ccatcctgat 101280
gggcgtgaag tggtttcttc ctttcttaaa gcccaagtct cctgcccttt gtaggacaca 101340
ggggctggct gggccagagt ccaaggcctg cctctgattc tgcacctcac agcaaatcca 101400
cactttaggt tgcgctggct tccttttagg aactttcatt tataaattaa cagtcaagaa 101460
atctcttgag ttgcgtatgt gttgttggtt cagaaagaaa agcaagttaa ccgcacatgg 101520
agtcatagag tcaaaaccaa attgtacttt agtcaccaaa actggcagag aacaaaccag 101580
ccctctgcag tagtcatctg ttgtagatga gttttcaaat aactcaaaaa gaatggttgg 101640
gatgcctcaa tgcttgtaat tacgtgtgtt tgcatgtgga tttgcacaag acaaactgag 101700
cgtaacactc aaatgctacc aatgtaacaa aggaacagtt tgatattttt gatttccagg 101760
ccaaaatgtt agcttctgtg tcctgaggct ctttttaaaa attcttcata atgagttgct 101820
tgtgtggaaa ctcacattcg catactttac ccttccttgc gctgtatttt cctccattcc 101880
ttattggaaa catgcaaaga gctaaatgga aaacaaaccc tgctccgggg cgcattgtcc 101940
ccttaaactt ggtcagtggg catgtgaaag ctcagacggt catcttcctc atcatgttag 102000
ctcctcctca gacacataca ggggacggat caggcaaaca tcatttggaa caatgtcagt 102060
ctagagcgct cgacacttac aggattggtc aaggaaggaa cggttgatgt ctgggaattt 102120
gaaaacctgt gttgagcaga cctgtagcct gggatagctc tcgcctgtgc aggttggccc 102180
caggccgcct tctctctctg ttcactactg ctgtggaagg aactggggca aagccagatg 102240
gttctgggtg gagatgctcc ctgagagtct ggggagggcc cccagacagc gtggggccag 102300
aatgaaggaa aacccatacg tgttggaatt ctctaaaggg agtcccatgg ttttgggaca 102360
gtcttggtac ttttcaaaca tccgttcttc atcaaaaaac attttcaaca tcctctctta 102420
gacatatttt ccatgcggtt atatttgtga ttttattgct agagtcaaaa ataaaataga 102480
ttttttcata agaaaatggt tcctaacttt ctcactccct ggacccattc tgtcctccac 102540
tccaaaggtc atcccggcac ctaaattcaa gatttccagg aggactggct gtagccgtct 102600
tcgagtacgc cctgctgaca cacagcagta acttgccagg ttgcacgggc agcatggggt 102660
gtggccatgt cagcacttgt ctaaactcca aagcctgcac ctgtgacctc tctaccaggg 102720
tgcacggcca tgggctactc gaggcctcag aatctcccct aacagtgagg ttggcgtgtg 102780
ggccgcagga aggccagtgg atgcaggagg agaacaggtg tgcctggcag ggaaagtcct 102840
ggagactgag ccactggaca cggacgggga gagacggtga ggaagccagt gaccagccag 102900
gagcagcaag aacacattgg agaagtcagg ggaggccagg gctggagcct ggagagtgtg 102960
agcccaggga aggagtatac ccaagactta acgccatggg tgagcttctc gtaggaaaac 103020
aggcaaagag ggggccgagg gtgggagtgt gcagagcagc cgccatacaa aacagtgtag 103080
cgcgtccttg aaaaaattaa acagactccc cagacgatca gcaatcccac ttgtgggtga 103140
tatccaggat tgaaagcagg gactcgggta gataccggcc cagccatgtt catggcagca 103200
tggttcacaa cagctgaacg gcgggagcaa cccgagtgtc catgatggac gaagagatca 103260
gcgaagtgtg ctctgtacac acgtggaaca ttcagccttg aaaggaagga gattcggata 103320
cagattatga tgaggtccct caaggacgtt gtgctaaggg aaataagaca aatcctgtgt 103380
ggttccactt acacgaagac ctggagccat caaactcata gagacagaaa gtagcgtggt 103440
gcctgccagg ggctgcagaa ggagcgatgg ggactgagtg tcccgtggga cagagtttca 103500
gtctggaggt ggtgaaaagt tctggaggtg ggtgtggcgg taccagagca atgtgaacgt 103560
ccttaatgct actgagctgt acctttacaa atggttgaaa tgggaaagtt tgtgttctgt 103620
acgtcttcgc acacccacac acagagtggg ccactggaga gacgcctgtg acatcccagc 103680
aggtgccact ggggaggccg gggcagctgg gtacttcagc tctctctctt ctgcgtctcc 103740
aggcccccctc agctgcagca gctcccccga ttttacttag tccgtgttcc tagggtcaca 103800
ttccctgagg cagcacctgt ggcgcggcgt gcgttcctag taaacacgca ccgagagcac 103860
ggtgtgcgtt cctagtaaac gtgcaccgag acaaggctgg ggcttgtgct tctggtcacc 103920
tgcatcccaa cgagccctgg gaagatggtc tggaaggaaa gagtatgtgt ttgtgatatt 103980
agggagtgag agtcttggac tcgagagatg ttcgtttatt cttggttaat tttctgattg 104040
aatagaaagt cctaggtagg catcaattta accgactaaa aaaggaataa aagatctata 104100
aatatttatc tgtcaaatgg cggccggaac catgagccca tacatctttc ttttcactca 104160
gctgtttgat agggcaaaaa tatattcctt tcattactga ttcacatgta ggtgttatct 104220
ttaccatgtt ttaaagcagc cttgcagaaa gcttgtatgt tcaaatatcc aggttgcata 104280
gcatttaata ctgattagaa gaaaggaaca atgctcttat tttatactat tctctgtgta 104340
cagatagtat gaaaaatact atatttcatc gaatccaaga tgccataaag ttgtaagatg 104400
cacctttta tgtaccacag aaaccagaag tgctgccatt atacaatgca tccatatctc 104460
ttagaatttt tgtaactatt gaagagttct tttaggctga gagttattta gacctggaaa 104520
tgacactgtg aatagacagg accaagttca gcacctccag gcaatgtaac ccgttcctgg 104580
ttgctgtggg cagaggggct tataagaggt atcagatcat aagatggatc tggatttcag 104640
aggtgttaaa aaaaagaaaa aggtgggcca ggtgtggtgg ctcacacctg taatcctaac 104700
actttgggaa gccaatgcag gaggattgct tgaacccagg aattcaagac cagcctgggc 104760
aatatagcaa gacctcgtct ctacaaaaaa tgtaaaaaat tagccgggtg tggtggtgca 104820
cacctgtagt cttagccact tgggaggctg aggtaggaag actgcttgag cccaggaggt 104880
cggggttgca gtgagccaag atcacaccac cgcactccag cctgggcaac agggcgagac 104940
cctgtcttac acacaaaaag caggggtgag caaatgtgtc ttagaaattt taaaaaatca 105000

-continued

```
tctgtgtatt tagttacatt agtggcatgt tgtattcttt tgatgaaatg tttctacttc 105060
cccaaaaaga atattttgca aatttagaat catatataaa atcttgaatt ataatctaca 105120
gccagtgggt ccacacagga tggaatctcg gccaatcgtg gtttgaatgt actcttatgc 105180
actgttgtat ttgcttagga tgaagaataa ccccaagtat ttaataaaca tttactatta 105240
tgttaagtgt cttgtatttt cagaatttcc catatggctc tgggcaaact caggcagagc 105300
ttggcagcaa ggctaggctt taatgcttat gaattttggg tcacccattg aacctttttt 105360
tccctcagga tttagttgcc ggaaacttgt ttacaaagag gtggtgaaat aaacccttgc 105420
caaggaatgc agtccttagc ctgaggggct tgctgaagtt cagacgtggg ttggctgccg 105480
accccctgcc tctgagtggc ctgtgtggct gccgttgttg agctgtgtgg actctagggt 105540
gtgttgtgtc attgcagcag ccagttaacc tggagggacg tccagcacct gctagtgaag 105600
acatcccggc cggcccacct gaaagcgagc gactggaaag tgaacggcgc gggtcataaa 105660
ggtgcggcag tggcgttctg gtggaccatt gggtggccct ggaatgtgta ggaaggggtg 105720
tcatgaattc cttaaaagga ctctccaaat agcattagtt gttattatta attgtgtgtc 105780
acaagaattt aaaacgcatg tgcagctatt taagaaaagt atcccggaag ctcacagtga 105840
cattacggaa gaaccctcag gtcacaagag tctggggtct cctatactct ataactttgg 105900
ccacaccgag acaccaccta taccaatatt tactcatagt tctctttaag ccaggagcaa 105960
tgacgtgtgc ctatagtcgc agctactagg gaagttgagg caggaggatt gcttgagccc 106020
aggaatttga gtctagcctg gacaacacag caggactcca tctcttaaaa aaaaaattac 106080
ttcccccact actttttttt gacataaaaa aatgtatttt aaaaggaaac tgtactacat 106140
ctagttaatc ataggtttga tatgtagtta cgtatttttt ctaatgtgca ttaaaacaaa 106200
tccataatta ttaaaataaa tgttgtttgt gtgccacctg agggcagctt gcatccttag 106260
ccctgagtag ctctgtgatt ttgaaacttg ccttcagttt cctcatctgt acaatgagga 106320
cattgagata gttttgtaag ttactttcta actgtaaaac ttcttttggc cagtccctgt 106380
gttataaaag taaatcatag gacagtgggg cctctaccct cagcccagcc tggtacagac 106440
ctaggtacca tgaaatcaac ccagggtcag ggcttcgtta ggctggctgt tggcggcctt 106500
tgaagcaggt aattttagga cagtgctact ggctttgttt gcctgacttc tttttttttt 106560
tttttttttt tttgagacag agtctcgtct tgttgcccaa gctggagtgc aatggcacga 106620
tctcggctca ctgcaacctt tgcctcctgc gttcaaacga ttttccttca aataatccct 106680
cccgagtagc tgggattaca ggtgcctgct accacgccca gctaattttt gtatttttag 106740
tggagacggg gtttcaccgt gttgcccagg ctggtctcga actcctgacc ttgtgatcca 106800
cctgccttgg cctcccaaag tgctgggatt acaggtgtga gccactgtgc ccgacctgtt 106860
tgcctgactt cttatcaggt atactgaaaa atatttcatt tggccgtagt atttatgtta 106920
gggaggaatt tttttttaac cttttctgaa gctcaggtct aactaatttg acactaagtc 106980
tgatactact atctgtaaaa tataggtcaa gcatagttac cctaagtgcc gagggacatt 107040
ccttttaata aggaggccat cgattgggct agttcatctt tgttttgcag gaatgtcggt 107100
ggtagtggtg tactgtaaca agagctgacc cacattttaa ttctggccta attaaatagg 107160
agaatagatt gtatgcagtt cttgaccttg cctcttaaat taaactttga aagtctcctg 107220
ccctggccaa attaaatact ggaccgggcc agttcgcaag cctgtctctg tgctgtgctg 107280
ttttcccgga atgctctggg aactcagcag ggaaagaaaa tggcaaaaaa gatgagtaca 107340
gccttgtgtt attgcatttc gggcacgtgg taattgtgtg aactgagagg tctcagattt 107400
```

tgtttctctt gtctggtctt agattcaggg agcatagatg ctgacaagcc cttttaatgt 107460
aaaggaacct gtctttgtct caaaaaaaga aactcctaga ccttctcagc acttctactc 107520
tgtaccaaag cgggacgtgt ttcctgaccc acactcctaa atttagcaga aggagttggg 107580
ttcagagaga gtgaggcagc tgggaccttt gagcagccct caggggggacc cgtcctgcag 107640
cctggggccc ccaggagacc tcgagtctta cggtccctct gtcctccatg ggcccggca 107700
gatgcaagag ccagccttgc tcccttcctg ggagaggcag gagagcctgg ctctgaaggg 107760
cctgtctttt cagttagcca tttctatgga tttggtttgg tggacgcaga agctctcgtt 107820
gtggaggcaa agaagtggac agcagtgcca tcgcagcaca tgtgtgtggc cgcctcggac 107880
aagagaccca ggtaaggctc tgctgtggca tcggtgactt ctcaggcacg tgggtttgga 107940
gctgactctg ttgtaaggtg tggctggggg aggtgttcac acatgcattc tgtgcacatg 108000
tgcgtgtgca cgatgcatgc ctgcacacgt ctgcgttttc tcttgtggat tgtacagctg 108060
ggaaaggaat cacttcttaa gccaccactg ttttgaggcc tcttcccctt ttgtagcaga 108120
ttgctccacg ataggggatc agttcctcag cctgaaccac tcagcctagt attggaaatt 108180
cttacccgtg tttagcatgt cagcccaagt caggaatctg ctcctcccag aaagtgaaat 108240
ggggagtagc tgcaggtgtc ctttctgtca ccaccggcta gagattggag ctgtagcccc 108300
agcccagcct aactggccct gggagtctgc agtgtgaatc caccaggcct gagcaggagc 108360
agctgggtca gcctcttctc tgttgcaggt tgtggggtac tgcttattat tcacagagca 108420
tagcagcttt gtgtggcttt tatctggctc cgtacaacct tcttaaggct taagcgctgg 108480
gatttttttta acaaggctcg agcagaaggg ccctggcttc atctctctcc cgtgagcagg 108540
gcacacccgg aactgctctt tggagtaagt gtttctaaat ctgttatatt tgttcattga 108600
ttgattgatt gattgattga gaccgagttt tgctcttgtt gcccaggctg gagtgcagtg 108660
gcatgatccc ggctcactgc aacctctgcc tcctgagttc aagccatctt cctgcctcag 108720
cctcccgagt agctgggatt ataggcaccc accaccatgc ccagctagtt tttttgtatt 108780
tttagtagag atggggtttc accatcttgg ccaggctggt ctcaaactct tgacctcagg 108840
tgatccaccc gccttggcct cccaaagtgc ttggattaca gatgtgagct accgtgcctg 108900
gccaaaattt ttatttaaaa aaaaaaaagc agccataaag taaatcagaa agcaagaacc 108960
ctagcccact aggagaggaa atcagattat tccaattctg ccatcgcagc tgtttttaag 109020
gagaacggtg tttctctggg ccttgtatct gatacagaac ggagtgtgtt tttcccataa 109080
ctacttgttc cctttggaaa acgtgtttga aaaagaaaca gtgtgatgac tgaaagtgat 109140
atatttcttt atcaacaaat acaggtcact ctctttagat gctcttcctt gaatatgcct 109200
ctactcttgt aatacactct tgccacaaat agttgagaaa aatgtgtctg gtggagggct 109260
cgcatatggt aggagtgcag agagtgtgtg ttggctgagc agctggatga atagccacag 109320
aaggatcttt tgaaaaatca cctttttctc ccgtggctaa ttgcacactg accgctgagt 109380
ggtcactgca ggcccccgaca ggtcggccag acacctgaca agcctcagtc ttgacttctt 109440
aaggcgtcgg tttctctgag gagccttaga ctgtcaaatt tgaaacaacg tgggagagtc 109500
tctgagataa aggaggtttt gccttctctg tctttgctgg aaaacgcctg cagcctggac 109560
cctcagaggc taggtgaggg aggtgggctc ctgggtctgg ttcctgacct gggggctgcc 109620
ctctgccccg gcgcctccgc tcgtgtcccc gtcagggcgg ctcctgaatg aagcattctt 109680
ctcctgccag aaatcgtttt aagatggcag agtggtgcct aggtggcgag tggttgtttt 109740

-continued tatttttatt ttattttgtt ttttaagtga aagcacacgg agtctagaca gcacaggttg 109800
agggagcccg ccgtcacata cagtgtaaca ttgttcctgt cctttgagga aagtaaggac 109860
cctccaaact ccaagaggag aagaatcaga cttctgtttc tgaagaaaag tcatctttac 109920
ctttagcagt ttcagactct ttctgggata ttcagccagc ctaccgtctc acaccacttg 109980
cttatcagat cacttgctta actctgtaac gtggttgttg cagaggacat acgggcctcc 110040
agagagaggg gtgttaccaa gcagagttcc atgcctcacg tccacctgtg ggtctcccct 110100
cctggcaggg agctccagcc agctctgcca ctgagcctgc ctgcaggtcg gggtcatctg 110160
cacctgagcc gcgagtatcc ccacagctat gcgagttttc cccatcgggg ttcccagctg 110220
ctaggatcac gtggccgaaa atgaaaagga agcgttccca cacagccatt ttcccgtctt 110280
cttctaactg ccccctctcc gtgcacgttt gtgggtccag ctgtctactc tcttggcctc 110340
attctgattt cttcctctca tggtggaatc ctaggacttc ctgaatgtcc tgaacctgcc 110400
ctaagctgct tcccatggtg aagagcagag caagagggaa gacagagtgt gtgtatgcct 110460
ctttatacac ccctctcgtg tgcatccgtg tgcactgcgt gggatatggt gactgtcttt 110520
tctcttgaac aggagaggat gctaccctgg tgtgaccaaa ggtcagacag ctgtgttcac 110580
tggatgttaa gcacgggagt cctctagctg gggcatgtgt ccacacctgt caggtctatg 110640
gtgacgtcac acatggtcct gagggagagg ggctggggtg ttcatacgtc cacccctctg 110700
gtcacgggca ggggcaggaa acctctgtct acccccagcc gtgggctgga atatggccat 110760
ggttcaggga gactgtcctc atggcggtga ctgacaggaa gagtcaaatg ggctacccct 110820
tctgcatgtc cctcctgtgc acccagcctg tgctcccaaa ctagcattgc atccagggcc 110880
ccgaatgact gcacagagct ggtgccccgt cacccatggt gtccccctgc ggagctgctg 110940
tctccaacgc tgccccagtg gctggcatca cagccccgcc tgcccgagtc atgctcaggc 111000
ccaaaggcgc ggaaaggcca ccagcacagc acaatgcggg ctgcagagga aggagctggg 111060
gcggtgatgc cagacccacc agacacagtc cccttcagga ggcagctccg tcatttgaaa 111120
aaaggccatc catggtgtga aaaggactag ccaagagggg accccaagtg atacgttggc 111180
atttctcacc tggacactgc acatctgggg actggggggt ttgagcctgt ctgtgtatgg 111240
atccacccga aagataagaa gaagtccctg gaagggtaga gaacatcagg gaagagggga 111300
cctcaggtag ggctgggcct gggtgagaat caaggagcca ggccccctgc tccaaggtac 111360
cacgggatcg tgctgggcag tctctttact gcctggtgtt taccctgccc tagagcagtc 111420
tgagccccag aactgaggta ttgatgtctg agccacctct ccaggagccc acacggggta 111480
gggcccatca taggctttca ggaaatgcta aagctaaatg cagaggcgag aggaaatcac 111540
ttaaactgaa tggcagctgc tgttagcaaa agagagtgac ttgctagagt cctccaggat 111600
agcactggat gaaagtgcca gctgtgcctg ggcctctgtt gtgatcgtca gaccgtagac 111660
cagaggcacg tcgacctact cctgggcaca aatggtttcc atctgtttag aacctttgtc 111720
aattaaacga aggtacatag gatcatgacc aggggcatct gcctgtgcaa aatgatttta 111780
aaatctgtgt gtattaaata gaaagataaa gttgatattt ttatatcttt tcttcaaatg 111840
aaaaagaaaa ttaagcttag tattattcca acgaatgaaa tagaggccca gctattaaat 111900
attctatttg actcttgatt tttctagcca gtgcttctgt cgctgctttg aaaatccagg 111960
cttctgggaa acagtgtatg atatgcatga ctcccacctc agtgctgggg acactcacaa 112020
caacagggtc ttttaaacca acacaaagcg ataacttacc tgcacgtctt tagtttctgc 112080
tggtttggaa ggttactgtc cagacagagc ttacagttta gcttggcctg tcttttaatg 112140
aactcttcac acacccacaa cccacacaag acacttcaga cccaaaagcc aatgtgttgc 112200
tttgactatc aaggcttatc tgtagagcag ataatctttt tatagatgtt caggaattaa 112260
ctctggatta gccgcatatc acctgctttt ctggaatttc gtgaaactag actgcgtatg 112320
gcggtcattt taaaacaact ctatttatga agacatatgg ctgtggatga gagataatgg 112380
attgtgatta taaaggcact tactgtgtgc caggcattgc tctaagcact ttatataaaa 112440
atccccaata aacatgtgag gttggagttc tatctttatc ctcattttat ggaggaagaa 112500
atggaggcag aaaggagtta ggaacttagg cccagaggtg gggtgctgtg gggctgagct 112560
gctcccgcag gctgcttgtc tccagagtcc accttgcccc cctaggtagg agctcaggcg 112620
gtactgagcc aatgagagcg acctgcccac ccgttagaag acctcacctc tgtgacctct 112680
gtgccaggag ctagctgggc gcaccacctc cagggatgat aaagtacctg accctggctg 112740
cccagagctt cctccggcct tggccaggtg ccagtgccta agagcacagc tgctggcgtc 112800
tcatctgcgg caggtcagct gggcaagctg gtgaggccag gagcccagcg gcctggtgga 112860
gtgccgtgcg gatcagacac aggtcaaccc agctctactg tgctcaagca cacagcctga 112920
tgtgacgtct ttttaggaag ccaagagccc tcgttttctt tgggctgtct cagaactatg 112980
caggtgtctg ccaccctccc atcccctcct caccttaccc agcctctccc tccagggcat 113040
ctgacctctg tgtatacctg ggtaccacag gaggccctta cttctggttt ctcctcttgg 113100
gctgttgtta tacagagcat gcctgggtgt cctcagaaga tctgtggggt gctgtgcagt 113160
cccgccctgg gggtaaccac agtggaccca caacactttt cctgcctgct gctacccctt 113220
gtagctgcga gcaaacttaa ccagctggtt atgttcttgc aaccctttcc cttcctggct 113280
tagttttgaa gcaaacttct tttccccaaa ttgtaaaggc tacttatttc taaaattagg 113340
atttggaatt tgaatacagt tgattctccc tatttgtggt actgttccac aaagtcacca 113400
cgaacactga agcgttattc ctaggagaga tacagggtta agttcctgtg agcctccggt 113460
cacatttttg ccagcctgtc catatagacc gagctttatg tgtatgggtt taaagacagc 113520
ttatttaaca tagatcattg gttcattcac tttagactca cagcggacag cactagtgct 113580
cgttgctgga accaagcttg tcttacccgt gtgttttctc cttaaggcag gtctctgctt 113640
tctcatgctg tttgacacta gacagtgttt cagcactgca cttggggcca tttcaaacag 113700
tgaattcacc aacagaaaag cacagagcca ggcatggtgg tttgcaccta cagtcctagc 113760
tactcgggag gctgaggtgg gaggatcgct tgagcccagg aggtcaaggc tccagtgagc 113820
taggattgca ccactgcacc ccagcctggg tgacagagtg agaccctgtc tctaaaaaac 113880
aaaaaacagc acaaaaatgt gaaaaatgtg gcactaaata cactgtgaaa cagacacttg 113940
tttttatttg agatggagtc tcactctgtt acccaggctg gagtgcagtg gcgcgatctc 114000
ggctcactgc aacctccacc tcccaggttc aagcagtggt cttgcctcag cctcctgagt 114060
agttgggatg ataggcacat gccatcacac ctggctaatt ttgtattttt agtagagacg 114120
ggctttcacc atgttggcca ggctggtctc gaactcctga cctcaagtga ttcacccacc 114180
tcagcctctc aaagtgctgg gattgcagcc gtgagccacc acacctggcc agaaatggac 114240
acttatttat ggcatgagag ctgcaccaac aggcggtgtt gccttgtttg acctcagctg 114300
ggagtgtgct cgttgggggga ctcattatgt taccactctg cacacatcta cacatgacac 114360
caaagtgccg caggtgttag tttgggggat acaaataaat gtcagccacc aggtgaatat 114420
gcagatacag catatgtgaa taatgaggat tgactgtata ttttattttc tcttttactc 114480

-continued

```
cccttcaggt tgaattgtag actgttagaa ttggaaggca tctttaaagc cagctaattc 114540
agtcccctca tttaacgtac aggaaaaagt gtgctataaa tttaagcatg acatattaaa 114600
gcaccttctg acccaattaa ctgtggacgg cattgtgtaa gttaatgtac tggattagct 114660
tttttttga ggttaaattt tatttctcac ctaagtgatg tgctatggtt tgatcatcaa 114720
aagtaatttt ggccgggcgc cgtggctcac gcctgtaatc tcaacagttt gggaggccga 114780
ggcgggcgga tcgcctgagg tcaggagttt gagaccagcg tggccaacat ggggaaaccc 114840
catctctact aaaaatacaa acattggccg ggcatggtgg cgcatgcctg tagtcccagc 114900
tactcaggag tctgaggcgg gagaattgct tgaacccggg aggcagaggt taccgtaagc 114960
tgagatagca ccactgcact ccagcctgcg gacagagtga gactccatct caaaaaaaaa 115020
aaaaaagtaa tttcatgtga ggaaaattct cagtctgaac tcatatgaat aaggaagccc 115080
acagatgaat gaagcagctt acctcagagc ctaacgacag tcttgttgag agcgtgcatc 115140
ctggaacaca ggtctgagaa gtgacctaga agcctcttgc caccttcaca cgggcactgt 115200
gtgccctccg acctgctgtt ttcctattgc ttaatttagc aagtctgtcc caattaactc 115260
ttgccattcc attcactccc gttagcgggt ctgtgaaagg gtttcctgga tgaccttctg 115320
ctgtaatggg cctcagttct ttagcctctc ctccccaagc caggtgccag cacagcagct 115380
ggcaggatgc tgctggctcc tgattctgga gggtctctca acatggccct agaacattca 115440
tgggcccagt gaggaacaaa gcaagtgcgt tgtgcaagga tccaggttgg tccaggaagc 115500
caacctgggg agagggcttc aaggagggag tgagaaatac tgacatggag tagcttccca 115560
ggtagaacag gaaaagtgga gagcttgagg cggagggttt cagcctgtgg cccgtcttcc 115620
tgcttcccct ggcactcggt tacttgaaaa tatttatttt tgctattaga tagtattatg 115680
cattggaaaa aaaaatagga ggaggccaac atatctgtgg tctggagttc ctagggagtc 115740
agcagggtgg ctactgttgg tgggccttcg cctcctcagg agaagggagc gggtggagag 115800
catttgggat gaatggagaa catctgaagt accagagtaa ttaacgttga aatgtggctg 115860
cgtggcacgt ggcatttgct gtcattagag atcttttcca agtctggccg tctccctggc 115920
ttcaacaacg cacggtctcc aggcaggttt tgcgggatca tttaactccg tggactccct 115980
tagcgtcctc ggaagatggc tttatgtaca tagaccacag tttcagaagt taatagcaga 116040
agacactttt cagttacttt ggggacttta agatctttct aaatcagttt tcatcattaa 116100
agtacaatgt aggtgtattc acgtgacagt gataatctct gcacattgtt taacttgaaa 116160
gataaattac ttggcagtcg acttgcattt tcagcgttac cttagaaata actgtagggt 116220
ggagaaccac ttctgttttt ttcattgact gttctacttt ctgtcttgga gttaattttt 116280
taaagtgatg acttttgata gatggcttcc ttattttctt cctggagttt ctatctgaaa 116340
tacagaaaaa tttgagcaca atgatcatga aacattttga agcctcctct tttatttctc 116400
ttcttaataa aagcactcta attggggatg ttaggttaat ggtttcaata gcaaccacag 116460
aagtaaaatg tgtggggagc taactgcatg tcaggaaggt ggcagcgtgc cctcctatag 116520
tagctgtcct gggctcccgc gctgccccag aacttacagg aatgaggagt cctggtggcc 116580
tgtaactgag tgatttagca gttaagagct ttcacataaa aactaattgt tacagttagc 116640
cttgttccag gaggctgctg ggctcctagc ccccaggtga aggtaagggc atggctttga 116700
aaaccaaacg aagtgaggcc attaactcct gcaggagctg ggtgctcccg cccccagcca 116760
gcctccctgc aggcagcagc agcggggctg gcggaggatc acacccaacc cagccttctt 116820
tatgcagcgg ctggagtccc ttagcaggaa taaaaaagtc agatgcaaga gactttcata 116880
```

ctctgaaatg attttttttt tctaggtgtt cgctctgtgg gtggggctca gagtggcggg 116940
gcaggtgaga ggtggggctt ggttgtcttt cacttgtaat taccctgctc ccgttctctc 117000
atccctgtgc cttatcaatg ggattaaagc ttcttcacaa ggattccagg tctatttcta 117060
gagcagattg atcacttccc ctaccgatga gcaattggtt ggagtgtggg gaccgtgtct 117120
tcaacttggt taaggctttt gtgtctgttt ccccttgatc ttgctattca gcactggaaa 117180
ggtgttgaag tgtgagagtg tagggttatt cctggttttt ggggttgact gggagctaca 117240
ttttgaagcc ccaggggagc actgagtaag tctgccggca tagacgtttc tccgtctcca 117300
caccttgctt ctccctaacg tacccacctt acattcttag tgtggggtga aggtggggga 117360
tgggggacac tcacctggag agacacatgg gccctgcagg tcctggaact ccccagagcc 117420
ttctcttgtg ttcgccatct accgcagcgg gggctgctgg ccagtaaaca ctagcagtaa 117480
agcttgggag aaggcaatga aggaagtcag catctctaga tcaatttatg gtgcatgcaa 117540
agcgtgtttt caaatactta cagagtctcc gagggaatta catcactgtt tataactgtt 117600
ttgattgttt tttatgactc agggcccagt agagccaagc agtgtaactc ctgagaggct 117660
ctgagcagaa cgcctcatgc ctcccgggag gagagtccag gcataatggg aaaagcgctc 117720
cccgtaataa gccaagcacc ggtcgtgtgg tggggagtta ttaatgtgct gctgggcggc 117780
ggtgggtctg cactgaagaa tgccatgttt cttcagctgc agatcactgg ggtgggtcgg 117840
gggctgagtt caaagaggca tgaaccctaa tggcctggaa ttggcaggat ggtccagcct 117900
ggacacagaa acagccttgg ggtacagatt ttggatctgc ttggtctggg gagtctgctt 117960
ggtctgggga gtgtgtcaga aaattctagc aggaaggagt cttgaatgat tgaggctttg 118020
tttttaccct cagactccat cccatatggt aaagctgccc tgagtttgta aagggaacca 118080
tcgtccattt ccatgacagg gcaggaaagt gaggggaccc tgctttctgc aggagatttg 118140
ggagcacaca agcttggcac cctcgatcag catgagaggg cagcctccga actccgagct 118200
gtgtccttga ctgtgggtcc acgcgagctt ccattcgagg cagcgaggcc tggaggcgga 118260
ggcagtgagg cctggaggca gaggcgtggg ctctggggcc ccaaatccca gctcctcccc 118320
gcattagcta caccttgggt acagtcctta atttccctct ggattaaatg ggttaatcct 118380
tggaaattct caggccagtg ccttatgctc agtgcacagt cagcttggga aatgtttgct 118440
gattgctgtt atttagcatt gtgacttcta ttttcaatgc tagtcttcgg aacaaagtag 118500
tgggattttt tatttgtttg tttgttaaaa catttaatta tttttatata tttagggggt 118560
ccaaggacag gtttcttaca tgcacatatt gcagtgtggt gaggtctggc cttttagtgt 118620
acctgtcacc atggaggtca tactagggca actgagaaac gagctggcca aatgccaccg 118680
aggagaagcc gccttctggt caccaaaggg agcccatccc tggggacatt cacccaagtc 118740
tgcccaagaa cccatctttt attttatttt atttttgagt tggagccttg ctctgtctcc 118800
caggctggag tgcagtggtg cgacctcggc tcgctgcaac ctccacctcc tgggttcaag 118860
agattctcct gcctcaggct cccgagtagc tgggattaca gacacccgcc accatgccca 118920
gctaattttt gtatttttag tagacagggt ttcaccgtat tggccaggct ggtctcaaac 118980
tcctgacctt gtgatctgcc ctccccctcc ccccactttg tataagacaa aataattgac 119040
tcagcagcaa tgcaaggcag acagggccat cgtccagagg aatggggcct gtgctgtgca 119100
ccccacagca ctgcccagca gcctggtctc tccactgtag gcaagttgga gcggtggcag 119160
caggcggtgc ctcggcctcc caaagagctg ggatcagagg cgtgagccac agtgcccagc 119220

```
cgaaccatct ttcaaatctc tgtaagcaaa ttccagaggc ataaacgtct tcaggacagg 119280
tgataaagtt cacagtggag catccacgtg aggcagtcag aggctgctgc ggctccccgg 119340
ggcccgcagg gccctgaggc tgcagtgggg atagagtgga cgggcgctgg agctcctggc 119400
tgtgtgggtg agacttcatg cttccggtgc caagtgctga gccctccctt ctcccccagg 119460
agcatcccct tagtgcaggt gctgcggact acggccctga ccagcgcctg cgcggagcac 119520
tcggaccagc gggtggtcta cttggagcac gtggtggttc gcacctccat ctcacaccca 119580
cgccgaggag acctccagat ctacctggtt tctccctcgg gaaccaagtc tcaacttctg 119640
gcaaagaggt aaggcgaggc aggcgtgggg atggggtctg ggctcactga gattgaccct 119700
gcacaagagc ttctgtccag tcttgggccc acagtgtctc tgcaaggccc tctggcgttg 119760
gggactccca ctggttctgc tggcagcttc ctttctcttg gagacccttg catgtaggcc 119820
ccaaaaacct taaaagttgc tccctgaaac cttgccttcc aaaaggtcct ggaaaacttt 119880
ccttttcaga gagaagtgac aaaagagttg ttgtttcgtt ttttgttgtt tagcggaggg 119940
atttgtggaa ttctggctat gccttctttg cttagaagtg cattaaaggt catttaatcc 120000
tattcagttg gcttttgaat cgagcatgtg taccacaggg agcactgttt gtccccccac 120060
cagctctccc acccagtcgt gggctgccct gcagaacctg caccagcagg ggcctgtccc 120120
gggaatacag acaggctcgg gtggtatgtg gggaaggtgc tcccaggctg ctctctgcca 120180
acttctcttg cgctcagggg ctgggaattc caaagcttcg cacatggttt tttgggaggc 120240
tatggagtca tttctttaac aaacttagaa acaaggggaa atacattgat gcaaatatat 120300
gacttacagg taattagaat gaaggtgttt atgggaactt aagaggggcc agggtattct 120360
ggtaccttct gtctctttct agctaagagg tagagagagt aaagaaattt catggacaaa 120420
tcagcatttc cagcttctct caaaaaccag gactggcact gtgcccacat catctgcagg 120480
aagcccccca ggaccaggcc tgctctgtct tctggggtgt ggtccccttg cccactctgg 120540
gcccacttga ctcctttggt gacctgcctg aggctgtggc ccttgtgtag gctataggga 120600
gctgcagaga ttcagaaaca ggggctagcg aaggctctca gatggaacca ggcagaagtt 120660
gggggttgcc ctttgcttaa cccttcccct ccccaccact ttgtatgaga cagggtaatt 120720
gactcagcag caatgcaagg tagacagggc cattgtccag aggattgggg cctgtgctgt 120780
gccccccaca gcactgccca gcagcctggt ctctctgcag caggcaagct ggagcggtgg 120840
cagcaggtgg cgggcccggc accagctttg tcctcggtgc actggaatca accctgaggc 120900
agaccctggc accaagctca gcccatccca cattctcctt tcatagcacg agtgtcacag 120960
gggcacctct ccctcctgcc gggaggcccg gccgtgctgt gcctctgcct gtgggaggtc 121020
tcacacgggc acgagcagtt cggtgtcagc ggacgagctg cagcttttga tgctatgttg 121080
ctccccgtgg tgttttttat tttatttttt taaccttaaa gattttaaaa gtcctcattt 121140
ctggcatttc ttggaaagtt ggaagctgtc tgacaccagc cccgtgttcc tgcgtgcact 121200
gggccggagc tgagcaggtg ggcgagtgtg tgtccatgtg ctccatgttt tccgtgctgg 121260
cagccctgag gccagcaacg ggctctccgt tcactccagc cgcacaccta gtggcaccca 121320
ggtttgtgac ccctgactca gagccagagc tgggtgcagg cccaggtgat ggcccaggtt 121380
gacggagagc ctgtggtgag gctgagaggc tggggcagca ggtagcaggc aggcgggtgg 121440
cagtgaccct ggagagttgg cccacaccct gctcttccac tcctggctgg gctcccagga 121500
gccagtccct ttgcctctct ttattcctca tctctgaaaa tgccacttca cttatctgta 121560
aacattagga ctgttataag acttgagtgt gataatatat gtatccctgg cacaggggcc 121620
```

tggttgccct acgtgtcctg cttacgtccg gctacctgac ccacaagaac cttccgctgc 121680
cccagcctcc cctctcccgc tcccctgggg ccctgtttcc cttccctgga aactttcctc 121740
ctcctgctgc tgcccagtgt tgtgcccttg ggataataga gggcaggtcc tgccaggcct 121800
attgggagcc acccccttggc tgggtagtgc tgtccttgcg ccatcaggca ttttaaaaac 121860
taccctagcc caggaagggt ggctcacacc tgtagtccca gcactttgag ggccaaggt 121920
gggtggatca cctgaggtca ggagttcgag accaacctgg ccaactcttg tctctactaa 121980
aaatacaaaa attagctggg cgtggtggca cgcacctgtg atcccagcta cttgggaggc 122040
tgaggcaaga gaatcacttg aacccaggag gcggaggttg cagtgagctg aggtcacgcc 122100
tctgcactcc agcctgggtg acagaaagag agtctgtctc aaaaacaaaa aacaaacaaa 122160
caaaaactac cctgaggcta ctccagctgt catctgagtc ttgggacttt ggtttttttc 122220
caaggcagat tttgtgattg tatcaagaat ttgtgtttta ggatcaatga cctcctatcc 122280
tactgcacat cttacttaat ttagcagctt tatcagtttg ccaggttctt cactaagaag 122340
ccattgatgt gcctcagcac ctcagccctt aaaagacagt ttgtccttgt tctgtcccca 122400
gtgtgttggg ttcagcttgg catcgagtgt gaaaatcagc cttgaccttt gccatttctt 122460
agaagaaagc acaggatgct tccccctcac tcttctccat tgcaaagaat gttccctaga 122520
taaacatttt cctacattga gtgttcagag aacccccaga ttggaaattg aatcttacat 122580
cattcaaaac ttatgtattt caatttctga tgaacaataa agatgcctat gttaaaaaaa 122640
atgtttattc caaaatcgag atagaaaatt agactgtgaa gaaagaataa gaggaaaaaa 122700
cctggaattg attccagtac agaaagagtc acttctgagg atggcactgg gtgcaggaag 122760
agattggatg ttgattagtt gcttcctgtt tctgcctgaa ccaagtgtga ggcagaaggc 122820
ccaggggctc aagggtacag ttgggaaaga ccttcgagtt gggaagggta aagggaggct 122880
catcaggact tgcaaggagg gtactgctgg gggtgggga gctgtctcct ccccccgctc 122940
tccacgggcc cctcccattc ccactgaaaa gcaaccaacc ctgccattgt catctccctc 123000
aaatgcccct gttgagactg gatcagccct gcaggtgaag ggacagaact ttccccacaa 123060
gcttgagtag ctgctcctct ttccttattt gtgtctccca gagaacagtg cacacagctg 123120
gcttgaaatc aaacatggaa gtttcattct tgcacaaaca agcactttca aaaggcgtcc 123180
ttagtgagca ctctctgggc ttcggtgaag gtaccccagg gggacccccg cccctgtctg 123240
ctttcgtgca tccgggcact ggagttatgg tctctgtaag attgttgctg ggtgggaagg 123300
agccagccac cttctgcagg aaattgtcgg gactgggggc ttctgttggt gagagcttgt 123360
aaacatcttt cactgggtta tatgaaacct gcctgcctgc ctgccttcct ctcagaatgt 123420
taaggaggtt caaggaggtg atggaggaga gagtctgtgt aagagcttaa agacgatcac 123480
atttcactgt gccctttgcc ctcgggttgg ctggggccag acccccgcta ccctgggggt 123540
acggtccagc caggtcatac agtcccccga gagccctgct tgtgccagcc cctccgccca 123600
gccactcagt accagcacct tcatttctga caccacacct ccaattgcag gttgctggat 123660
ctttccaatg aagggtttac aaactgggaa ttcatgactg tccactgctg gggagaaaag 123720
gctgaagggc agtggacctt ggaaatccaa gatctgccat cccaggtccg caacccggag 123780
aagcaaggtc agtggctctt gggaatctca tgacagcttt tgtatctcaa gcctcttttt 123840
acctctgggc cttatttaac tacggagtct ctgataattc tttgttttgt gttttagagg 123900
tagaattccc ataacagaaa attcaccatt ttaattattt ttaagtggac agttcagtgg 123960

-continued cttttagtac atccacgatg tcatgtaaac gtcagcacta tctaattcca gaatgttttc 124020
atccccacaa aaagaaaccc catacccatg aagcagccac tccccattcc ctcctcccct 124080
cccagctcct ggcaacctct aatccactta ccatttcttt ggatttgcct ctcctggaca 124140
tttcatatag atgaaataat acaacacctg gccttttgtg tctggcttct ttcacttagc 124200
atgatgtttt caaagttttt caatattgtc gtatgcatca aaacgtcatt actcgtatgg 124260
ctaaacgata ttccattgta cggattgatc acattttgtt tattcattca cctgtgatgg 124320
acatttgggt tgtttctacc ttttagctgt tacaaatagt acagctatga ggattcatgt 124380
acaagttttt atgtggacct atgtttttgt ttctcgtggg cgtataccta agattggaat 124440
tgtcaggtca tatggtaact ctatgttgaa cgttttgagg aacagccaaa ctgtcttcca 124500
cattggctgc accctttac attccggcca gcaatatatg agaggtccag ctccttcaca 124560
ttctcgttaa cacttaatat tctctgcttt ttaaaaaatt ataagcgttc tagtaggtgt 124620
gaagtggtat ctgtggttct tcaattgcct gatgatgcac cttgatgcac aaaagtttta 124680
aattatgatg aaattcaatt tattttttct tctgttgctt gtgctcttgg tgtcatacct 124740
gagaaaccat tgcctaaccc aaagtcacag agatttactc ctgtgtttcc ttttaagagt 124800
gttatagctc ttacatgtag gactttgatc cattttgaat tatttttgta tatggtgtga 124860
ggtaggggtc caaactcatt cttttgtacc catttgttcc agcaccactt gctgaaaaat 124920
gcattcttta cccattaggt gatcttgaga ctcctgttgc aaatcaactg accacagaag 124980
agaggttcgt ttccacactc tcgattctgt tccattggtc tgtatatcta tcttggagtc 125040
agtaccatat tgttttgatc actgtagctt tgtagtaagt tttgaaataa gaaagtgcga 125100
gtcctccaac ttggtggttc tttctcaaga ttgttttggc tattttgggt cccgtgtaat 125160
tccatgtgaa tttgaagata agcttgtaca tttctttttt aaaaggtagt tggaattctg 125220
gtagagattg gatatgtaga tcattttggg gaatatttcc acattaacaa tattaagtct 125280
tccagtccat aaacttggga tagttttctg tttatttagc tcttctttaa ttttgtttag 125340
cagtgttttt tgtagtgttg agtatataag tctttcgcct ccttggtgaa agttgttcct 125400
aagtatttta ttattttat gctattgcaa atggaatggt tttcttaatt tttcttttgg 125460
attgtttatt tctctggtaa ttcttgtacc tttttaatcc cttttactta atgatcaatc 125520
atttatttaa ctagtcttta ttaagtacca aactctgatc taggtaatgg ggttacaacc 125580
aggaaagaaa actggaataa tcagcacatc ttattttgta gttacccaca aaggtctata 125640
aacgcctgtc tttgttctct gggtcgaatg catagtaacg tttacagaat gtgctgggat 125700
cttgcttttc tatgggcgag tttcctcaag gtttgctttc actgttccgt cgttccctgt 125760
gccctttctt gtgaagatgc agtctgcttc ttggtcaccc tgggagtgcg tgagaacctt 125820
cccctgccct ggttcttttc cagttctcca taaacaatcc aaaagcaaaa ttaaaaaaac 125880
cattccattt ggaatagcac agttttagga gaaaagaaga gtgttgactt gccttacgtg 125940
gaaaattgac tttaagtcat caagtcatct acagggatct gggacctccc ccagttgtat 126000
tctttctggt tttaaaatag taaataacta ttttaagaaa gcgttggctg ggcgcggtgg 126060
ctcatgcctg taatcccagc actttgggag gccgaggcgg gtggatcacg aagtcaggag 126120
atcgagacca tcctggctaa cacggtgaaa ccccatctct actaaaaatc caaaaaaaaa 126180
aaaaaattag ccaggcaagg tggcaggcac ctgtagtccc agctcttagg gaggctgagg 126240
caggagaatg gcttgaaccc gggaggcgga gcttacagtg agccgagatc gcaccactgc 126300
actccagcct gggtgacaga gcgagactcc gtctcaaaaa aaaaaaaagt gttataacaa 126360

-continued atcctaaaag tacaaaaatg taaaatttta aatgacctga aatttacaca ttttaatagt 126420
ggaagctcct aaattctttc ttttaaaagc cccaaagtgt attggccgag tattaaaagt 126480
caaggtttac tcctcatgcc agctgcatcc tcaagcattc actgcttcgt gggcacaagg 126540
cagagttctc atgccagcct gcatggcctg cttgcctggg aggctggtgc tgtatgcagg 126600
agagcacatg gaggctgggg ctactgctct tgtgtcctca tggcatagcc ctggaaaccg 126660
ggcacaccat tcaacactct agacctgtga tctttactct gtatcatgag ccgaatacaa 126720
cgagccctac ccatgtccca gggcagcttt gaggggacag tcaatccccc atggaactgt 126780
gcctctgcag gcagcctttc tcatgcatct cacgcattct tctctttccc cttcctatta 126840
ggccaacatg cgtgcactga tgcctctccc ctgagtccac atcccctcca gccaccaccc 126900
acttctctgc tccccttat ggcaaagccg gcagaacaag ctgcctgcca tggccatcac 126960
tggctcactc ccagcccact cccatccact gcacaaaata ccggggctcg tcagggtccc 127020
ccaccgtttc cacattgccc aagcctatgg tcccatctct gtcctcccca ggttgttaaa 127080
gccagggtct atggttctaa caaactaagc accctctctg gggaccacag ggtgcagtgg 127140
ttaagactgg gggctcagga gcccttctac ctgggggtag atgctggctc taactcttac 127200
aaatacctgt gaccttggca agtcacttag cttttctagg ccttggtctt cttatctaga 127260
aaatggggat agtacgcaag ttactgggtt gcggtgggat gaaatcaggt aagacaggct 127320
ggataccgag agcagggccc ggcacacagc gacgttggca gctcaccccc tctagaagtg 127380
ccctcttgca cagctgcagt gatgccacac ctgggggccc tctccacctc acaggctgcc 127440
ccttgtgcat ctcgttggct gatcctctcg cacatacccc tgcacgcact cctgggtcct 127500
ctgctctttg ttcccatcca gggatctcat ccagccccgt gacactgagc accttgtacc 127560
tgctggtggt gcccaaagct gcctctccct gccctcttgc acccagacct gctctgcagc 127620
agcctcctgc ttctgggcat gggtctaact ggctctgagc ttgtgcacct tagacaaact 127680
cccaaactgc ctctttcttg ctttccacat taatgtaaat agctttgggc tgggcatggt 127740
ggctcatgcc tgtaattcca gcactttggg aggccgaggc gggtgaatca caaggtcagg 127800
agatcgagac catcctggcc aacatggtga aaccccatct ctactaacaa tacaaaaagt 127860
taaccaggca tggtggcggg cacctgtagt cccagctact tgggaggctg agggaagaga 127920
atggtgtgaa cctgggaggt ggagcttgca gtgagctgag attgcgccac tgcactccag 127980
cctggatgat agagcaagac tccaactcaa aaaaaaaaaa aaaaaagctt caccttgcac 128040
tccattgctt ggccaaatcc caggagtgaa cctttaattc ttctttgtct ccttcaccat 128100
ctgcttccag aatatatctc agtctgccca ctgcctcagt tcagtcccct atagtgtctt 128160
acctcctcat tccactggcc cccctgcctc aacccctact ggctagagcc actctccacc 128220
cagcatccaa tgatcctttt aaaatataat tcagaaaatg atgcacccct gctaacttta 128280
atgacctccc acagctctta gagcaaaacc caaatctctt agcctgacct gcacatcctg 128340
ctagcacctc tccaccgtga atcatttcct gcgcctcatc attgacctcc gttctgttcc 128400
cctaacatgc ctggtcttac ctccatgggg ccttggcacg tgctgctccc tccttgggga 128460
cagctgtccc tagggcttcc catggctgca gctcagacct ggcctcatgg aggggtctta 128520
tctgaatgcc tgtggtggat gtcctaccca ctctcccacc ttacactcct acagaaacat 128580
aaaggcaggg gatgagaatg gggaggaata aaaatttgct gagattctga ttccacattt 128640
agtgggaggg gtgatggatt atgtcttact cttagcactg atagagacat ataaactcaa 128700
atatcttcct ataatagaga gataatcaag atttaaaaca ggatgccaac cttccagatc 128760
actagaggga aataagagtg aagagaaatt gatcaatatg ccaaaaaaaa aaaaaaaaga 128820
gagagaaaga actataggca aatttgaata gggatacgga agtcttaaat aaaacattag 128880
gaagtggaat tcatcagttt attcaaagaa tactcccctc caagaacaca gccttcactc 128940
aacagatact tattgagcat ttaccaagtt ctaagcactg gggatgcact ggtgaacaaa 129000
acagatgcta agcttacatt ctggaaggca gaggaggccg tgaaacaaga ttaccaggca 129060
ggaagctgtt gtccattaga tgatgagaag ctctaaggag aaaaatgaag cagggcaggg 129120
tgacaagggc atttcagggt gtaccgggaa ggcctcaggg aagggacatt tgagtaaagc 129180
tcaaagaaga tgagggggtg agctctgcag acatctggga aaagggcatt ccaagcaaag 129240
cgttcagggg atgctgaggc ccccgggcag gagtgtgcct ggtgtgttcc aggggatgct 129300
aaggcccccg ggcaggagtg tgcctggtgt gttccagggg atgctaaggc ccctgggcag 129360
gagtgtgcct ggtgtgttcc aggggatgct aaggcccccg ggcaggagtg tgcctggtgt 129420
gttccagggg atgctaaggc ccccgggcag gagtgtgtct ggtgtgttcc aggggatgct 129480
aaggcccccg ggcaggagtg tgtctggtgt gttccaggca cagcagagag gcccccgagg 129540
ctgcaggggg cagtgggaag aggagcagaa taggacagga ccaggcattg agagcatagg 129600
gaccagatcg cactgggctt tgtcagccct cacagggact tggttggaag tcactgagag 129660
attttaggca gaggacagag gtgatctgaa cttctgtgtt aataggctga cagctggtca 129720
gaatagacgg aagtgagggt gggagaggaa caaaggcggg gaagccagtt agaaggtcat 129780
tgcaatatca ggtgaaggtg actccgacgg ggcagcatca gtggagtgta tgaagcagtc 129840
agattctgaa agcagggtcg agagatgtgt agatggatca gatgtgggct gtgagaggag 129900
agagggggca tggatgactt cagagttttt gtcctgcaca gtagaagaat ggagtcctag 129960
tttcctagat ctggaacatt gcaggggggg aagatgctgg agagaagatc aggagcttgg 130020
atttgggtgg gttaaatcaa agatacttac acaagtccag gcagagatat gtacctggag 130080
gtgagaggga agactgagct agaaatccaa attcggatta ggtatattaa gtatcgtcag 130140
cctttcaagc tgtatgagca atggaaggag atctgtttat ataacagtga ttcacacgtt 130200
tggagcctgt tgcgtgtggg tgctgagcga gctttaggct tgcagtggtg cacagcacgg 130260
aaccgcatgc cctgcacacc tgtgcacctg ccacactgct tcctgcccag ccagatgctg 130320
ccatatcagc tccctgcttg ctgcctgcat ggcactcagc agctctggcc ttggccttag 130380
cactgatggg cttgccatct gcagccttcc ttccttccgg tcctgctgtg ccctgagagc 130440
ctcctgctgc atggtgtatg ataggtgccc aataggtgtt ggcggattaa ttagtccagt 130500
tggaaccctc tgtaaccacc acatgaccag atgctctgtg tgctacagag gacacaggat 130560
tagtggatac aagaaatact tcctgagggt agccccaaat gaagtcttga cacaggtcga 130620
tctccacccc tcagcgtggg tagaaactgg atctttgctt tcagaaggtt gagacgggtg 130680
cagaataaac accttgtggt accttccagc tctgaccttc tagggcctac tggaatttgg 130740
ggggcgggga cacattctcc agtgtcatca cagagagtat gcacattcct gcaagggcgt 130800
ctggagtcag ttcattccat gcaagcttta ccctgtagac aactgccact cctgaatgtg 130860
gtccagaaac agcaagtaca ggcatgcgtc ctgccacagc tgacgcacgg caagccctcc 130920
ctgctgtgtg tggggaggac gggcgccttc ctgtcaccca caggctctgt gcatcctccc 130980
caagcacagt gagagctagc ctgggagcct gggtcccacc agcatctctc cacagtggaa 131040
atccatgtgg ccctcacatg ggacactgca gttgcaactg agtctcccca acctgccctg 131100
ctcacttcat tccagggcca gcctctgagc ttgttgttca gcatggcggc tggatcctcc 131160
cagggtgagg gaagggagtg atggagtgaa gccaaaaggg gtcagagggg ctcaaacaaa 131220
ggccaagcgg ccctttccag gttggcgtat gggcccagtg cttttgaggt tgatccagga 131280
taagccctct tcagcctcca gatgaatggt acctcttccg gctgttcctg aaatgtcaaa 131340
atgggaggtc tgcgtatcct aacagacatg tctccgatgc attttgcaga ggtcctgcca 131400
tgtgccagat gctatgccag tgctcgggca cagagaggct ccaagacaca gttcctgccc 131460
ctgaggagcc cacaggctag ttgggaacat ttcggatttc aggaaccaat agtaccatgc 131520
acaagggccc aagggccacc agtgacccag aggagtgccc caagttcagt ggagcaaaca 131580
gggatttccg gctgaaagaa acaaggaagg gcttgtgagg aagggtctgc ctaaggccag 131640
attctcagga gttccccagt gtcactttgt ttttttttat cttagtagca tagaaaatac 131700
aggccattag gagatggcga ctgccccaag ggtacggctg tccttttgta gaatgaagtg 131760
ccaggcattg cccacatatg acctgcctta ctccgcctac ccccaggggt gagacttctc 131820
agggctggcc ttgctcccca ggccctggga gggaccacag aggggctcag cagtgacgag 131880
ccaggcttcc ccacccgatc cactgggcaa gcgacgggga tgtcaggccg agacagtcct 131940
cagcgatgac ctgccctaac tcccctcctt ccaggggcag gtctgggccc ttccatgagt 132000
gcagagcaga ggtgggagct tcctggccag gccgacataa ggaaagggcc tgctgcctct 132060
gggaggatgc tctggtgccc acagaaggcg tcagtgtgga tgggggcctg cagtggacgg 132120
gcattgaggt gtggaggaga gtctgagaag atctctatca accaccagag agccaggaag 132180
cacccccctag gaggaagggt gaaaatccgt gtctacccag agctcaccaa ggcactggtt 132240
atgctgtgcc caaagacccg ggacccaacg taggcattgt tcgcaataag acctaccccc 132300
agagcatgcc tgtgaggcca cgccaggtgg gcaggacggc cgctggccga ggcttctcat 132360
cagtgcatgg gtggagaggg aagcccagcc tgcctgcacg ctatgacgct attgtgtaca 132420
cagggaggca ggaccagccc cagcactgaa tgttcaggtc aagctgatag tgcctgttgg 132480
ggacctcagc ctgggaaggt gacagagaag acctaggttg ccctctagct ccaggattca 132540
gagctctaga ggccgggaaa atgcagggct ggtcagccag gaaaatgcag gtctggtcag 132600
catcgtcagc atcgagtcag ctgcctgtca gcctcgtcga tgccgaggta tgaactgatc 132660
tcaaatgggc aggatcttcc actccctggt tgtctggtga gggtggcctg tgagtgcaca 132720
gtcaccacca gcctcagtgc caggcacagt gcagcacaca cacacgcgta gaccagaaaa 132780
gcaggcagtc ctcacttctc tacaggcatt ccaagaacct gtgcttgggg cagggtgctt 132840
cgtttctgtg gtgttcattt caatctcctg caaatctctg caagttaatt gctttaaaag 132900
aaaatgaaaa gaaaaaaact gctccaatgg tgttctgtgt aaaagtgctt taaaatctat 132960
gctaagaccc aggatttatg aagtaattaa gtgatctgac tgatgcgcta gctccaataa 133020
tacctcctgt cagattgaac gtggcttagg taattagttt taaagccatt tttaaaggtt 133080
gagtagcaca tcagtcatcc attttcctct tcagttccca ggccaaggat ctgggtcctc 133140
ccaggatcac tctcttccag gaggcaattt aggaatggaa tcgagtgtga atcctgcttt 133200
gcagtcttgc agcatttgca gatactaaca gctcttcatt tattcctgca cacctatatt 133260
atttatttat ttatttattt atttatttat ttatttattt attttgagac agtctcgctc 133320
tgttgcccag gctggagtgc aacggcgcaa tctcggctca ctgcaacctc tgcctcccag 133380
gtttaagcga ttcttctgcc tcagcctccc aagtagctgg gattacaggc atctgccacc 133440

-continued acatctggct aatttttttt tttttttttt ttttttgta gttttagtag agacagggtt 133500
ttgccatgtt ggccgggctg gtcttgaact cctgacctca ggtgatctgc ccacctcggc 133560
ctccgaaagt gctgcaatta cagggtgagc cactgcaccc agcccagcac acctttattg 133620
aactctactt agctccagat ttgggaacac taggaccttg cccctgcagt gcacagtgtg 133680
ggtgtggaag agggggcagc ttccaccgtg ggtgagcttg ctactccagc cgttacgcac 133740
agagcctgca aggctacgaa cggagctggc aacggtgcag gcagagctgg ggcgatggct 133800
cgtcctgcag aacatctgtc ggagaagttt ggctgcattt aagagagttg ccatccaaaa 133860
tgcccgagat tttaagtttg gacccagaat gcagaaagtg tctattctct gagaaacatg 133920
tatgcttcat tctcccacgt cagacatcag acaggcctgg ggttggatcc tcctgcctcc 133980
gcttttcctg tctctctggc ctctgcgctg ggtctcctct cctgtaagat agggctgtgc 134040
agaagtgaga cccagaccaa gtcactgaag agaggagcct tcccagcccg cccttcttgc 134100
ctcggagcct acgttggtgg ttgcacctga acgacaaggc agagcctgtg cacctgccaa 134160
ggtcaggcca gcctccccac ccagggccac atcccgctcg gcaccctcag gtgcaggaag 134220
gtccctgcac ctcctcatga cctggggccc ccatgggcat gccggatgca tgcaaagtgc 134280
tctgcaggaa tcgagcttgg ctttgtcagc actaaggggc atctgcatgg tgttctcctg 134340
ttcatgcagc acacacttac cttgtctgca cacctgcccc atgccgggtc tgctgggtag 134400
gcatgggtgt gaggggtgtt tccttgttct tcacttcttc caccccaaga gcccagctga 134460
gtgtgccctg caggcagttt gaccagggct atgtacaggg cccaaacttt actgagttgg 134520
cctagccctc cctttgtaac caggagccta cctaaggtgc tggggcacct cccacagtct 134580
tcccctgcca gggagaattg tgagacatca atgtctaaat agaaaaaata atcaggcatg 134640
ctttccaatc ttctctctat aattgacacc atgtatctta tttcatggtt ccaaagggtt 134700
ttacgtactt ggtattcaca tagtaataaa tagactgtct gagacaattg atggcacttt 134760
aaaaaatcct gtgtcactct tgaactctga gaattcactt tctccctgat taaaatttct 134820
tttttctctg atctttcatc tgtttccaaa agagcagcaa cccacatgtg ctgtgttttt 134880
ccagattatt tcaacagcat tatttccaga ttcccaccaa tctaggaaag aagtccaatt 134940
tatcaaaaga acgagagagg aataggatga tgattagcac ctacgtgttc tccagcaggc 135000
actgggtgct attttatctc gctgttacaa atcagtatag aatcagggta gatgataata 135060
aggaattaaa gtttcaggaa aagttattct tgctagtgat gcatatcatg gtatttacaa 135120
atgaagacat gaccacgatg cctatgattt gtgctttaaa ctattccaga gggtgggggt 135180
gaggagtggg agagtaggaa gagggtgggc gaaaccagat tgagaaaagg ttggggattc 135240
ttgggactgt gtgatggggc acggggactc attgtactgt tttctccatt ttatgtttat 135300
ttgagaattt ccattacgtg aagagttttt aaaagcacat gtatgggaaa catttcttcc 135360
gaagaggtca gaatgcaaga ctgtctgaga gatttacatg gcacaagtaa atttaacgat 135420
gtaaagattt cattgcttta cagcaaatac acttcagttc ttcacttgtg aggagtaaat 135480
gctcaatgtg ccgtgggaca cgtagagaca gggattttac actttgttta aagtgtaaaa 135540
agacacgtag tttcttttac gtttgactga aggtgctcta gacagttact ggacgtgtgt 135600
atgggagtgt gtgcttgggt gtatatatgt gtgcatgtgt gagggagagt attgtgtata 135660
agtatgtatg tgtgtatgtg ggcttgtatg tatctgtgtg tccatgtgca tgtctatgtg 135720
gatatgtatg tgtgtatatg tgggcattag gtatatgtgt atacttgtac atgtatctgt 135780
gtgtgtgtgc atgtggatat gtgggtgtgt gtatgtgtgt ggtgcatatt ggcttatgct 135840
tccttttcaa gacccagtgt aacacaaggc tgagctctag agcggcctgc ttctcagatc 135900
catcttccac cactggtcat tgcggacctc ggcaggccat ttccatgctc cgagcctcca 135960
acctgtcctc tgcccaggga tggtgggagg attaaacgaa acagtgcccg agaagtgctg 136020
agccttacca gcatgaacat gattctctta ttgtgagtgt ttagattctc cttttgtgga 136080
agagggagct gagtccaagc tcctccaccc agagcctgac tgagctcacc tgcctggaag 136140
gggcagagcc tggtgtcagg gccgtcttcc aagctcaggg ccaccctcac ctcaacccaa 136200
cctggtgagg tctccacgcc tctccaaggc agtacaggca gcccatagtt gatctgatct 136260
ctttagccct gtggccagtg gttttcatgt gtctggcttc aggatatttc tggttggatt 136320
tttttgttta aagtgttgta attagaagat aaaaattaaa tgaaatatta aaagctggga 136380
gcctctgctg ggtgccagcc agggtcgggg tgttgaggaa tgttgctgct gagaggctgc 136440
ctcacttggc tgaaatccaa gagagcagca ggccttctga gaacttgctt tgaccagtcc 136500
acaagagcag gggtccccat cccacctacc ggtccatggt ccatggactg ttagggacta 136560
gactacacag caggaggtga gcggccagca aacacttcat gtgtgtttac agctgctccc 136620
tgtcactccc acttctgcct gaactctacc tcctgtcaca tcggcaaagg cactagattc 136680
tcataggagt gcgaacccca ttgtgaactg cacgtgccag ggatctaggt tgcacgctcc 136740
ttatgagaat ctaatgcctg atgatctgtc actgtctccc atcaccccca gacgggaccg 136800
tctagtcgca gggaaagaag ctcagggctc ccactgattc tacattatga tgagttgtat 136860
agttatttcc ttatgtttta caatgtaata atgatagaaa taaagtacac aatgattgtc 136920
atgtgcttga atcaccccga aaccatcccc actgctcccc accggatccc cagctgtgga 136980
agaattgtct tccaataaac tgattccttg tgccaaaaag gttgggaacc actgcagtag 137040
aacatttgaa atgcaatagg tacttggaat agatgcttgg ttttaagggt ttttcctata 137100
gactatgttc ctgaatggga ggattcagta tcactgagat atctcttctt cacaaagaag 137160
ggttagccgt cactttaaca cagtcctcat caacatcgca acaaaattaa aggaatgcaa 137220
ggaaaaccta ttctgaaaga atgggcacag ataatagcta gagaaattct gaaaaaatga 137280
atgcaggtgt ttaactgtgt tttttaacta taataaaatg atctggcact ggtgctggaa 137340
tagaccgatc aagggaacag tacggatagt ccgttaataa agccacagag atatgctaag 137400
gatagcgttt taaactggtg ggaaaagact gaagtgttga ataagagtta ttgataattg 137460
gccaaccatt tggaaagaaa ataattatct tgatgcatac acataaaatt agaaatttct 137520
gtctggcaga aaacatcata aaattagaaa aatattcctg taatctcagc actttgggag 137580
gccaaggcag gtggatcacg aggtcaggag atccaagacc atcctggcta acacggtgaa 137640
accccgtctc tactaaaaat acaaaaaatt agccgggcgc agtggcggcc acctgtagtc 137700
ccagctactc aggaggctga ggcaggagaa tggcatgaac ccgggaggca gagcttgcag 137760
tgagctgaga ttgcaccact gcactccagc ctgggcgaca gagtgagacc ccgtctgtaa 137820
aaaaaaaaaa aaaaaaaaaa aaaaattaga aaaatattta taaaatattt tggacaaact 137880
caagtgattc acagatggcc ttttcacttc tgtctagccc atgggttgga aaactttttc 137940
tgtaaagggt cagatagtaa atgtttgagg ttttctggtc tctgagacaa ctactcaact 138000
ctcccattat agtgtaaaac agccatggaa attatgtaaa tgagaggccg tgctgtgttc 138060
tgacctcact ttataaaata ggcggtaggt cctggcctta gtttgctgtc cccactctgc 138120
cctgtttaca tgttcagttg aattgagtct tctgtttcat ggtagttaag agggctgttt 138180
atttggctgt tatatgaggc atcccatcct gtccccattt tcccaccacc catgaagtta 138240
tattgtcctg cttgctggta aatatttaac aactagtgct ctgggggaaa ttatttatag 138300
atattgacat atcacataag ttcattataa attttactga tataaaggat gttagccaac 138360
aatttacaaa taataaaata tacattgctt gtattataaa ttccatttag ccagttgatt 138420
ctcagagact gctttcattg atttttgccg aattctggtt ccataaccag ccgatggctg 138480
ccatgcatga acagttgtct ttccagcgta aatattgggt aatatttttg ccacagaaac 138540
aacaaagaca tatgtcagaa cttcattcac tcaccaggga tgggaacaac ttccttgcta 138600
aattggaaaa taattttcaa atactgaaag aatatctctt cagttttgta agctgttcac 138660
agtgtaatac ctacagacat gaaacatttt taagttatac ctgcagtatt aatgctttct 138720
ccatcacttt cttaagccca gaaaatcaac agtaaaccca gcccttgttt gtagcatttg 138780
tcgatttcca tatgggaata tcccgccatg gccaatttca agcttttcac gtgacgtcac 138840
tgaagacggg ttggtaaaag aggggtccag tagccaccat gagatagtgc ttcccctgtg 138900
tagatagaac agatgtgagt aaccctgaag cacagataat gacaaaatat agtgagatca 138960
tgaggaaggg gcaatttgtg aatattcatt acctttgttt ttagtataat ttattcaatt 139020
gtaagcttct ataatttaat gtttaataaa gactgtgttt aacaaccagc tcacaaaggt 139080
tctgaaaatg ttcacaatca gttccgttaa gccagtgctg gtcggctgca gcgcaccact 139140
gcatattggg aattgaacgg gtagagggtt gtctttctct tgggacaagc acactttaag 139200
gggagcgtat tcattgcagg accaaggctc aacgtgcact gctccccacc cgtcccagct 139260
cctctttatg cttgcggggg ccagccactc tccagtcctc cccaggaata tacgtcgcaa 139320
ccaggcattc ttttttcatt ggcctcattc ttcccagggc cggctcagag gcccccggt 139380
ctaattgcca ttggtttaac tgctgtttaa taaatcaaac tatttttctg actaaatctt 139440
gctaatcagt aaatagtgat catctgaatt ctccatatgc taaaaagtca tttttccaag 139500
gggtaaaatt aaagtaatat ttggcataaa aaaattctaa tacacaggca gacaccttta 139560
tgtctaatat ctcaactgta gaggttagat aatcacagag tgctatactg tgttatagcc 139620
ttaaaatgta gagtgcttac agatcactaa gaaatattta aataatatca ctaaataggc 139680
caaaatcctg aaaagcaatt cgtaaagaaa acatacaaat aaccagtaaa cacaagatag 139740
tcaacatttg tagtatccaa ataaaatata aactaaaggc caggtgcgtt gtctcacgcc 139800
tataatccca gcactttgag aggccaaggc aggtggatca cgaggtcagg agttggagac 139860
cagtctggcc aacgtggtga aaccctatct ctataaaaat acaaaaatta gccgggcatg 139920
gtggcgtgca cctgtagtct cagctactcg ggaggctgag gcaggagaat tgcttgaacc 139980
agggaggtgg aggttgcagt gagccgagat tgtgccactg cactccagcc tgggcaacag 140040
agactccgtc tcagaaaaaa taaaaataaa aaaaataaac gaaaacacaa gaaggcaaaa 140100
tcatgataga aagccaacaa gcagcagttg cagagatggt agaacaaatg tgtgaaacga 140160
atctgtatgg cactctgcac tcggggccac agagtgatgt gatttaaaga acgggaatgc 140220
aggggcagag gagcctgggt cccacgctgg ctgcaccggt gacgggctgg gagacctggg 140280
actgatgact ccctcatcag cgtcttacca gcacctggtg gacatgaaat ttctcacgca 140340
gcctgtgtag gttgtcacag aagcccaggc tcctctcccc tctccctacc tgccactgca 140400
agtgtgtgtt ttaccacagc ctttaggaat tggtccattt gctctctggg aaaattccag 140460
cctggagaag ctggtagaga cctgcctcca tgcctctgag gaaaatcaaa ttggctgcga 140520
cctctacaga acccaggaat ttggaattca ctgaatccag ggttgctgcg ctggaggcaa 140580

```
agctgggctg ctattgggtt ggctggccct aagggaaaac tcttctgact tttgaactca   140640

gcaggtacat ttctattctt cctttcttct tcttaagcaa cacttttccc gagaaaaaca   140700

aacaaaactt tgctaaccaa aagctttgtg ttgaaactgc caggaggaga tgataagcca   140760

agcattgcct tggctcctca ggacttttgc aggcccccgg ggcagagcca ttcaggaagt   140820

tcccacaggg cttggctttc tttggagctc agcccagtgc acctgactct accctgtgct   140880

tctgtggaat cccagctttg gttctgtcct tcccagaaac ctgaaagttg aagccaagac   140940

aggatcaagg aaggtctagt cagaactgtg gtgcttttgc caaaacttgc agaataagct   141000

atcggggcac agatcagtta cgaaaaccaa atctgacccg ttatccaggc gacttgagtg   141060

agaggagcag gagggtggcg ggaggagacc aggctgccgc agacactgga gctcctgaac   141120

gggatttgga cctcagggtg gtgtttaggg agagcccaga gcagagcagc tggcaggcgt   141180

ggtctgagtt cagctggccg cttcctggcc tggtcacgga atctctcagt ctctgtttct   141240

gcacgtgtgt gatgggaata atagtgtcta cttcaacggg cctggggaga ttcaaatgga   141300

ggaaggtttc atatgaacaa atcctttatg aggagtttca aaggtttcag gattacaatc   141360

tttgtccata gtgcctataa catcagaaac accaagaagt gtttcttgat attgagcttc   141420

cttgaagcca attacacatg tcagttacat atcgaattct gtgttctgcc ttgtgctgtg   141480

acggtgtctc acgaaggtgc tgctatacct ttggaagact ccagaaagcc cagggaagca   141540

ggttcttttc aaacatgata gttcacactt catacctcga agcatgtatt ttgatgacgt   141600

tttactccgc aaatgtcaca ctggccccac tgcgtgtctc cccagactgg cccagccctg   141660

ctgtcgtcag gccttgcctg ttgcccagta aagagatcta gccctcactt ccttgcctcg   141720

gctcccccag cctcccccac ggtgaagcct gggcgttgga atggctgctg acgttcccac   141780

cggggaggag cagcggaggc gcaggggccg gtccgaccca gcgggacccc gggggggcgg   141840

gggttgtggc ttttccctcc acttccaggt gaggcttggt atcaggcctc cccagcatct   141900

ggctgcctgg aggggcagg taacacaacc cagaaggaag gtttacccaa ggaaagacag   141960

gacataaagt gtatgccctt cctgtctgag ggcacattgg tctcacaagg cctgtttgga   142020

agacttcccc cagctaagca accacccccgt ttctttgtgg agctgcagcc agcttgaaac   142080

acagctcctt ccatttgtca accccgggcg cttcctcctg ctgccctcca ctcctgttgc   142140

cctgggattg cacctcccaa taaagcttca gcccatgggc ttcacttcag tcccttgttt   142200

tccagggaac ctggactaaa acacgtgttc cggtggcaga ttgaacaaga gctttggtaa   142260

tctctgtgaa atactgcaga gggacagatg accaaagcca ccacatttag aactttggct   142320

gcctttggaa gtccagagct ggatctctca gctcccgccc ccagaggctc agcactttgg   142380

acatggctca caaacagttg ttgattgact gcatgaatgc gtgtgcgtgc aagcatgaac   142440

cttgtttaaa tcaagagctt acataatttt aaccagttct gtcttcagct gtacatactc   142500

agtaaaatgt ttaatgaagg ggaagagatt agtctcttct gtgtgaccat gttttccctt   142560

tattcatcct aaaaagttcc atgaattctt gatttccttt cagtggccct ttcaacaatg   142620

tcttttttcc caagagcata actgttctca ttttattgct agccatcttg atctgtgttt   142680

tattgacatc tcttttgagc taatcttcat ttctaagata agagttgaga ttttgcaatc   142740

tgtgttcgat ggctcaatct atcctgtgct tgatgctaga aaggaagaca gatttaaagc   142800

acatgccttc tgtgccggct ttcaagtttg tcactaaact ctcatttctg gaaagtgcaa   142860

ttatagagta tcactcccac ttccttggaa acagagctga agaacttggc acactctcca   142920
```

-continued aacagtcacc atacacactg ttgtcaaaaa gttccatttt taaccccatt tgcattaata 142980
ttgcagtcaa tctctttacc tccttttctc tttcacgggg ccgtgacagt gacgcctttc 143040
cccaaaactc tcctcgtttg agaaaaaaag aagtatgtat ccccacttat ctcggggaga 143100
aatgcaacca actgctgctg tgcacattta tgaatcacag tattgtttag tcggttctgt 143160
atctccagta gaaagcataa caaaaagatg acctttgtct cacctcatag ctaatttttg 143220
caaataaaat actaaacatt gatgaaaatg aaaatgacag atctgaggaa gagggagagc 143280
tctcttgaaa cccctttccc agatttgccc tcagttttag gaatgaggta cgcttgggca 143340
ttcctgttgc ctgcatggtt cggcattctg gcagccaggt tcgccccaga atagataagt 143400
gtgtttgatt ttcgaacatt tgactttatt acctatttcc agaaacactt cgtgttcaaa 143460
ctacgtctct acaggcattt ctacttggtc tttttctccc ctgacatttc acagagtcct 143520
aactgtgctg catgtataac ttgttctttc tttttgttac ttgcatagca agcatgtttc 143580
tatgtcatta aatatccttt gtaagcagca ttttatagat ttttataata cttcaccaac 143640
agaagcacca taatttattt aagcatctct ctattgttgg acatgtagat tgctttccat 143700
tttttcctat tatgagcgga cagcttagta caaaaagcct tctcctgaat ttaaaattat 143760
ttctttggga ttattcacca gaagtaaaat tactgggata aataagaggt ggaaaccaca 143820
aatatgcctg cctttgatac atattgccaa tttgcttttc gaaatagttg aactgatttg 143880
tagtcttacc aggagtgggc agttctggag gaggtagatg atacccttcc ttaacttaca 143940
ttgtgatcat tactaacaaa ggtgaacctt ttttcaaatg tttgtgcact gtgttttttc 144000
ttttgaaaat tgccctttct ggcgtggtgg ctcacgcttg taatcccagc actttgggag 144060
gccgaggcag gcggatcacc tgaggtcagg agtttgagac cagcctggcc aacagggtga 144120
aaccccgcct ctaccaaaaa tacaaaaatt agccggtcat ggtggtgggt gcctataatc 144180
ccagctactc aggaggctga ggcaggagaa tcacttgaac ccgggaggcg gaggttgcag 144240
tgagccgaga ttttgccacc tcactccagc ctggatgaca gaacgagact ccgtctcaaa 144300
aaaaagaaaa aagaaaattc ccttttgtct ttcgcgagag cgctcagtgt tgctatcaag 144360
ctgataagta tgtagtctgt gtaaaatatt ggtaaaatat tggtgtaata accctgtgtg 144420
tgtcgtaatt catataaatt ttttttctgg cctgctgttt cacttttgac tttttaaaaa 144480
taattttaaa tttcccctcc agagttttga taattatttc cttttttaaa aaagtcccaa 144540
tttgtttgat tttattttct tcataatctg tttgcctttt tttcagtcta aatattagtg 144600
tctctaaaaa ataaataaaa gatatataaa actttttcta agttgctaac aaattactcc 144660
aaaacaaagt caagatcaaa atgttaaaag atgtcgtgga cttttatttc caacaacaga 144720
gaagacaagt gtcttgaaat ctccctccca cagaaaagaa ttttaaatgt tggttgaaat 144780
gttcacagcc aaagaggtga acagaatcat ggtccggctt ttgcttgaag gcatctgctt 144840
catctgtgga gcccacctag cagaccacat aacactggga cctcaggggc acccaaggaa 144900
aggagacaca gacaaagctg tgtaactaga acccacaaaa caagtgctta caaacaagtc 144960
caataacttc agtagtttca ctaaaggcat acagactcgt tgctcccctt gagagacaaa 145020
aattgtcata ttggattttt ttaaaaaatg tatttaaaaa tgtatttggg aggctgaggt 145080
gggcggatca cttgaagtca ggcattcaag agcagcctgg cctacatggt gaaacctcgt 145140
ctctactaaa aatacaaaaa ttagccgcat gtggtggtgt gtgcctaata gtagtcccag 145200
ctactcaaga ggctgaggca ggaggatcac tggaacctag aaggcagagg ttggaatgag 145260
ccaagttcat gccagtgccc tccagcctgg gcgacagtga gactccatct caaaaaatac 145320
aaattaaaaa aaagtatttt ctgtagtgcc aggtatattt catttaccca ccagatccat 145380
tctccactcc tccaccccac agactccctt gcctgtggct tatagttgag ttcagccaag 145440
gggaaactcc agcaggagag gagggaggga ggagatattt atttatgagt tagtgattct 145500
ccagtccttc atcagccaaa cagaaatgtt atggcaaaaa gcgttattgg agcttcatat 145560
gtagctctgt gtatgtatca atatgtagag ggtctataca tattggtaaa aggtttagtt 145620
cagttctaaa agttccacct ctaatctttt atgcaattta taacacagcc ttaaaataca 145680
tatagagcaa aaacttgtta aaactacaaa gagaaaatga caaactcaca caggagggag 145740
agatttagca tacctcggat atatttgata gataaaacag caaaaattca taataataga 145800
agatgcaaat atctcaattg acaatttagg tcaaatggac atattggaac actgtgccaa 145860
acaacagaat aatacaccaa atttttttatt tatttatttt ttttttgag acagaatctt 145920 gttctgtcgc acaggctgga gtgcagtgac gcaatctcgg ctcactgcaa cctccgcctc 145980
ccacatacaa gtgattctcc tgcctcagcc tcctgagtag ctgggactac aggtgtgtgc 146040
ctatattttg tatttttagt agagacaggg tttcaccgtg ttggccaggc tggtctcgaa 146100
ctcctgatcc gtgatctgcc cgccttggcc tcccaaagtg ctgggattac aggcatgagc 146160
caccgcgccc ggccaataca cccacttttc aaacacgaat ggaagattta tgaaaattgg 146220
ccacatgtcg agccatttgg caagcttcga tggatttcca aggattggta gcatataaac 146280
cctattctct gacattacac ttaagttaga aatcaaaatc aaaaagataa ttagaaagtt 146340
tccatacatt tgaaaattga aaaatacttc taaataattt atgtgttaaa agaaaaaaac 146400
ataatttata ttagaaaata cttaaaactg gatgataata aaaatactac atattcaaat 146460
aaggaagata cagctaaagc tgtagttaga caactttatg gctgtaattg catatatcag 146520
aaaagagaaa atcctgaaaa ttaatgtgct aagcatccaa cttaagatga tagaaaaaaa 146580
ccaacaacat aaagaatgaa gaaagaagga atttttaaaa tagcagaaat taacaaaata 146640
gaaaacaaac atatgtagag aaaattaaaa tgccataagc tggttcttga aagaaactaa 146700
taaaattgat aaacttgtaa gtagaccaag gaaaaagctg aaactatatg atttcaggaa 146760
agaaaaacgc atgattatag atcctatata cattaaaatt atgtgacaaa ggaattctaa 146820
gtgaaatgaa caaattccaa gaaaaaatac aacttaacaa aattgacacg tttacataaa 146880
attaaaattg tcctattaaa gaaattgatt ctataattta aaagaaaact caaggccaga 146940
gcaatttacc agcaaattct gccaaacatt taaatggaag aaataatgtc agtgttctgt 147000
aaattcttct agatagtaga aaaataggga aacagtcccc actttgttga atgaagccag 147060
agtttggttt tttttttttt tgagacggag tctcactctg ttgcccaggc tggagtgcag 147120
tggtgcaatc tcagcccact gtaacttctg cctcccagat tcaaacgatt ctcctgcctt 147180
agtctcccaa gtagctggga ttacaggcat gcgccaccac acccagctaa tttgtgtact 147240
tttagcagag acagggtttt gccatgttgg ccaggctggt ctccaactcc caacctcaga 147300
tgatccaccc gcctcagcct cccaaagtgc tgggattaca ggcgtgagcc accgtgccca 147360
gctgaagcca gtgtattctt gataccaaat cccaagagca catatgagaa tggagaattt 147420
tcagccaatc tcactcaaga acataaatac aaaaattcta agcccaatat caagaaaact 147480
aaatccaaca gtattaaaaa gatgaaatac tctgttcctc ttttcctgcc ttgttttaga 147540
ttaatcaaat atttgtcagc attccacttt atctcctcta ttggcttttt agctgtactt 147600
tgagtggtgc tctagggatt acaatatgca tccttaattt attacacttt acttagaatt 147660
aatattgaac agctttacac ttctcagata aaaggatcta ataacagtgt aattccatcc 147720
ccctccactt cctcatttgt gctgtaatgg tgttgtatat tttacttctg tatttgttac 147780
aaactccttc ttaaaacagt gatattactt tttgctttaa gcaatcttct tttttttttt 147840
tttttttttt tttgagacag ggtcttactc tgtttcccag gctggagtac agtggcacaa 147900
tgtcagctca ctgcaacctc cacctcccag gttcaagcaa ttctcctgct tcagcctccc 147960
aagtagctgg gattacaggc atgcaccacc gcgcccggct aatttttgta ttttcagtag 148020
agacaggttt tcgccatgtt ggccggactg gtcttgaact cctgacctca agtgacccat 148080
acaccttggc ctcccaaaat gctgggatta taagggtgtt gtcttttaaa taaattaagg 148140
gaaacagcta ctcttcagtg tgtttactga catgcttacc atttctagtg ctctttattc 148200
tttcctgtag atctgaattt tcatctgcta tcatttccct tagcctgaaa cacatccttt 148260
accatttctt atcaaactgg gcttctggca aggactttgc tcagctttgt tttctttgaa 148320
aatgtcttta cttcaaccca tttttgaatg gtattttcac tggatataga attctgggtt 148380
gggagtattt attccagcac tttaaaaata ccaaattttt aggccgggca tggggactca 148440
tgcctgtaat cccagcactt tgggaggcca aggtggccag atcacctgag gtgaggagtt 148500
caagaccagt gtggccaaca tggtaaaacc tcatctctac taaaaataca aaaattagcc 148560
aggcgtggtg gcaggcgcct gtaatcccaa ctactaatcc taactacttg ggaggctgag 148620
gcaggaggat cacttgaatc caggaggcag aggttgcagt gagccgagat tgcaccactg 148680
cactccagcc tggataacag agcaagactt tgtcaagaaa aaaaaaaaaa aaaaccccac 148740
acttttggcc aggcgcggtg cggctcacac ctgtaatcct agcactttgg gaggctgaga 148800
caggtggatc acctgaggtt cggagttcaa gaccagcctg gccaacatgg tgaaaccctg 148860
tctctactaa aaatacaaaa tttagctggg tgtggtggtg gcatctgtaa tcccagctac 148920
tcgggaggct gaggcaggag aatcgcttga tcctgggagg cggaggttgc agtgagctga 148980
gattgcacca ctacactcca gcctgggtga ctctgtctca aaaaaaaaaa aaaaaaattt 149040
gggagaagca cataaatgcc ttaaaattaa aaatataagt caaaaattca aaattcaata 149100
gatatgttag aagataaact tgaggaaatc tcccagaaaa tgaaagggtg gtgggggaaa 149160
gacaataaat attggaccca gtaagaaatt ttgttagaac attgggaggt gggggcggga 149220
gagggatcat gtgagtatgt ggaagatagt gtaagagaac tgaattctca gcttcctagg 149280
tgagacatca ctggacaatg tctaacatca agaaaccagg acatagcata tgagtatttt 149340
tgtctagcaa tgtaagggca aatgccagaa aaataactca aagtgttaaa aagaggtggg 149400
gagtcagggg gactccaaga ggtagaatgg agtgaaggag gactgctttc tttgttataa 149460
accttgtaag agtttttgac tttccagaca tttaatttat tactttggaa aagctggagc 149520
atcttaaaag atagaatgac cttatagatg ccattaagaa aagtgctgtg ttgtccattg 149580
tacacacagg tgatcattct ttcccgaaag gatatttgtt taggattctt cgatcctttt 149640
cctggcattt aaaataccat ctttcagggt ttttgtggct ataggagcac agggaagcct 149700
tgtatctccc ctttcttagc ctgggtctga gagttcatgt gtgtatgtgt gtgtgctcag 149760
gtaagtacgt gagtgtgggt gtgcatgtta tgggtgcctt gtgcacacat gtccatgtgc 149820
atccatggac gtgtgtgtac atggggagca cacatatatg tactcttttt cttatcctcc 149880
tttccaagcc attcctaaat tcctttttac ctttctctta cttgccataa tgtgaactta 149940
aagtgtattt taataatgtg tttattgagt aaaggttgat atttctgttt gtgtgtgtat 150000
acatatacat acaatataca caaaaaatta ctgtgtgtat gtgtaatttt atatatatat 150060
atatatatat attgagaaag ggtcttgctc tgtcacccag gctggaatgt agtgtgcaat 150120
cacggctcac tgcagcctcc aactcttggg ctctagcaat cctcccaact cagcctcctg 150180
aatggatagg actacaagga cacaccacca cgcctggcta atttttctat tttatttttt 150240
gtagaaacgg agtctcacta tgttgccagg ctggtctcga actcctggcc tcaagagatc 150300
ctcccacatc agcctcccaa agctctgcga tcacaagcgt gagctactgt gcctggcccc 150360
tacacggtat ttttaataat agctttattg agatataatt cacatactgt gaaattcacc 150420
ccttttaagg agtaaattat aggagtattc agtatgtgaa ttataggggt gtttttgtat 150480
atttttataa atggatggaa gtaagctttt ttattccttc cgcccaaacc tctgcattaa 150540
cctttgtaac ttgaacatag ccatgggtgg ctggttcacc aaatctcaga aggaagaaac 150600
ttccactggt gttttaaact gaaacatatt tacgtgattt ttctagggct ctcttacttc 150660
actgtgtttc aattaaggaa tttcttcctg catattttaa gtatggggac atagggggag 150720
aattaattaa actctatatt gttaataact tctcctatag ccaggaaaac ccaggaatcc 150780
aaaagtatta gctcagagtc cttaatctaa tagaactttc ccccacccct acttgctttg 150840
tctccaattg taaatttcct tcacaaggat tttaatgctt aactcaaaat gccaggcata 150900
ggaaagcttc attattgctg gtactttcct gttggcaaat tcaaccatag tctcccctta 150960
attctggttc tttctttgca taatgggaat aatcctgttt gttcattatg aatttaattc 151020
attgagggga aatactgcat tgaagatagt gaatgatgat aaatccattt actggcagcc 151080
tcagttggca ctagctgtgg attatcctct gcctctcaca atgacattcc ctggccttca 151140
ttgttgacat ctggaggcag cctgctggca gtgctggccc aagtgtttaa acaggtggat 151200
ttgtgattct tctacaggct caggaatctg atggcaaaaa atttgattgg gcatctttta 151260
agaccccctc cttttagaaa ctaaggaact catggtgcta gttgggtatg tacaacagta 151320
aacttgaaca ggcttgtaga gtatcttgaa tagtaaataa cacattcttg ctaagtggtt 151380
tgccgaaagc agggtcaaca ttctaaaatc tgactgcctc tgggtggcag ttctgttgag 151440
tgtagaccct ggtctggcct gggttgtccc tggacacatc tgcctgttct tcctccttgc 151500
ttctcctgca cccatgtggc ttaccttccc aaagagaatg tggcctcttg gggtgactg 151560
agtgtggagg ggccggcctg gggagcctgt cctggcacaa gtgctgctgc tgtggggggc 151620
cgacactgtg gacgcaatga gaggaggtgg atgcctcctg aaaactaaag cctccaagaa 151680
gctcattcct gtgtgtctct gccttagtct gttatcctaa gtcacccata agcatctgac 151740
tctcctgcct cagttaagct tgggctgtgg tttggagaag ggactgtgta gagggggtga 151800
ttcttatcaa gtaactgatt tgcccaggtg gcctgtggtc cctcgcctgg gtattttgca 151860
gtcaagcctc atgggacacc aaacactgtg gcgggatcat gtggcattgc cgttcatgat 151920
agacataagt ttacagttca agataagaca ttaacgtgtt gtatcacctg acccagtggt 151980
tccactttcg ggactctatt gggaaaaagt aatccagact gcatcaagta atatttctgt 152040
cagatttatg tatttcaaaa aagggaactg gactaaacgt tctgtcataa cctatcataa 152100
gaggttgtta aacaaatggt cacgttcaca gggtgaagta ttttgctgta aaaaaaaatg 152160
ttttaacaga ttcattcatt cagcaaacat ttattgagta cctactgtgt gcccaaaagt 152220
tgctacacac tgaagctaat gcaccaaaca agagagacat gttccctgcc cccgtgatgc 152280
ctctaggctg aaggaagaga aaacagtgaa caagaaaata aataacgtcg aatgcgatta 152340
acatgatata atgctaagtg gaaaaagaaa gagaaaacag ggtgctgtgt gttttcaact 152400
atgcaagaaa tacacatgca taggaaagag cccaggagga aatatgccaa aagagttata 152460
ggtgatttat ttttattttt ctttaaatat ctcaacattt aataattttt attctaacta 152520
gggaaaaagt aattttaaaa aagaatcact cttcaaattt atgccataca ctttatgcca 152580
taggtatgga attctcattt ttacgtcttc caaaggcagg aaaaccaaag tgactccctt 152640
ggttgagaaa gtgaaaaaag catttaagta ctagaaaggg gagataggcc aggtgcagtg 152700
gctcatgcct gtaatcccag cactttggga ggcacgcgga tcacaaggtc aagagaccaa 152760
gaccatcctg gcaaacattc tgaaacccca tctctactaa aaatacaaaa attagccggg 152820
catggtggcg ggcgcctgta gtcccagcta ctcaggaggc tgaggcagga gaatggcgtg 152880
aacccaggag gcggagcttg cagtgagctg agatggtgcc actgcactcc agccgggcaa 152940
cagagcgaga caccatctaa aaaaaaaaaa agagagagag agataaatgt ctcccagatt 153000
accattgtct aaacctaacc ttaggtcaag tgtcacaaat cgcacctatt agaaaaggaa 153060
aggtctcttt tggaggcaca tgcaggaagg ggttgctttg gtcccactgc ttcttccctg 153120
ctggcgtttt tggagctccc agctctcagc tccgcaggtt gttagctcag tcagtgcctg 153180
gcccctcata ggctgtcatg agtatcttgc agatcgagag aaagaacaaa aatacaaacc 153240
atgtgtgagc aaaacaccat ttcattccac tggcccttgt tacaaatgca gctaagatct 153300
gcttctatgc atcttagacg tctcatccct tgttcctagc aaatatcttt ggtaaattta 153360
caagtttata aattgctttt aattttatca aatcagaaat ttgtcttgct cttaattata 153420
tgaaaaggat gctccgtttc tcatataatg agagaaatgc gacgttaacc tttctgagtt 153480
atcggattgg caatgtaagc catagctgca ggctgcaagg gagcccgttc cttttgacgt 153540
gtgacatgtg acgtgtgacg agttttacgt ctagtaatgt agcctacagg tacacatgca 153600
cacagctgaa atgacgtgtg cagtaggttt cccttaatgg acagctcctg cgtgccagtc 153660
tctattctaa gtgctttacc atcatgaagt catttaatct ccaaagcaac cctgtgaggt 153720
agacattcgg agacgttatt attatcccca cgttacaaat gaggaaacta aggaacagag 153780
atgaagtaat ttgctagcag gggcaaagcc aggttccaga ccctgttgtt ccagggccct 153840
tgctctgctc acctcaagta gttgctccct atgtgaccaa ggatagagca ctatttgtgt 153900
agtcgtgtgc tgcaaaatga catttccatc agtagcagac cccatattca atagtcattg 153960
cataagattc taatgtcgta ttttgactgt acccttttta tgtttaggtg tgtttaggta 154020
cacaaacact tatcattgtg ttacagttgc ctacagtatt ccatacagca ccatcctgca 154080
caggtttgtg gcctgggagc cgcaggctgt accctatagc ctaggtgtgg agtaggggta 154140
ccatctaggt ttgtgtaagc acactctatg gtattcacaa aacaacaaaa tcacctgcat 154200
ttctcaggag gtatccccat agttaagcta cacatgacta taattgccaa agtttataaa 154260
caacctaaac gtccatgagt aggggattgt ttaagtaaac aacactacat ctctcctgtg 154320
cagccatgga aggatcataa ggatacactg ttaatggaaa actcaaggtg cagaaagtgc 154380
tagcaggtgt gttaccaaaa aggatgggga aacatatgtt catatttgct tgaataagaa 154440
taaaatgctt cagaaatgat acacaagaaa cggggaacca acattgccca tggggaggga 154500
gacttcgtca tatgcacttt tatacttttg catttctgag ccatccttgt atattactta 154560
ttcagagaca aaaatcaaaa ccccgagtac tactgctttt taatggggtt ttttgaccat 154620
acaaccactt tattcataga ttttaaacat taaactttta aaaagtttta atgtttatat 154680
atgaacaggt aacatatgtt gtggttttaa caaaaagtca aacaggctgg gcgcgtggct 154740
cacaccagta aatcctacac tttgggaggc caacgtggga ggatcgcttg agctcaggag 154800
tttgagacca gcctgagaaa catagtgaaa ctctatctct accaaaaata caaaaagtag 154860
ccgggcgtgg tggtgcacac ctgtagtcct agccacttgg gatgctgagg tgggaggatg 154920
gcttgagcct gggaagttgg ggctgcagtg agccatgatc gtaccactgt actccagcct 154980
aggcaacaga gtgagaccct gtctaaatac acacatacac acatacacac acacacacat 155040
aaagtcaaac agagagtgta ataataatga agtctctctt ccattccagt ccagcctcct 155100
cccatgaggc tgcctgtctg ctgggtccct gggaattctt cctgctctct ttttccacac 155160
agtgcacacc actgaccctg agtgtggagc agcccctctt gtttgtccca ccaaaactat 155220
atctgaaaat aaaaatccag ttttggtgac caggcctttt gtgggtgttt ttggagacat 155280
cctctataat tgaaataaac ttcaactcaa atgatagcct ctagagccct tggtccctgt 155340
cctaccatca tcacaacccc agccaatctc agtgcaccac ttggtggtta aagtgctcgg 155400
attcctttgt ggtcggaatg tggctgtaac tggaccctaa ggagctgagg agagtcagag 155460
gttcctcacc aggcttgttt tctgcacctg cagtggtgag aacaacttcc tgtgtcactg 155520
ctgcagcggt gagaacaact tcctgtgtca ctgctgcagc ggtgagaaca acttcctgtg 155580
tcactgctgc agcggtgaga acaacttcct gtgtcactgc tgcagcggtg agaacaactt 155640
cctgtgtcac tgctgcagcg gtgagaacaa cttcctgtgt cactgctgca gcggtgagaa 155700
caacttcctg tgtcactgct gcagcggtga gaacaacttc ctgtgtcact gctgcagcgg 155760
tgagaacaac ttcctgtgtc actgctgcag cggtgagaac aacttcctgt gtcgctgtca 155820
ccacacacgt aggctgggtt aggaactgtg tcagggaggg ggagctgctg tggggcttaa 155880
tgaaccgagc cctgtggaag accgtgtgct agaaatgcta tgctggggat gctgtttcat 155940
gtaggagggc cttgcttacc tcttccggcc ctgtccaggc taagggaggc ttgggcagta 156000
cagaatctga cttgggacag tgtgcaggct ccagcctttt gcaacctagt acttagccag 156060
ttgaggctgt ggttaaaatg aaacagggct gccacatgcc acattgtgta aatgggtcag 156120
tgtcgaatgc catttcgaat cgcaccagtg gggccagtcc cgcctgtctt tcacctgccc 156180
gcccacccac ccaggatggt gtggattaca gcctatgggc ttatggtatg aggatgagca 156240
ggagctcctg ttctggaatt tagaaacgct aagagatttc cagaattgga acaaaaagta 156300
aagttgtact ggcagagggg cctgcattgc agaaacagtg cataggcagg tatgtaaaga 156360
cagacaggct gccatttaga gccagcgggt ggagtagcga gcatgggcag aggtaagtgt 156420
tgagaaaaca cagtcaacag caaagaatca gagcagtatt cttcctcccc gaaaccattc 156480
tgattgccaa gaaaccccat ggcaggaaag gaagaggaag cagggatttt tcagccaaca 156540
gagacattga gccagcaatg gccctgtccc cagcttgggt cgcaggagac agtcatgagg 156600
gcccactgag gggttcaca gctgaacatg tgtgtgcatg tgtttcctat tgagccaatc 156660
caattagaaa caaacattga aaggctgggg cgtccgggag ccccgtcagc atgagcagct 156720
gtccttgggc aggtcacact ggcccctggc cccctcaact atgtggggtg atgaccttct 156780
aaacagtaac cctgctctga attctgggga tgccgtggtt aaaaaaaaga agaagaagaa 156840
gcttaaacca gtggccagca gcagagtcgg cctgcagata ggcgttaatt aattgcatag 156900
atgctctttg acttacaaat tgcaagttga cttatttcga tgatattttc aacttatggt 156960
ggattcatcc caacatagcc ccatcattaa gtctaggagt gtactgaatg catctggctt 157020
ccacaccatt gtaaagtcaa aaaattgtaa gtcaaactgt cataaattgg ggactgttta 157080
taatgtgttt tataacatca ggaattcacc tggaaattgc taccaggatt ttcactttgc 157140

-continued ttgatacctg agaacagaca gctgcatggg ccatcgctcc ctgtggagct gtcggtgggg 157200
cgggacccca gctgccccca tgttggctgg gagctctccc atcagcactg tctttcctgt 157260
gtctgtctgt ctctgatgtc ccccatggag cctggtgtct gtctactcat ccccctgctt 157320
tcaaagatgt tcttcctcca cccagcttct gcagacattt gggtttttac cagcactgct 157380
atcccccaga acatccctca ctgtcctggg ctagctgtgg aggagagagc ccaagactga 157440
gtcttcccat gatctaggat caaggatcca aacagcagga ctcctccatg caacccagtt 157500
atcacacttg gatgctgtag ggcaagactc acagccaggc ctggcaccag atttacccac 157560
cggatatccc aagacgggaa ggtggctgct gctaggcatc ggggaggcag catcgaggga 157620
ggctgcagtg agatcagcag ggcagaggac agcctccagg acagtggaga gtccagcccg 157680
gctgacctcc atcccagcag ggacaggaag cggagggcag ctcgatagaa caggaataaa 157740
agggcactgg cttgcaggaa tgagacactg gggaaagca gcatgtggcc tgggcaatag 157800
gtgcacagct ggccagcagg taaccaggaa gtgaaggtag caggccagag cccagctatc 157860
aggggaggag ccaggcagca tctggcttat ttctgtgagt gacagaggtc ttggcacagg 157920
caggtaactc tgtgggtttg gtgccttcca gggaagttga aagaatggag cctcatactg 157980
tatggcacag cagagcaccc gtaccacacc ttcagtgccc atcagtcccg ctcgcggatg 158040
ctggagctct cagccccaga gctggagcca cccaaggctg ccctgtcacc ctcccaggtg 158100
gaagttcctg aagatgagga agattacaca ggtaatgagc ctgaagtaag aggagacggc 158160
cagcttccac gagctttgat tgtccagagt agctcttaaa atgtagggct gctcctggca 158220
aaggtggggc tgatggttgt gtgtctctct tgcctgggag tcataataat catggcaatt 158280
tgcactcaca cagctcaatc caccccaggc tctgctaata ttttacagac cagtaagtat 158340
gcttcaaacc agtaagtatt ttccaacctt cccagctggg agagcagggt ctatatgccc 158400
aaccagaatg gggtcttgcc ccctggtaag ttagccactt ctaggagcac cccctttcca 158460
aaggccccca tctcacagct cagcctcctg actccctcaa gtacatccac tttcagtcct 158520
tgaggtcagg atgtgggaag gacacagtta ctcccaagga tccaggaagg ttgggttcaa 158580
ggagcacagc tgggaaagga cttcgtggca gagatcctga ccagcctgga ggcctagggt 158640
taaagaccca gagaggatct caagagatga tgtcagcaga tactgatgct tcacagatgc 158700
cttgaaaatc ttacagcatc taaaaaggcc ctgcatgaat cgtttttctc caatcatccc 158760
attgccaagg tgggccctgg tttggggccg ccagttcact ccacaaggcg gccaaaacca 158820
cagctgccca gagaagctcc agccactgag ctggacatgg cttttattcg tttgttagac 158880
tagaagctgt tcttctccct ctgagccctc ctgtagcaat ttgtgtgaga agaggtattt 158940
ctggttggac atattttcct tagctaaata ctacggctaa atgataaatg atgggtgata 159000
tctaagaaca ctgatgcttt aagttatcta atatcttctg tgaaaaacaa ataacaaatg 159060
gaaaattcca ccaacacata tcaagtataa attacggtca attccatttt aaatttcttc 159120
tactattcct ttaaaataga gcattgaatt atgtatggac taatctgctc tgtttccccc 159180
tgtgatttat aaactgtggc aagattcagt aattattaat aaggaactga ttttttttctt 159240 aaaatctgct actgacttca gccttgcaca atggaacctc actgtgatac cattctgcag 159300
tccagcagtc tactgagcag ggattaggtg gagagagggg gtctccatgg gaaggagatg 159360
cattcctggc tctcagagaa gccccctcaa gtctcagggg tgagtgggat gggcagacca 159420

159420 gagacagcag gagagcctat tcagagacca ggacagagtg acagaggagg tgagaaccag 159480 acggtgccag agtatggaag ccaaaggagg aggacgagcc acgttagagt ccaatgcaag 159540 gtcaggtgga tatgagacgg ggtgtgcgga gccggccatg gtcatggtgc atcaggagtg 159600 acgggcccag gccagtggag gctgcacctg gactctttgg gcaagagagc agttgccaag 159660 aaatagagga agtgagcgag ggggacgagg gaagcctagg gagtacttgc aaatggccag 159720 ggtcccagga cagcagcagg caagatggtc cctggagagg aaggttgagg accagagcat 159780 ctggctggga gaaagggcag cagctgcagt gggcagcgtg gggcacaagg aagatgtcag 159840 tgctgtggtt ctgaaggtgg acaactttgt ggtgacagcc aacctgctag gccagagccg 159900 tctggtggcc aaagtgcagg tggaggccac cccagggact ccgcagggtg ctgagttgag 159960 agcagaccct gggctgtccc cccgcccaga gactgggatt cagcaggtgt gggacgcctg 160020 ggggtctgca cctgtagcaa ccactcttag gtgcctgcag gcaccgtggg cttagggagc 160080 tggcagataa tgaaaccagc gaggatgggg gcaggaggca gggaagagct tgggttcctg 160140 caagagagtg gctgggaggc caggacatta ctggcatgga aacacaggga agcctgggcc 160200 tcaggaaaga agccatggtt gagcaaagga agctgagtgg gctgagatca gctcaggaca 160260 ctgtggtcat ccacacagga ctgcaaggga agccaagaac ccacgtggca tcgtctggaa 160320 gacggagttc cagggcagct ccaccggtac aggagacagt tcacaggatg agggtgatgt 160380 ctggagcagg accatgtgtg ctcacaggct cagcacatcc gtgcttactc gacaggctca 160440 agcagaggcc cagaagcctc aggtcgcttg ctcagggcac agcagtcagg aaggaaacca 160500 gacttgttct cagtgtactc ttattctcgt gggcacctct tgtctgcaat taatcggccc 160560 aagtcttgca tgcctctcgg gtccgatact gctccagtga ggttctggtg tgctgttctt 160620 ggatggcgtg aacggtggag aagatggtga taccaaactc tcctgtccat cggcagttgg 160680 tctgagcgcg caacggcaaa gcacatggag aactcccaag ttgcttctaa catttatttg 160740 tttgtgtatt tttttaaatc ctggatttcc tccacaaagg attgaaggtg gagttttcaa 160800 ataaacccgt gtcagtttaa gcccatctag agaggcatca gccgctagcc aggctgttca 160860 gcacgtgaac ggagcccccc ttgtatgaag agacccctgc taggagttac gggaagtgac 160920 acaagaaggc agtggggctt ggaggaactg tcacgctaat tgaggcaaag ggaaaagcag 160980 acctaagtac aaattgcaac acaaacatca tggttgccca gagaatgagc tgcagctgga 161040 ccagaacacg ctcaggcggt ggagtgattg ggaccacgtg gacagcaagg tggatttaat 161100 ttaagaacgc ttcatgggcg agaggaacct ggatatttgg cttttaaaca caattcaagt 161160 ggacagccat actggggagg tttgtttaca gatattcatc taggcatctc caccccttgga 161220 tgggcatcgt cttaacctga ccggtgggtg acctcagtgc agtgtggggg ccctgcagct 161280 ctgttgaata gcccccaacc ttgcactggg ctccttgcaa aattatgaat aagctttcca 161340 ctgcagagag acccaggaac aggggtgggg ggtgtgaagt ccatacaccc ggaccagcag 161400 ctgggagcac tgcttcagga ccctccccaa ggctgtcctc ctccgaggac atcctagaac 161460 attctgtctg gagatggtga ggacatctgc actttccctg ttcctagcca ccctcctctc 161520 atccgctcag caaatagtga ttgagcacct gctctgtgcc taatgccagg aatctagcag 161580 tgaacacacc gaaccaagcc ctgcccgccc gtctcccatt ccgtgtctag aaagagtgaa 161640 aagattggtc tgccgcctcc ctgtcgcact cctgccctca tcttcttaag atgaaggaaa 161700 ttgttcactt tatcaagcaa gacagacctg ctgcctcctc agggagaaga cgctgcagga 161760 aaaggcagga gagaagtcct caagtcacca cgacagcccc gcgttcgctg ggccagctgc 161820 gagggtggga aggcgagagc ccagtggctg agctggagtt ttgggctcaa tgggtaattt 161880 aaagcaatgg tgcgagaaat gaggattttg gaggctgtcc tcatagatga cccaggatga 161940
ggtgggcaaa gaatccaatc agatgggaat tgatccaaaa tattatagta aaccctctgg 162000
agctgggggg aggagtttag taatgagttt tagaaatggt gagtggcatc tggaacccag 162060
gataccagca ccgcccagga acagcatcta gagtgtcctc gtggatacac acagctctga 162120
aaggggttca cagtgggaac cgggacacgc aaagcccccc cagtgaaaac tagggaaata 162180
acaccagaga gccttcgggg agggaagcca gcctcactgg gtctaacact ggcaaggtct 162240
ggagacttca agacgagtga agagggcttt gcgtgcccca gcaaaacccc actgtgggca 162300
gcagagaatg aggacttttg tcttttcctc aagtccccac caaatgaagg tggccagcaa 162360
ctcactagtc tttactcttg agctcactcc ccatcccctc tcataactca cacctcggag 162420
gaggaggttt ttcttccagt aactcaaaag ccttcacatg ccccacttag tccctgtgtg 162480
tcagagctgt cggggtcccc tgggccgttt cccagcgtag gagggacagg tgggcagtag 162540
gcaggagtcc accccagctg tagcttcagg cgtcactcct gccgaccagc gtggggagga 162600
cccctgcagc gtgccccgcc cccgcctgac gggtagacct ttaacactgg cttcatctct 162660
gggatacctg ggaaggacct agagggtgag gtttgctggc gtctactcag ctcgcctgca 162720
gttctcagtt gtttttccaa caacacacca gcctccggag tgagaagctg gggacccctg 162780
ggaacttgag ggaagacaca gctgccgtcc caccaagggc tccaaggaaa gcctaaaggg 162840
gatgttctga aaggggctca gccctcagca cagaaaacag cagcccccca accctaggac 162900
agcactgtct agctgtgtcc ctgccccacc ctagacctgg ccagcaacag ccccaccagg 162960
cggtcctgag catgcggaga tccatcccca ttcccaccac agcgagttgc ggggggggcta 163020
cctaattcct cctggctcat cagcttgcca gcagctcccc tgacactcag cacccccctct 163080
tgtgttgctc tgtcctccac gtggaagtca aaggtgctgg ctggtcccag catgatgact 163140
ggtgcaagtg agtgaatgaa acagctgttc cagcctctcc ctccccgcta cccctccagg 163200
ctctcacaag tcccatctcc tccctgctcc gggtggcgta cccaccctgg atgtttcact 163260
ccttctcatg ccatccctgt ctagagtgct cagactgaca ctggagccca gcgaggctca 163320
gctgtgcctg ttacccgcag ggacggctgc tcccgccttg tcgtctggcc gtccagcccc 163380
agcggggcct gggagcgtct cccaaccctg ccaagctgcg atatcctgac acagggatcc 163440
gcgggactgc agtagatgga gaaggcgtct ctctggatga aaggcaatgc ttgtttcttt 163500
aaggtgtgtg ccatccggag tgtggtgaca aaggctgtga tggccccaat gcagaccagt 163560
gcttgaactg cgtccacttc agcctgggga gtgtcaagac cagcaggtaa tgcatgtccc 163620
gcagccctgt ggctcaccac tcagtgactt tccagttgta tccttagccc ctccatgtcc 163680
tgatgcccca gttaggaagt aacgtagcac ccccaaacaa tcatcacact gaagttaact 163740
gctttggagt ttttaaattt ttagtaactt ggcattccta tcatgcaagt catacatgtc 163800
cattacggag aaattagaag ctgttgcacg ttggcgtccg tgcttataaa gccttttcta 163860
tctgtgttgt taaagagaag tgggtcatgt tgggcgtgcc aaggctgccc cagagggcct 163920
ggagacggat gcgattcaag gccctggtgc tgtcctcaca ggccagctca ggggacatgg 163980
ctcttggaca ggctgaagcc tgttgatggt ctttctttca gtgtctctgg actctggctg 164040
ggtgtggggc tttcacagaa gctctcctgg cacctcccca gagagcccat gaggctgagt 164100
ttaccccaag ggaggatatc aggagctctg acctgggacc ccacgtatat ggccagttgc 164160
ccggttcagg ctgacccttc tgtgatgagt gtgccctcct gtgtggcctc tgcagtcagg 164220
ccctgggctc tgtccacgga gctgctccag ctcctggcat caccactttc tcagattctc 164280
ttccctgcca gtcctgcagc tgccctgttg tccattctca tttcacaaac ttccctgagc 164340
acccattatg ccccgcatgt gccaggcctc agaggccacg atgacaggac actgctaggc 164400
tccccaaagg cctgggtgac agatgcaccc accaaccact ggtgcacacc catgagggct 164460
caggcacggg tgcggccgtg caaggtcaag ccgggtgccc atgtggctct cgtggcgtcc 164520
tcgagctccc agccacagcg cactcactgg ccaaagtgca aaggctgtca ccctgctggc 164580
ctcactcact gcccacaaga ctcactccct gagggcgccc gagagagggt tttgccagag 164640
ccgacagttc caaaagtcaa atacgaacct cacgatgccc ttgggaaacc atgcgcaccc 164700
tcaggacctt ccagcagggc cagctttgaa aagaaaggat tcccaggttc tatgcaaggc 164760
ctccagcctc tccacctgtg tacgtaggaa cctcagaact gcactcacca agacaaaggg 164820
catcatgttt gacattcact cctgaagcct tcgtttcctc agaggaaaca aaggggcagg 164880
cctggggctg gggctgggtt ggcaaggccc tcaccctcct gcctttgctc ctacaggaag 164940
tgcgtgagtg tgtgcccctt gggctacttt ggggacacag cagcaagacg ctgtcgccgg 165000
tgccacaagg ggtgtgagac ctgctccagc agagctgcga cgcagtgcct gtcttgccgc 165060
cgcgggttct atcaccacca ggagatgaac acctgtgtga ccctctgtcc tgcaggattt 165120
tatgctgatg aaagtaagtg gcttgtttgt gggtacaaga actgatgagc cagcccccaac 165180
tttctgggcc cgtgtcctct ctccagggag aatttcccag ccttctgctt ccgtgtattt 165240
tgttgttctg agtaaggact ttgaacaggg aaggaggcag agatgatgaa atcaaagcac 165300
ccagacctgt tagttaatag cacttcccca cagacctggc caggagaagt tccaagtgat 165360
gctgagagac atcctggctg tccagggaat ttcacccacc tgcaacagag tcaacgtcca 165420
ctactgagca agggcagaga ggtggctagg gccagccact cttgaactca gtctgatttc 165480
aggtatcaga agaggaggtc ctgctgtctg tgctgtaatt tctcctccag gaaagactat 165540
gccatcggct tctctgtaac acaggatgtg tgcgctgggc gtgggtcagg gtacatggga 165600
ttggtggtca gagctggggg agagccctcc tcggcagagc tgcggagatg aaattgggag 165660
tcagatgtgg gcggaaggtt tgcagacctc cagacatgaa aaggagctgc tgaccaacgt 165720
cagttgggct cggaagggat gggtttgtct ttgccgggca tttcacaggt ggcaaccgca 165780
cccctgaaca ctagacaggc agtgttttcc tcgtcctaca gatggggaat caaagctgag 165840
caggggcaaa ggccacaact agtcatgatg gaggtgggac tcggactcag agccgcaagg 165900
ccaggtgtct tgctgtccca ggagggtggg ggctggacag gagttgtagg cccaagaccc 165960
catgccatgt tttcgtaatt cgcctcgccc tgggagacac aaaagcaggg cttgggttaa 166020
attgacaggg gatagttctc aaacacatta aagaagctac cgtttggcac tcgtggtctt 166080
ccaggtagca ggcctcccca cggccctcct ctctgggccc ttactgctca ggatgggtca 166140
ttgatccggc ctgtcatggc actgccgtta cccctgtgga caagacccag caaatcttaa 166200
aagacgtata aagccatcaa ataacaagac accccctttt tttttttttt tcgagatgga 166260
gtctcactgt ctcccaggct ggagtgcagt ggcatgatct cagctcactg caccctctgc 166320
cccttgggtt caaggaattc tcctaccaca gcctcccgag tagctgggct tacaggcatg 166380
cgccatcacg cccggctaat ttttttgtat ttttagtaga gatggggttt caccatgttg 166440
gtcaggctgg tctgaaactc ctgacctcaa atgatccatc tgccttggcc tcccaaagtg 166500
ctgggattac aggtgtgagc cacctcaccc gtcccagact ccctttagcg gggaaacaaa 166560
aagtcatgca agacacattt cacagccttt gcaaacgctt gccctgggct gccagccaga 166620

-continued cctttgcaaa ggacggaggc gccttcatcc ccacccccctt cccaagggca cagttggccg 166680
cccttcttca ccccgacatc ctcactcagc acctgcttta tggcgtatga tgccacctgt 166740
gggggccctg agggggacac gtgcaggtgt ggcaagcagc tgttagctcc caggcccaga 166800
gcaccccagc cacttaggag tggtgcatgg tggtgtttca tgaggcgcca acccagataa 166860
taagttatga cattgcaggt gggagttggg gtgacccaaa acttccccaa gaggcacgat 166920
gactcgccgt aggttcctgt ctcaccatct agagcagcca gatcttcata catagtttc 166980
cctgagaaag caccgtggtg ggcaagcggc agcctcaggc tctccacccc ccacctgccc 167040
acacccggcc actttcatga agatttccac ctcgttaaac tctactcagc ccaccaggaa 167100
ttggcctcca tccctgttga aataagcaga accacctcag aggcctggtg gttgtctgag 167160
gaccgttttt acctcagaaa ggggaggtga gaattctgtg accccacacc aggtacaagc 167220
ggcctctggc tgctttattt ccacccattc cggaggtgga ctcggggaac agcccacccg 167280
cacccccgct ttgaaatgcc gggggcctgc ttgcccagat ttcattcctg tcagtgtcgt 167340
cccttctctt ttcttatctc gctatttttc tccaggtcag aaaaattgcc ttaaatgcca 167400
cccaagctgt aaaaagtgcg tggatgaacc tgagaaatgt actgtctgta aagaaggatt 167460
caggtaaaac cccctcgaaa cctgaggaat gtcagggcgg tggcgctgct tggagtgtgt 167520
tatggattta ccacgttggt gcatttctcc taaaagctga actgtcagag gcccaaagcc 167580
attgagggta aagattccga gtcctggaaa tcgtgtgtcc acttaggatg gaaagggaga 167640
ggatgggcgg aatctctaca ttttacacaa catgggcgaa ttgggcaaag cagcacttga 167700
tcacatcacg tacagcacag ggctgtgccc agatccgcct cctttcgctc cagcacctcc 167760
acctgctcca gttcccctcg ctgtctgggc cggggatggg ctgtagcggc tcacccaccc 167820
tctctcctct gcatccctcg gtcttctctt tttctcccag ctcctgacat cttcacggct 167880
tcctgagggt gctctttacg ttcctggttc tccctgttca tcaggctcag ccccataaag 167940
ctcagcatgc attttcttta aaatcattct actgggttaa tgattgttct tggaatattt 168000
tgaaatgttt cttcagccca tttaatgcaa ccaaactgca tttaatgcaa tcaaatatac 168060
attacctgtt cctccgaatt gctgtctaaa atcttagaac attctgttca aaatttttttg 168120
ggggacactc ccatagtagg gagactagca ccatggtccg cactggaagg atcacctcat 168180
gtccagatgc aggttctgat gcagcaggtc tgggcagagc ccacgactct gcatttccgc 168240
aggctggcag tggtgaggat gctgcggtcc aggcagggag ctgcttttgc agggtgaggc 168300
ggtggagggc tgcaacacac ccccagcccc gtctcccttc tcaaatgctg tgaggactgg 168360
aattctccat agaagaagtt tcttttttgg agtaaagaac aaaggaagaa aacttactga 168420
gcatatcttc tcttattcca ggggcttgca ccagtgttgc ctcatttaat ctttgcagca 168480
acctgtgaag tagacataat tcttactcgc attttacaaa caggggagat gaagtttccc 168540
caggaggcac tatgctactg ccttcatttc cttcagcctg cctctttctt ccagatcaga 168600
gtactgggga gaagaggacc ccaagcagct aggagtccag gagagggaag gcaaagcaag 168660
gctcccaaag tcatgcatca catctgctgt catttaaacc tgttggctgg acaaggcagg 168720
attaggagtg aaaggatgaa ctggcccagg aaagggatcc cccaaagata aaagagttgg 168780
aagaggaagg aggcattccg ctggcggcct gggagaggcc agctttgatg tcccaggctc 168840
tgcaggtcag gcagcccagg agtggatcct caacccaggc tggtagctgg gggcatcagg 168900
aagaggaggc tctgtgttcc cagctccctg gaacctgcct gtttcccagc agagaagtgc 168960
tgaggggtcc ccgggaatgc atttatgcat cccgtcccat cctgtaggag agggaaatcg 169020

```
gatactcaat gtaggaatgg tgtgctaaag agaaaacgcc tcctgtcggt agccccgcca 169080
catagaggca gtgcttccgt cactgacgag ctttcagaga ggcgtgcaaa ctccagacgc 169140
atcgccagcc gtcagccaca gagagcttcc gtttattgcc caatatcctc ttaagctgtg 169200
acttctaatc actgcagtca tgttaaagca gcaagagagc agccgagccg ccgcctctgg 169260
ccctccatct cttcaggggg atcaacacag gaaaggtttg caggggagtg tcagttataa 169320
agacatgatt taactgccat tcgcagtggg catggcacca tgaagaggaa gggcgccggg 169380
tgggtgtccg ccatctatgc agaggagctt gccaacatac agacgtcttc ctgctaaatg 169440
caggtgtaag agataggaaa aaccagtgtt ttctcctact ctcacacaca aaatacaaca 169500
cacttcacct ctggtagcca aaacgtgtgg gtttttcccc acacaccaag cagttctcca 169560
gtgaaccgta agatatacgt aataaatata tagctcaggc tgaacgcagt ggctcacgcc 169620
tgtaatccca gcactttggg aggccgaggc aggcagatca cttgaggcta ggagttcgaa 169680
accagcctgg ccaacatggc gaaaccctgt ctctactaaa aataaaaaaa atagccagac 169740
atggtggtgc acgcctgtaa tctcagctac tcgggaggct gaggcaggag aatcgcttga 169800
acctgggagg cggaggttgc agtgagctga gatcgtgcca ctgcactccc acctgggtga 169860
cagaatgaga tcctgtctca aaaataaata aataataaat aaataaatag ctcaattctg 169920
acgctactag atgtgtcaga tcctacaaat tgagggctca gcccaagact gccccacttt 169980
gatgtcaatc acgagtccca catggtagcc tgtgcttctg agtgaccagc cataaatcgg 170040
acttgccatg acccctcctt gggttcgatt aattggctaa agcagctcac agggaaagac 170100
tttacttaca tgtgcccatt tattacaaag gatatggcac acagccagat gaagagatgc 170160
ggagggtgag gtttggaagg gttgagcgct ggaccttcca tccctatggg gctgggctgg 170220
gctaccctcc caggatgtgg ttgtgttctt gttcaccacc ccagagctct ccaaaccctg 170280
accttttggg tttttatgga ggttttgtta catagccatg attgattaca tcattggcca 170340
ttggtgatca attcagcctt cagcccctct cacctcccag gagggaagtc agagtagtag 170400
ggctaaaaat tccaaagctc tgatcaatgg ttggttccct ggcagccagc ccctgtctag 170460
aggctgccca ggaaccccca gctatcagtt attaaagaca tttagcactt tgataattcc 170520
aagggtttta ggagctgtgt gccaggacaa agaccgaaca tatatttcct tttttttttc 170580
tttttctctt cacatatttc ttattataaa tcccagtgtc atagcaggag tctccgggtc 170640
tgacagatgc accccagagc ccttgctcag tatggcaaac ccatctagaa catgtacgtc 170700
acagactgta cacagtataa tctcaggaac taaagagata atagtaggtg atattgattc 170760
acactgctgt gtgccagaca ctgaaatgtt tatgggtatt agctcattga gtcctccaag 170820
caactttatg atgtagaaac caattaacag gaagggaaac agatgtagag gggctggctg 170880
gcttgcttgg ggtcgaacac tgggaaggtg gcagaagcca tccacgtggg tggtctagct 170940
cagcatctgt gtctctgtcc agcactcggc tggctggagt gaagtgaggg cacaaatggg 171000
gcgaaagagg aaggtagggg ctgcatctga caggcctgct ggggctccag agggcgtctt 171060
atttcaagtt cattgcgaag ctgcagaagg ttccaaggtt tcaagcaaga gaggcaagag 171120
cgggttgggg ttcagggcca gccttgtagc cgacagcccc gtcacacgcc ataaatgcca 171180
acacttcaag agggacttga cactgagact gagctagcgt gccaccagtg atgacccaca 171240
cagctccact tctcttcatg gggtttggat tcgagttgga gaaatgacag taagaaaaag 171300
ctatcactgg gtcaaggacg gagcctggcg cctgctgcct ggtgatggga gctttgcttc 171360
```

ccagggcctt gtaccccttc ctgctgggcc cccagcggac tgcgggatgg ctttcccgac 171420
tttccttagc tgagaacttt cggtgacaca aagaactgtg cctcagccac ttacatctcc 171480
tcttgggaaa ggtgctagag ggcaagtcat aattagactt ttggaatgga tgtggaaatc 171540
tgcctctttc ttttcaacag ccttgcacgg ggcagctgca ttcctgactg tgagccaggc 171600
acctactttg actcagagct gatcagatgt ggggaatgcc atcacacctg cggaacctgc 171660
gtgggtgagt tcaccgcctg cggaggcctc gggccagcgt cacccaagcg taggctagct 171720
gccttgaacc cgagaaagcc ctaggacttc gtgggcttct gcatttattg cagcattaaa 171780
atgcaagggc aaaacaaggt acaaaggccc taccagggac tgggggccgg gagagtgggg 171840
atttaatgtt taatggttac agagtctcaa cttgagaaat gacaattgtt ctaaggatag 171900
atgctggcaa tggttacata acagtgtgaa tgtacttaat gctgctgaac tgtgtactta 171960
aaaatggctg agatggtaga ttttatgtac attgcagtgg ctcatgccta taaccccagc 172020
acttagagag gcagagatgg gaggacagct cgagcccagg aactcaggac cagcctgggc 172080
agcaaagctg tgagaccccg ttctccacaa aaggaaaacg ttttgttgga aatttttttt 172140
aaaaccatgt ttttaaattt gaaacaaaat cccaaaacaa tgcaaaggcc cactttgaac 172200
acgcagcctg aggttctcat tagaaaccca gccaggcagt ggcttatttc agatggggaa 172260
agggataaga gatgctcacc actcataagc catcttgtct cagagctcag ctcttgctgt 172320
ggaacggcgc ggacagaaac acaacaccat aaacattgag agggctttgg gagaggcggg 172380
aatggatcca ggtggggatg gggatgtttt caaacatagc cttagttctt tgtgcctatc 172440
ttcacttatt ttgaacattt tttcaaagag gaaaagaatt ctataaacaa ttttacatgt 172500
attataattg cccacaaaga tgatggcaca gatgtctccc aggcacagtt tttatgcaga 172560
atagcagaga attcattcat tttattggat tttgttttgc agagctattt gcacagtaag 172620
ttgaagtgca ccatcagtct gtgggctcgg atatgttttg ggttaagttt tctcctctct 172680
ccttcctgtc cttggtactt tggtcctttc taagaaactc acatcatatg agctttttct 172740
gcagtaatac tttaagaatt aagtctctac tggccgggca cagtggttca tgcctgtaat 172800
cccggcactt tgggaggcca aggcgggtgg atcacctgag gtcaggagtt caagaccagc 172860
ctggccaaca tggtgaaacc ccatctctac taaaaataca aaaattagcc aggtttggtg 172920
gcaggcgcct gtaatcccag ctactgggga ggttgagaca tgaaaattgc ttgaaaccgg 172980
gaggtggagg ttgcaaggag ctgagatcac acccctacat acttcagcct gggcgacaga 173040
gtaagactct gtcaaaaaaa aaaaaaaaaa aacagaatta agtctctgct aaaccagttt 173100
ccatgatact actgtgcctc agaaatcctg cagaatgggc acacccctcc ccacgtggcc 173160
ggccatgagc accccatgca gctccctgcc gtatgtcctg gaatagacag gcctgatgaa 173220
caaggctgtg gccaaggcca gtgtcctcct atgattgcca ggctgacctc agaccaccca 173280
ggggagacat gtcctcctca gttccctcct ggggcagccc tcaaggccac agtgctcagc 173340
atctggatgg gttccacccg ctggcagctc agcagatttc cccagcagtt tgcctgtcgc 173400
ctttttgtct attattttta ttatttcttt gacttattta gcccagatgg attaggcagc 173460
atcactgatg ttgcttattt aaatttcgta gtcacttgaa tccataacat tcaggcatac 173520
agttttgcaa ctctttgatt tcaataattc acttttcttt ctttgagtcc ccagattgcc 173580
tgatggcaaa aagctttata gagtcccttg gaattctcat ctcaaaccag tgacttctcc 173640
atcacttcag ctattaaatt cattggtgag caggtccaca gctctggggg tctcccctgc 173700
gccccatgcc ctctggcctg gggttctttc taagctcctg ggaacgtgta catctatccc 173760

-continued ctggcagcct cttgggagag agacctcatt ttcctcctct gagtcactgg aggcttcttg 173820
ttccatgtca ggtgtggacc tcattggagg cagctgttct cagctgccta cttcctgtgc 173880
cctggagacc caggcccacc tggcattccc ctccctgttc ccattcagtg accactgctg 173940
tccaccaccc acccaggggc ctgggcacag tcgtggggag ggtcggagtc aggcatgagt 174000
gcttggggta gggcatggcg gaatctgtcc ccacccttgg ctcacagtgc cccagtgcac 174060
ttggcaggca actcgatcga gatgagcctc tcatcctcct gagtccaggt gccccgtgtg 174120
tcctggcatg gaggttgtaa tccttcgggg ctgctggcac agctgggtta atgcagtggc 174180
cccgtgggac gcgacttacc cacctggggc atggcatgtg gattagcagc tgacagcctg 174240
cagggcacac acataccaag ttgcggggca gtgccccaag cacctgtgac ggtcagccct 174300
caagcatgag cgtcctgtgc ctgagacggc actacttgaa acagcaaatg agaaacacca 174360
caacagacca agagagattc aaaagaaagg aaaacgcttt ctgttttagt ccctgtcgtg 174420
gcacattctt ccagctttct gaacaaaggc tccatgtttt cactttatac tgggccccgc 174480
aaacaacata gcaggtcctg tataagcaca gcccgttctg ctcttattgc tatgattgtg 174540
ggtgctttta aagtgttcaa agtctataga gacttgcgac ttaatggaat ccttaaaaga 174600
ctttcactga gttatgaaat tcatattttt tagtagttga gaaaataggt cgcttagaaa 174660
atcaacccac tttaacagct tttttattgc ggtaaaatac acatcacata aaatgtacca 174720
tcttgactat ttttaggcat acagttcggt ggcattaagt gaatttacat ttgtgtgcca 174780
ccatcgccac cacctccaaa taaatgtgtt ttaacaactt tgaagcttaa tacattgagc 174840
atgaaactta agtacaaaca agaatgagct ttctttccca cttgggaggc tccacaggtg 174900
ttaaggaccc tggtgctgga ggaaggatag tggggaagac gggttcagca ggtgaggcgt 174960
gagaggtaca acggcaggcc ctgaacagct cccaaacccc actcagagtg gcaccccgcc 175020
tggtgtatga gacccaccca ccagatgctc ccagagacca gtgatgggga ggggcggcat 175080
tggccaaagc atacgagcag cctctgctcc agaacaacat aaaccagaca gagtcccgcc 175140
cccggggcac agctcttcca ccgcacctca ggaagagagg gagacacctg ccatgaagac 175200
ggtggtcctc aagaggcccc ttgaggtccc tacatctgcc tcctgctcaa aaccctgtgg 175260
ccttctcggc ttcactcttc ctgactctcc aaggaggagc ttctcctgca ggagctcaga 175320
attccctccc aggcttacgg ctgtggttct gaggtgtgaa gccagcccca gagcccaggg 175380
ccttgtgctt gagccctcca ggctccggaa cctctgcaaa gggattttcc cttgatgcag 175440
cgagaggccc catctgagtc cagagcagac tgcaaggcct cgatctgcga ccacaatcga 175500
actgaagcag ctgtgaggag gtttacctgg gcattgtgat tatcatagag cccctgagat 175560
aatctcctcc ctgcctgtaa ccctctccgc tgtcagtcag tgactacttc actgcccctc 175620
tctgacgtcc catcagttgc tccctggaga cacctggccc agaggaggtg ctatctagtc 175680
aactagtcca acatctgacc caggtcgaca ggtcctcctc ggaccctgag ccaacctgaa 175740
ggttttcctc catgactcgt ggccctttgc tcagaactgt tgtgtcttcg agtctctcct 175800
ccctgcccta taaaccctta gtcttaggca tttgtttctc tgttgttgaa aacgccctgg 175860
ctgtacacac caaacacctg tcaacaccat tcccaaagat ctcttctttc atcttccccc 175920
gtcatcttct acagcgttct gtgcaatgga agggccacaa acgcaagcca cgggtgcaat 175980
ttgaagttgc ctagtaacca tatcttaaac agtcaaatga aacaggcaaa aataatttta 176040
gtaacatatc ctattcaacc taatgtgtct aaaatattgc catttcaaca tgtatccata 176100

-continued caaaaaataa atgagctgtt ttatattttt tatatgaaga ctttggcact ggatttccaa 176160
gtgttcaggg agcagaggtg ggcctaggcc tgttggaaac agggcccatc atcgtggcac 176220
ggccagtggg caggtgtgct ccctctgaga tcatctcatg cctcgatgtc cccgtctgtg 176280
aaatggtgat ggcgatgccc acctcctggg agtgggtgag gacggcccag ctcacagaac 176340
ctgggaaatg gcagctgtgg tggtggcctg gggctcctg aatggtaccc ctgatctcac 176400
aaggccctga agcaggcctg ggcatggtc ttctgccagc catccctgat acctgcttct 176460
tttcctgtgt ctctcagggc caggcagaga agagtgcatt cactgtgcga aaaacttcca 176520
cttccacgac tggaagtgtg tgccagcctg tggtgagggc ttctacccag aagagatgcc 176580
gggcttgccc cacaaagtgt gtcgaaggta cggtcctcct ggcggggaac ggcaggcagc 176640
tgtgtccagc aaaggagtgc ctggagggca gagtctggca gcatcttccc caggggccgg 176700
ggagggcatg ttgcatcacc ccactgtgga caggagccca tttacagagc tgctgagggg 176760
ccttcgtccc tttgttcact ggatgcatat ttgttgggtc cctgctgtgg gcagacaccg 176820
tgcagcagcg ggataagatg ggaagcagaa tagcaaggtg ctcacacccc attggtggac 176880
tacgcgggac gtccctgccc atgtcgcgct cagcatgcat cctttgcact gtcgataatc 176940
agagaaacca tgttttgggt taaaaaaaaa tttttttgga gacacactct cactctgtcg 177000
cccaggctgg agtgcactgg tgtgacctca gctcactgca acctctgcct ctgggattca 177060
agcaactctc atgcctcagc ctcccgagta gctgggacta caggcgtgca ccacaatgcc 177120
cagctaattt ttgtttttgt tttcgttttt tttgagatgg agtctcgcct gtcgcccagg 177180
ctggagcgca gtgggcgatc tcggctcatt gcaagctccg cctcccagat tcacaccatt 177240
ctcctgcctc aacctgccga gtagctggga ctacaggcac ccgccaccac tccccactaa 177300
ttgtttgtat ttttaataga gaccgggttt caccacgttg gccaggctgg tctcgaactc 177360
ctggcctcaa gtgatccacc cacctcagcc tcccaaagtg ctgggattac gggtgtgagc 177420
caccacacct ggcctaaaat attttttta gttagatact tagagaaatt aaaaagatcc 177480
tgacaatttc ctcattctaa agctgttctc tgcacagtcc acgcacatct attttcaccc 177540
tccatatcct cctcttgtgc ttcctcccat gtgtccctcc acagagtcac cattcttatt 177600
tgatggccct ggacccttct gttgttggac atgagctgtt aaaggaggag ctgtttgctc 177660
tggtctcctc ttttctggct gaatattgcc ctatgttggg agatcatgaa ctcaggaccc 177720
agaacagggc agggcaacct gtcttattca gggtgggagc aacattgagg agtttgaagg 177780
gacctgtgag ggtgtgacga tggggtgagc tgtgaggggt gacgatgggg tgggctgtga 177840
ggggtgacga tggggtgggc tgtgaggggt gacgatgggg tgggctgtga gggtgtgacg 177900
atggggtggg ctgtgagggg tgacgatggg gtgggctgtg aggggtgacg atggggtggg 177960
ctgtgagggg tgacgatggg gtgggctgtg aggggtgacg atggggtggg ctgtgagggt 178020
gtgacgatgg ggtgggctgt gagggtgtga cgatggggtg ggctgtgagg ggtgacgatg 178080
gggtgggctg tgaggggtga cgatggggtg ggctgtgagg ggtgacgatg gggtgggctg 178140
tgaggggtga ccatggggtg ggctgtgagg ggtgacgatg gggtgggctg tgaggggtga 178200
cgatggggtg ggctgtgagg ggtgacgatg gggtgggctg tgaggggtga cgatggggtg 178260
ggctgtgagg ggtgacgatg gggtgggctg tgaggggtga cgatggggtg ggctgtgagg 178320
ggtgacgatg gggtgagctg tgagggaagt accaggcgtt agcctgcttt cacagtgcta 178380
aaaagaaata cctgaggttg ggtgatttat aaagaaaaga ggttgaattg gctcacagtt 178440
ctgtaggctt cataggaaac atggcgccag catctgccca gcgtcttcac tcctgatggc 178500
aggtgaagca agggcagcac atcacatggc aatagcagga gcaagagagg gaaggaggcc 178560
gggcacggtg gctcacgcct gtaatcccag cactttggga ggccaaggtg ggcggatcac 178620
ctgaggccag gagttcaaga ccagcctggc caacatggca aaaccccttc tctactaaaa 178680
aaaaaaaaaa aaaaaaatgc aaaaattagt tggacgtggt agtgtgtgcc tgtaatccca 178740
gtcttacagg aggctgaggc aggagaatcg cttgaaccaa ggaggcggag gttgcagtga 178800
gctatgatcg caccatgcac tccagcatga gcgacagagc aagactccat ctcaaaagaa 178860
aaaaaaaagt caggagttgc cacacacctt taaacaagca gctctcacat gaactcactc 178920
atcaccaagg ggatggtgtg aggccattta tgagggatcc accccatgat ccaaacacct 178980
cccaccaggc cccacctcca acactgggga tcacatctca tcatgacact tggaggggac 179040
aaatgttcaa accatatcgg ggggcttccg tctgaaaaag actgaaaatg agggagccct 179100
caaaggcttg tgtcagagca ggggaggggt gcccatggct ggctgccagc tgggtaccga 179160
ttcaccacac agtggggtct gcctcccagg ctgtgtgtaa gaaccactgt gggttgtaac 179220
ctattcccct agaaacaaag ccctacagtg agcccatgag ggaccaccaa gcccttgcac 179280
ttgtctgacc cacagcagag ggacctggtg gcggttacgt atctcggcaa gcatcagccc 179340
cttctactgc gttgctgtaa tggaggaaac ttgccacccg cttgcaaggt gcagccttgc 179400
tgagtcctgc acggggccct gggcacagtt gtctgaagtt aaacccttca tggtaaccag 179460
tcagctggtt ctcagataat taaatatagc aatccaggga gaacttggaa ttaaacagtg 179520
ataatcactt tcatttgtca aatgccctgg atttcagggc atgctgatca tgcccacagc 179580
tgtgcaactg gacccctgca ggcagcccca ccgcaaacct ctctttgccc ctcaggaggc 179640
agcaggcggg cagccccacc gcaaacctct ctttgggcag tggaggacag gagtttcctg 179700
ggtacttgtt cccaggtgag gggcagcttt cggccctgca gaggctgaca gtgctggggc 179760
tgacacaccg ggtcttggag aagcaccccc caggaagagc gtcagtgtgg acgcctccca 179820
aaggaagcaa ggccttggtc cgattggttc tgcggggtct ctccccactt ggacagcctg 179880
agctgagaac cacaggcatc ctccaggccc cagaatgctg gtggacgccg tggccgtccg 179940
ctgctgctgt gccaggcagc tccgagggag catgtggcca gacgggctgc gttggaacat 180000
gcaggtcagg acgcaggcct gctgggttgg caactgcagg tggaagccga ggcccgacgc 180060
tgagaacaat gcctgataag ttccctaaga gaggggccga ggcccgacgc tgagaacaat 180120
gcacgataag ttccctaaga gaggggccgg acaccctcaa gacctagtga gaggacccag 180180
caagagccag cctggacaac ttggaagaaa aacaggcctc tgtggagtgc ttgccagcgg 180240
gggaggcaaa ctcctcatgc cctggccctg cctccacttg cccccaggct cagcgggggc 180300
agagactccc aggggcacag cttgaagggg cacgccttct gccaatgcgc atgctgcgtc 180360
caggctggag catgaaagcg tcagtcttct gcatcccact cctgaacagg caggaggctg 180420
atgggagtgg cctctgcaag ggagcaggga cagagggctg catccggcat ccctgtcctt 180480
ccagaatgtg gcagggcaaa gcggccatgg tgtttggggg aaaagtaggt accatagatg 180540
gttgcagaac cagaagcatc ttaaaagcca ccctgcccaa agctggtgct gcccacgagg 180600
acccgctgct gggcacggta atcctgacgg aaagcaggag ctacacaggg tctcccaggg 180660
agagccgtct gcactggcct aacggggacg ggagcatcac ccatctccct gagcagcatg 180720
gtgatggatt atttccccag acctccagag gagagcccag cctggccacc accttgccct 180780
gaacctcgtg agaccctagg tggagagccc agctgcacct gcctggactt ctgcctgcat 180840
agcggggagc cgctgagtgg gtgttatttt cagctgctga gtgtgtggca acctggttag 180900
agcaatggaa aaccgaggcc cctgccatcc tgctgagctg ggtgaggttg tatttgaaga 180960
agcaagcaag ccgtaacctc ctggctgtcc accgcagcgc gctcctcacc acagttcttc 181020
actgatgaag cagccctcag ccgtggcctg ggggcactgg gcccctgggt cctccagacc 181080
actgacatct ctttaaatga ctcagctcgg ccctggttct cgtctcacca gtggcattgt 181140
ctgtaagaga aaccagaggg tctgtgggga aagtcataac ctgtactggg gcatcagggt 181200
ttggtggctg ggccaccaga atgtgcaagg gcaggtgtgg ggaggggcga gcatgatggg 181260
ggcagaccca tggggcttcc cacaagtgca caaccccctc tggcaagtcc tctaacccca 181320
tcctttcctc tggggcggcc tggatgggaa tattagaaag gctcgtgggt gtgagtttgc 181380
ctgtggggtt tacacattta caattacaga ccaagggctt gagctctagg ctcagcatcc 181440
tcagacacac taggaataaa acccacctcc cacccaggct gaagcgatgc tgcacctggg 181500
gctccagagc agcggagtcc gtggtgagac cagaccccat cagagggctg ctctgcaaag 181560
agccccacga ggaggcctgg tgtctgagcg tgggaaggct tcacacagca gggaggggac 181620
atctgtataa agcaaagaac tgccccccag ggaggcccag gcatgagcac aacaaagctc 181680
caagccctgc ctatggggcc tgttccaccc ttaactggca acaatgggga ggtgggcagc 181740
tgatgcaagc actgtggaga ccgagtcacc gggctctgga ctcaggacag gcagcagcat 181800
agccggggtg cactcacggc cccaggatgg gaaacgtgct ccttcaagca ctcggcccgc 181860
atcggcaagt gctttctgta gagggcacaa tggtcagtcg ttcaggcttt tggggccaca 181920
ctgcctctgt cacagctact cagctcagcc actgctacac aaaagattgt caatgaatga 181980
gtgtgactgt ggtccaggat aaatgctgga tgtggccctt gggctgtagt gcaccaaccg 182040
tcccctgagg tcacgtttac cctgcattag aaatagccct ggctggtgtc catctctgcg 182100
caggctgggc caggaccgtc cgagaggggc aggaattgtg gggcatctct cccactcccc 182160
gagggtaagc aggcatggcc acatataggt gacagcagcc ttctggtcag ctcgagtcag 182220
gtgtgtcaca tccctgggtg gagtctggcc tggaccccaa gcctacagcc atcgcagccc 182280
ggcagccgct ggagagagaa gactgacaca gctctgggag ccgtgtggtg gggtgggggc 182340
tgggtgccag ggcccaggag ggtgtccagg tgagctgcgg gaagcctcgg aggcctggcc 182400
cctgatcctg ggcttgctcc tgccaactgg ccatggctgt ctctgccctc ccagggcaat 182460
agtgaggtca gacaggagaa aagacatgca gacactcagc ccctgtgtca gggaatggtg 182520
ggcgacacag cctctccaca gaggaccgag gctgaggggg tgggaaggag gtgcagggag 182580
gtgagggttc tgggaaggga gcccggagtg gtggagcctc ttccccagac ttcagcagga 182640
acggtatctt cccacaggtg tgacgagaac tgcttgagct gtgcaggctc cagcaggaac 182700
tgtagcaggt gtaagacggg cttcacacag ctggggacct cctgcatcac caaccacacg 182760
tgcagcaacg gtgagcagca gctgggttac cctggggctg cctgtggagg agctcagctg 182820
gccagctcgt gctccaaaga gaaaagcaaa gccacatagg catggcggct ccacagacag 182880
gcgttcgtgc ccctgatccg attgactgtc tgggattcct ctagctgata tggaagacag 182940
ctgccctgtc tcccagcttc cctctaggcc tctcacatcg atcagagagg catcccagcc 183000
actgctgatc tgtttattga gtgactccta aaaatgattt tgtccttgta ctggtcccac 183060
tgccatgcca taggccgccg gtggcccgga tgtgacgaca taccataaaa gaagcctgac 183120
ctggggggtc aaagccagga agcctggagg gtctctgctc aggacgaggg ggacagagcc 183180
cagagtagag cacacgctca gcagcagcaa tcccagctct gcagggatcc agcatggacc 183240

-continued tgcatctgtg ctgcaggaga gccctggctc tgccatagga tgggggacaa ggacaagttg 183300
taaaaacaga aacttaaaag ggcaccaaag ctaagtgccc agtttgggaa ttccaggcac 183360
caaggagggt tggcaggact cgggcctgga ggtgcagtgc aggagtcatt gtagacacac 183420
gggcagggaa gggggctctg gcccagcaag cagcagggtg gagccacatt ctgacagcca 183480
ggagaggaag gctctctgct ccagtgtcca gggtcagggc aggtggtcct tgggtatgaa 183540
gctggcactg gccctgtcca ggcagagcat ggagcttgtg gagggccctg ggatgcctcc 183600
ttgccttgtt actggttatt atttttgggg ggtggcggga gggttgtcta attatgtccc 183660
ttcaaaggcc cagaaactac ttctttggga agtcacctgc ccaggttatg tatctagccc 183720
aaaaaagtgt ggttgccact ggagggcctc ccaggtccac ggatgatgca tcctcaaagg 183780
cctcttcccc ttgctgcagc ggtgtcctca gcaagtcctg tccacggcgg ctcccttccc 183840
cccatcccca ctcctccctg tccgccccct ccaccctgga agcagcttcc attccctcct 183900
gcctccaggc ccgtcctccg gcctccccta cagtcttcct cctaagctcc actgccagca 183960
gttgtccaga aagacaggtg cacatgtgcc ccacaggccc aggctgggtg ttctcctgag 184020
atccctccca caccaccccc acatcctgct catgaatccc cttgtcactg agactcagca 184080
agagccccat ataccagtgc cctcccgcca cacagggctc ccagagtcaa gtgcattgca 184140
ggagaggggc ttcaagggct gccatcctgc tgcccacctc tgtctgtgtc cctcttgccc 184200
agggcaccac tgatgcccag catatgtgga atgattgaaa caatatttat ttatgtattt 184260
atttatttat ttttgagacg gagttttgtt cttcttgccc aggctggagt gcagtggcat 184320
gatctcagct cactgcaacc tctgcctcct gggttcaggt ggttctcctg ctttagcctc 184380
ccgagtagct tggattacag gtgcccacca ccatgcccag ctaattttta tattattagt 184440
agagacgggg tttcaccatg ttggttagac tggtctcaag ctcctgacct caggtgatcc 184500
acccacctcg gcctcccaaa gtgctgggat tacaggcatg aggcaccgcg cccggccttg 184560
aaacaatctt cacaggcacc gaagactgac ctttccctct tttgcctttc ctgatgcggg 184620
gccccagctg acgagacatt ctgcgagatg gtgaagtcca accggctgtg cgaacggaag 184680
ctcttcattc agttctgctg ccgcacgtgc ctcctggccg ggtaagggtg cctagctgcc 184740
cacagagggc aggcactccc atccatccat ccgtccacct tcctccagac tgtcggccag 184800
agtctgtttc aggagcggcg ccctgcacct gacagcttta tctccccagg agcagcatct 184860
ctgagcaccc aagccaggtg ggtggtggct cttaaggagg tgttcctaaa atggtgatat 184920
cctctcaaat gctgcttgtt ggctccagtc ttccgacaaa ctaacaggaa caaaatgaat 184980
tctgggaatc cacagctctg gctttggagc agcttctggg accataagtt tactgaatct 185040
tcaagaccaa agcagaaaag aaaggcgctt ggcatcacac atcactcttc tccccgtgct 185100
tttctgcggc tgtgtagtaa atctccccgg cccagctggc gaaccctggg ccatcctcac 185160
atgtgacaaa gggccagcag tctacctgct cgttgcctgc cactgagcag tctggggacg 185220
gtttggtcag actataaata agataggttt gagggcataa aatgtatgac cactggggcc 185280
ggagtatcta tttctacata gtcagctact tctgaaactg cagcagtggc ttagaaagtc 185340
caattccaaa gccagaccag aagattctat cccccgcagc gctctccttt gagcaagccg 185400
agctctcctt gttaccgtgt tctgtctgtg tcttcaggag tctcatggcc tgaacgacca 185460
cctcgacctg atgcagagcc ttctgaggag aggcaacagg aggcattctg tggccagcca 185520
aaaggtaccc cgatggccaa gcaattcctc tgaacaaaat gtaaagccag ccatgcattg 185580

-continued

```
ttaatcatcc atcacttccc attttatgga attgctttta aaatacattt ggcctctgcc 185640

cttcagaaga ctcgttttta aggtggaaac tcctgtgtct gtgtatatta caagcctaca 185700

tgacacagtt ggatttattc tgccaaacct gtgtaggcat tttataagct acatgttcta 185760

atttttaccg atgttaatta ttttgacaaa tatttcatat attttcattg aaatgcacag 185820

atctgcttga tcaattccct tgaataggga agtaacattt gccttaaatt ttttcgacct 185880

cgtctttctc catattgtcc tgctcccctg tttgacgaca gtgcatttgc cttgtcacct 185940

gtgagctgga gagaacccag atgttgttta ttgaatctac aactctgaaa gagaaatcaa 186000

tgaagcaagt acaatgttaa ccctaaatta ataaaagagt taacatccca tggca      186055
```